(12) United States Patent
Linder et al.

(10) Patent No.: US 7,594,926 B2
(45) Date of Patent: Sep. 29, 2009

(54) METHODS, SYSTEMS AND DEVICES FOR DELIVERING STENTS

(75) Inventors: Richard J. Linder, Sandy, UT (US);
Daryl R. Edmiston, Sandy, UT (US);
Steven W. Johnson, West Jordan, UT (US); Karri L. Schlegel, Salt Lake City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1301 days.

(21) Appl. No.: 10/290,099

(22) Filed: Nov. 7, 2002

(65) Prior Publication Data
US 2003/0149467 A1    Aug. 7, 2003

Related U.S. Application Data

(60) Provisional application No. 60/344,661, filed on Nov. 9, 2001, provisional application No. 60/345,333, filed on Nov. 9, 2001, provisional application No. 60/347,500, filed on Jan. 11, 2002, provisional application No. 60/341,092, filed on Dec. 12, 2001.

(51) Int. Cl.
*A61F 2/06* (2006.01)
*A61M 29/00* (2006.01)

(52) U.S. Cl. ..................... 623/1.11; 606/200
(58) Field of Classification Search ................. 623/1.11; 606/200, 108, 194, 195
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,195,637 A | 4/1980 | Gruntzig et al. ............. 128/348 |

(Continued)

FOREIGN PATENT DOCUMENTS

DE    40 30 998 C 2    4/1991

(Continued)

OTHER PUBLICATIONS

"Atherosclerotic Disease of the Aortic Arch as a risk Factor of Recurrent Ischemic Stroke," The New England Journal of Medicine, pp. 1216-1221 (May 1996).

(Continued)

*Primary Examiner*—Vy Q. Bui
(74) *Attorney, Agent, or Firm*—Crompton, Seager & Tufte, LLC

(57) ABSTRACT

A delivery device adapted to insert and deploy a stent within a body lumen. The delivery device includes a guide member adapted to retain a dilation assembly and a stent within a lumen thereof until the stent is to be deployed into the body lumen. The delivery device is configured to enable simultaneous insertion of the guide member, dilation assembly, stent, and optional guidewire within a body lumen. Following deploying the stent, the delivery device can be removed, while providing the capability of optionally maintaining the guide member or the guidewire to function or act as an exchange wire for additional surgical devices.

16 Claims, 30 Drawing Sheets

U.S. PATENT DOCUMENTS

| | | |
|---|---|---|
| 4,271,839 A | 6/1981 | Fogarty et al. ............... 128/344 |
| 4,307,722 A | 12/1981 | Evans ......................... 128/344 |
| 4,367,747 A | 1/1983 | Witzel ........................ 128/344 |
| 4,413,989 A | 11/1983 | Schjeldahl et al. ............ 604/96 |
| 4,425,908 A | 1/1984 | Simon ......................... 128/1 R |
| 4,447,227 A | 5/1984 | Kotsanis |
| 4,540,404 A | 9/1985 | Wolvek ........................ 604/96 |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib ................... 128/348.1 |
| 4,723,549 A | 2/1988 | Wholey et al. .............. 128/344 |
| 4,728,319 A | 3/1988 | Masch |
| 4,733,665 A | 3/1988 | Palmaz |
| 4,744,366 A | 5/1988 | Jang ........................... 128/344 |
| 4,748,982 A | 6/1988 | Horzewski et al. .......... 128/344 |
| 4,762,129 A | 8/1988 | Bonzel ........................ 128/344 |
| 4,771,777 A | 9/1988 | Horzewski et al. .......... 128/344 |
| 4,790,812 A | 12/1988 | Hawkins, Jr. et al. ....... 604/221 |
| 4,790,813 A | 12/1988 | Kensey |
| 4,793,348 A | 12/1988 | Palmaz ........................ 128/325 |
| 4,794,928 A | 1/1989 | Kletschka ................... 128/344 |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg .................... 128/345 |
| 4,886,061 A | 12/1989 | Fischell et al. |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. ......... 606/159 |
| 4,950,277 A | 8/1990 | Farr |
| 4,955,895 A | 9/1990 | Sugiyama et al. |
| 4,957,482 A | 9/1990 | Shiber |
| 4,969,890 A | 11/1990 | Sugita et al. ................ 606/192 |
| 4,969,891 A | 11/1990 | Gewertz |
| 4,979,951 A | 12/1990 | Simpson |
| 4,983,167 A | 1/1991 | Sahota ....................... 606/194 |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg ..................... 606/159 |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. ............... 604/104 |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot ....................... 606/159 |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. ................. 606/200 |
| 5,133,733 A | 7/1992 | Rasmussen et al. |
| 5,135,487 A | 8/1992 | Morrill et al. .............. 604/96 |
| 5,135,531 A | 8/1992 | Shiber |
| 5,135,535 A | 8/1992 | Kramer ....................... 606/194 |
| 5,152,771 A | 10/1992 | Sabbaghian et al. |
| 5,152,777 A | 10/1992 | Goldberg et al. |
| 5,156,594 A | 10/1992 | Keith ........................ 604/96 |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,209,730 A | 5/1993 | Sullivan ..................... 604/96 |
| 5,224,953 A | 7/1993 | Morgentaler |
| 5,232,445 A | 8/1993 | Bonzel ........................ 604/96 |
| 5,279,560 A | 1/1994 | Morrill et al. ............... 604/96 |
| 5,290,295 A | 3/1994 | Querals et al. |
| 5,300,025 A | 4/1994 | Wantink ..................... 604/96 |
| 5,306,286 A | 4/1994 | Stack et al. |
| 5,314,444 A | 5/1994 | Gianturco |
| 5,314,472 A | 5/1994 | Fontaine |
| 5,315,747 A | 5/1994 | Solar ........................ 29/447 |
| 5,318,576 A | 6/1994 | Plassche, Jr. et al. |
| 5,329,942 A | 7/1994 | Gunther et al. ............. 128/898 |
| 5,330,484 A | 7/1994 | Gunther et al. |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,364,357 A | 11/1994 | Aase ......................... 604/96 |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre .................... 606/180 |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,332 A | 3/1995 | Ressemann et al. ......... 604/96 |
| 5,395,349 A | 3/1995 | Quiachon et al. |
| 5,397,345 A | 3/1995 | Lazarus |
| 5,405,377 A | 4/1995 | Cragg |
| 5,409,454 A | 4/1995 | Fischell et al. |
| 5,409,458 A | 4/1995 | Khairkhahan et al. ....... 604/96 |
| 5,415,630 A | 5/1995 | Gory et al. |
| 5,419,774 A | 5/1995 | Willard et al. |
| 5,421,832 A | 6/1995 | Lefebvre .................... 604/53 |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,456,694 A | 10/1995 | Marin et al. ................ 606/198 |
| 5,462,529 A | 10/1995 | Simpson et al. |
| 5,476,104 A | 12/1995 | Sheahon |
| 5,484,418 A | 1/1996 | Quiachon et al. |
| 5,490,837 A | 2/1996 | Blaeser et al. .............. 604/96 |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,553 A | 8/1996 | Ressemann et al. ......... 604/96 |
| 5,549,556 A | 8/1996 | Ndondo-Lay et al. ....... 604/102 |
| 5,549,626 A | 8/1996 | Miller et al. ................ 606/200 |
| 5,562,724 A | 10/1996 | Vowerk et al. |
| 5,569,274 A | 10/1996 | Rapacki et al. |
| 5,569,275 A | 10/1996 | Kotula et al. |
| 5,578,009 A | 11/1996 | Kraus et al. ................ 604/96 |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,683,451 A | 11/1997 | Lenker et al. |

| | | | | | | |
|---|---|---|---|---|---|---|
| 5,695,519 | A | 12/1997 | Summers et al. ............ 606/200 | 6,129,739 | A | 10/2000 | Khosravi |
| 5,709,704 | A | 1/1998 | Nott et al. .................... 606/200 | 6,136,016 | A | 10/2000 | Barbut et al. |
| 5,720,764 | A | 2/1998 | Naderlinger | 6,142,987 | A | 11/2000 | Tsugita |
| 5,728,066 | A | 3/1998 | Daneshvar | 6,152,946 | A | 11/2000 | Broome et al. |
| 5,735,859 | A | 4/1998 | Fischell et al. | 6,165,200 | A | 12/2000 | Tsugita et al. |
| 5,746,758 | A | 5/1998 | Nordgren et al. | 6,168,579 | B1 | 1/2001 | Tsugita |
| 5,749,848 | A | 5/1998 | Jang et al. | 6,171,327 | B1 | 1/2001 | Daniel et al. |
| 5,769,816 | A | 6/1998 | Barbut et al. .................. 604/96 | 6,171,328 | B1 | 1/2001 | Addis |
| 5,779,716 | A | 7/1998 | Cano et al. | 6,179,851 | B1 | 1/2001 | Barbut et al. |
| 5,792,157 | A | 8/1998 | Mische et al. | 6,179,859 | B1 | 1/2001 | Bates et al. |
| 5,792,300 | A | 8/1998 | Inderbitzen et al. | 6,179,861 | B1 | 1/2001 | Khosravi et al. |
| 5,795,322 | A | 8/1998 | Boudewijn | 6,203,561 | B1 | 3/2001 | Ramee et al. |
| 5,797,952 | A | 8/1998 | Klein | 6,206,868 | B1 | 3/2001 | Parodi |
| 5,800,457 | A | 9/1998 | Gelbfish | 6,214,026 | B1 | 4/2001 | Lepak et al. |
| 5,800,525 | A | 9/1998 | Bachinski et al. | 6,221,006 | B1 | 4/2001 | Dubrul et al. |
| 5,807,398 | A | 9/1998 | Shaknovich | 6,224,620 | B1 | 5/2001 | Maahs |
| 5,810,874 | A | 9/1998 | Lefebvre | 6,231,544 | B1 | 5/2001 | Tsugita et al. |
| 5,814,064 | A | 9/1998 | Daniel et al. ................. 606/200 | 6,235,044 | B1 | 5/2001 | Root et al. |
| 5,817,102 | A | 10/1998 | Johnson et al. | 6,235,045 | B1 | 5/2001 | Barbut et al. |
| 5,824,041 | A | 10/1998 | Lenker et al. | 6,238,412 | B1 | 5/2001 | Dubrul et al. |
| 5,827,324 | A | 10/1998 | Cassell et al. ............... 606/200 | 6,245,087 | B1 | 6/2001 | Addis |
| 5,833,644 | A | 11/1998 | Zadno-Azizi et al. | 6,245,088 | B1 | 6/2001 | Lowery |
| 5,833,650 | A | 11/1998 | Imran | 6,245,089 | B1 | 6/2001 | Daniel et al. |
| 5,846,260 | A | 12/1998 | Maahs | 6,258,115 | B1 | 7/2001 | Dubrul |
| 5,848,964 | A | 12/1998 | Samuels | 6,264,663 | B1 | 7/2001 | Cano |
| 5,873,906 | A | 2/1999 | Lau et al. | 6,264,672 | B1 | 7/2001 | Fisher |
| 5,876,367 | A | 3/1999 | Kaganov et al. ................ 604/8 | 6,270,513 | B1 | 8/2001 | Tsugita et al. |
| 5,893,867 | A | 4/1999 | Bagaoisan et al. | 6,277,138 | B1 | 8/2001 | Levinson et al. |
| 5,895,399 | A | 4/1999 | Barbut et al. ................. 606/159 | 6,277,139 | B1 | 8/2001 | Levinson et al. |
| 5,902,263 | A | 5/1999 | Patterson et al. | 6,280,413 | B1 | 8/2001 | Clark et al. |
| 5,906,618 | A | 5/1999 | Larson, III | 6,287,321 | B1 | 9/2001 | Jang |
| 5,908,435 | A | 6/1999 | Samuels | 6,290,710 | B1 | 9/2001 | Cryer et al. |
| 5,910,154 | A | 6/1999 | Tsugita et al. | 6,309,399 | B1 | 10/2001 | Barbut et al. |
| 5,911,734 | A | 6/1999 | Tsugita et al. ............... 606/200 | 6,319,268 | B1 | 11/2001 | Ambrisco et al. |
| 5,916,193 | A | 6/1999 | Stevens et al. | 6,344,049 | B1 | 2/2002 | Levinson et al. |
| 5,925,016 | A | 7/1999 | Chornenky et al. | 6,350,278 | B1 | 2/2002 | Lenker et al. |
| 5,925,060 | A | 7/1999 | Forber | 6,443,971 | B1 | 9/2002 | Boylan et al. |
| 5,925,062 | A | 7/1999 | Purdy | 6,514,280 | B1 | 2/2003 | Gilson |
| 5,925,063 | A | 7/1999 | Khosravi | 6,582,448 | B1 | 6/2003 | Boyle et al. |
| 5,928,203 | A | 7/1999 | Davey et al. | 6,613,072 | B2 | 9/2003 | Lau et al. |
| 5,928,218 | A | 7/1999 | Gelbfish | 6,984,242 | B2 | 1/2006 | Campbell et al. |
| 5,934,284 | A | 8/1999 | Plaia et al. | 2002/0065475 | A1 | 5/2002 | Meguro et al. |
| 5,935,139 | A | 8/1999 | Bates | | | | |
| 5,938,645 | A | 8/1999 | Gordon | | | | |

FOREIGN PATENT DOCUMENTS

| | | |
|---|---|---|
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0775470 B1 | 3/1999 |
| GB | 2 020 557 A | 5/1979 |
| JP | 8-187294 A | 7/1996 |
| WO | WO 96/01591 | 1/1996 |
| WO | WO 96/04875 A1 | 2/1996 |
| WO | WO 96/23441 | 8/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/49952 | 11/1998 |

| | | | |
|---|---|---|---|
| 5,941,869 | A | 8/1999 | Patterson et al. |
| 5,941,896 | A | 8/1999 | Kerr |
| 5,947,995 | A | 9/1999 | Samuels |
| 5,951,585 | A | 9/1999 | Cathcart et al. |
| 5,954,745 | A | 9/1999 | Gertler et al. |
| 5,976,172 | A | 11/1999 | Homsma et al. |
| 5,980,555 | A | 11/1999 | Barbut et al. |
| 5,989,210 | A | 11/1999 | Morris et al. |
| 5,989,271 | A | 11/1999 | Bonnette et al. |
| 5,989,281 | A | 11/1999 | Barbut et al. |
| 5,993,469 | A | 11/1999 | McKenzie et al. |
| 5,997,557 | A | 12/1999 | Barbut et al. |
| 6,001,118 | A | 12/1999 | Daniel et al. |
| 6,007,557 | A | 12/1999 | Ambrisco et al. |
| 6,010,522 | A | 1/2000 | Barbut et al. |
| 6,013,085 | A | 1/2000 | Howard |
| 6,019,787 | A | 2/2000 | Richard et al. |
| 6,027,520 | A | 2/2000 | Tsugita et al. |
| 6,042,598 | A | 3/2000 | Tsugita et al. |
| 6,051,014 | A | 4/2000 | Jang |
| 6,051,015 | A | 4/2000 | Maahs |
| 6,053,932 | A | 4/2000 | Daniel et al. |
| 6,059,814 | A | 5/2000 | Ladd |
| 6,066,149 | A | 5/2000 | Samson et al. |
| 6,066,158 | A | 5/2000 | Engelson et al. |
| 6,068,645 | A | 5/2000 | Tu |
| 6,086,605 | A | 7/2000 | Barbut et al. |
| 6,117,154 | A | 9/2000 | Barbut et al. |
| 6,126,685 | A | 10/2000 | Lenker et al. |

| | | |
|---|---|---|
| WO | WO 98/50103 | 11/1998 |
| WO | WO 99/22673 | 5/1999 |

OTHER PUBLICATIONS

"Endovascular grafts, Stents Drive Interventional Radiology Growth," Cardiovascular Device Update 2(3):1-12 (Mar. 1996).

Cragg et al., "A New Percutaneous Vena Cava Filger," AJR 141:601-604 (Sep. 1983).

Cragg et al., "Nonsurgical Placement of Arterial Endoprosthesis: A new Technique Using Nitinol Wire," AJR pp. 261-263 (Apr. 1983).

Diethrich et al., "Percutaneous Techniques for Endoluminal Carotid Interventions," J. Endovasc. Surg. 3:182-202 (1996).

Fadali, "A Filtering Device for the Prevention of Particulate Embolization During the Course of Cardiac Surgery," Surgery 64(3):634-639 (Sep. 1968).

Haissaguerre et al., "Spontaneous Initiation of Atrial Fibrillation by Ectopic Beats Originating in the Pulmonary Veins," The New England Journal of Medicine 339(10):659-666 (Sep. 1998).

Jordan, Jr. et al., "Microemboli Detected by Transcranial Doppler Monitoring . . . ," Cardiovascular Surgery 7(1)33-38 (Jan. 1999).

Karalis et al., "Recognition and Embolic Potential of Inraaortic Atherosclerotic Debris," American College of Cardiology 17;73-78 (Jan. 1991).

Lesh, "Can Catheter Ablation Cure Atrial Fibrillation?" ACC Current Journal Review pp. 38-40 (Sep./Oct. 1997).

Lund et al., "Long-Term Patentcy of Ductus Arteriosus After Ballon Dilation: an Experimental Study," Laboratory Investigation 69(4):772-774 (Apr. 1984).

Marache et al., Percutaneous Transluminal Venous Angioplasty . . . , American Heart Jounal 125(2Pt 1):362-366 (Feb. 1993).

Mazur et al., "Directional Atherectomy with the Omnicath™: A Unique New Catheter System," Catheterization and Cardiovascular Diagnosis 31:79-84 (1994).

Moussa, "Stents Don't Require Systemic Anticoagulation . . . But the Technique (and Results) Must be Optimal," Journal of Invasive Cardiol. 8(E):3E-7E (1996).

Nakanishi et al., "Catheter Intervention to Venous System Using Expandable Metallic Stents," Rinsho Kyobu Geka 14(2):English Abstract Only (Apr. 1994).

Onal et al., "Primary Stenting for Complex Atherosclerotic Plaques in Aortic and Iliac Stenoses," Cardiovascular & Interventional Radiology 21(5):386-392 (1998).

Theron et al., "New Triple Coaxial Catheter System for Carotid Angioplasty with Cerebral Protection," American Jounal of Neuroradiology 11:869-874 (1990).

Tunick et al., "Protrudiing Atherosclerotic Plaque in the Aortic Archo of Patients with Systemic Embolization: A new Finding Seen by Transesophageal Echocardiography," American Heart Journal 12093):658-660 (Sep. 1990).

Tunick et al., "Protruding Atheromas in the Thorzcic Aortic and Systemic Embolization," pp. 423-427 American College of Physicians (1991).

Waksman er al., "Distal Embolization is Common After Directional Atherectomy . . . ," American Hear Jornal 129(3):430-435 (1995).

Wholey et al., "PTA and Stents in the Treatment of Rectracranial Circulation," The Journal of Invasive Cardiology 8(E):25E-30E (1996).

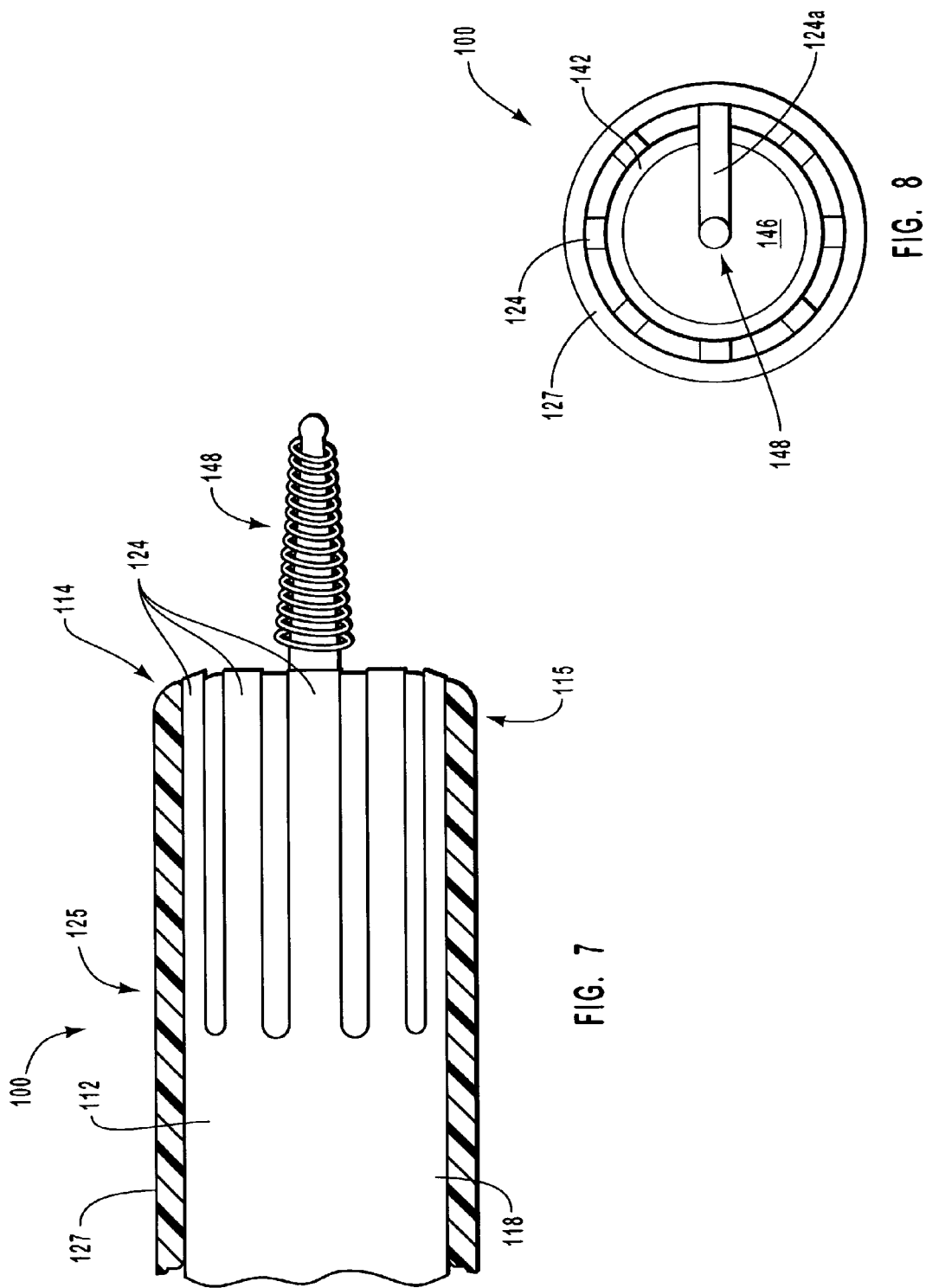

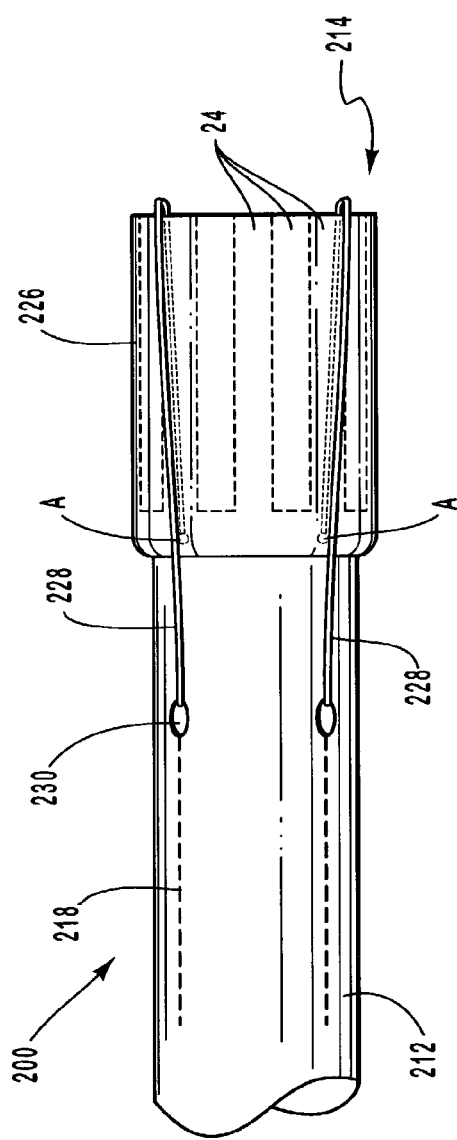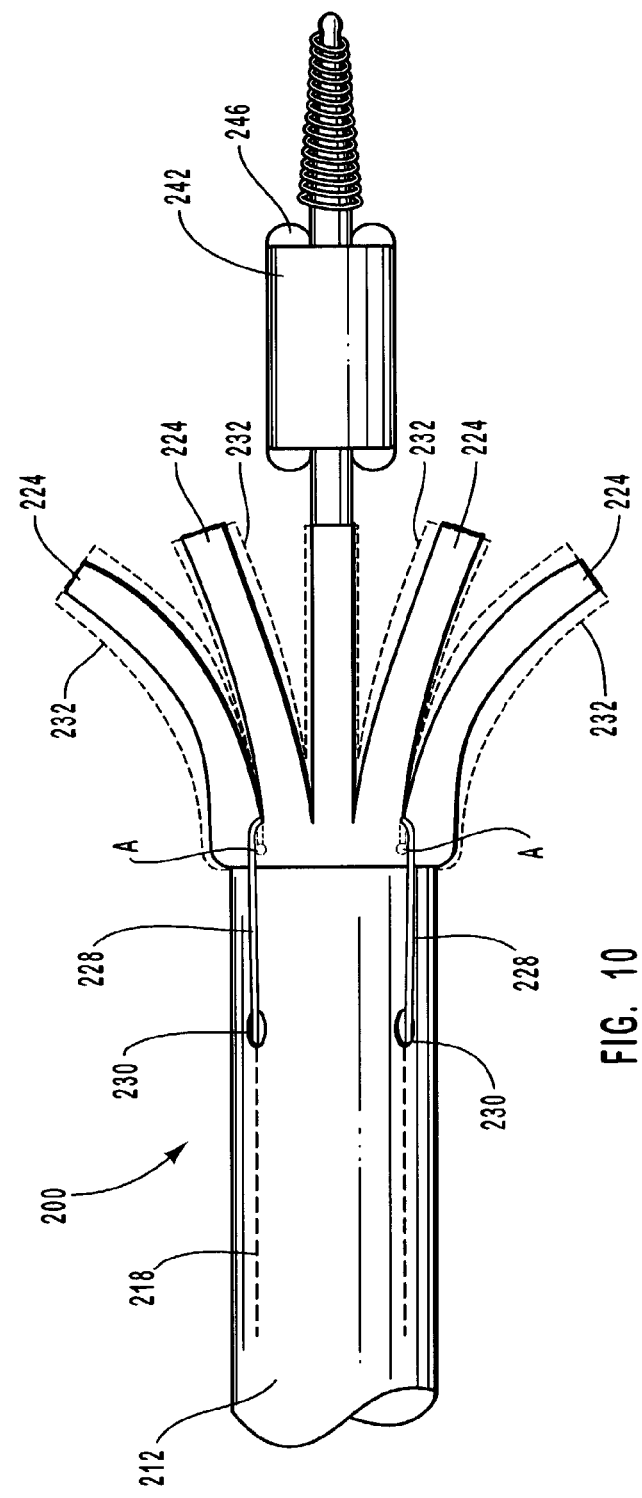

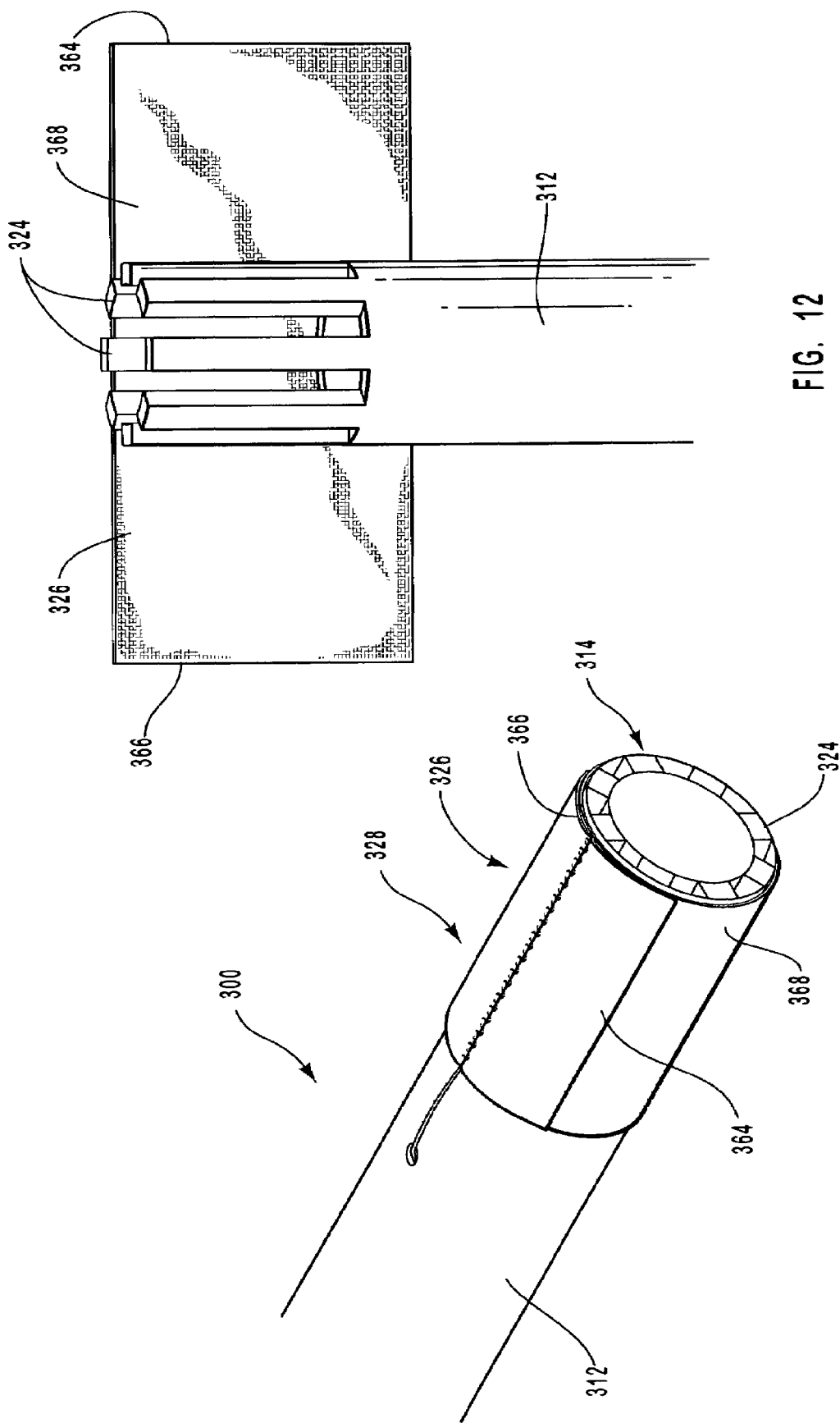

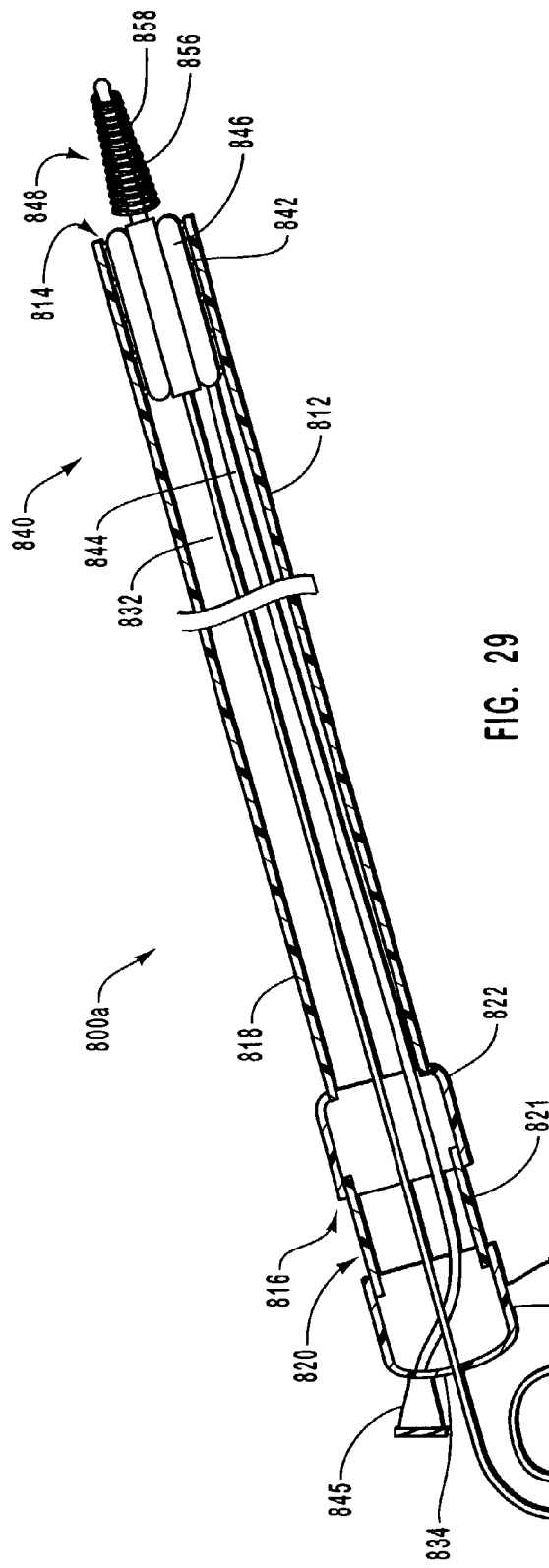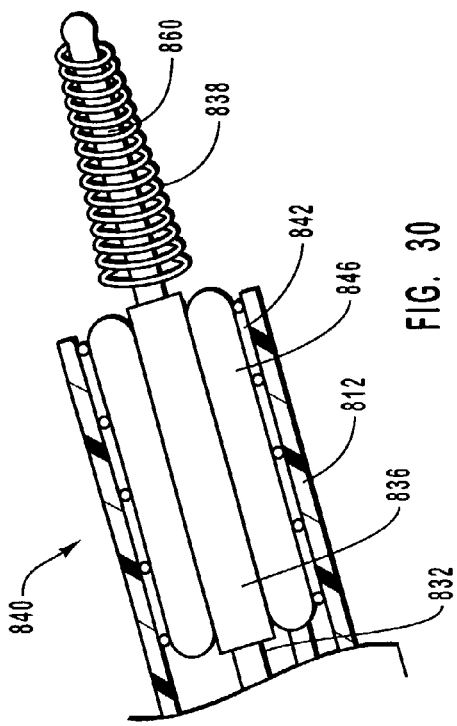

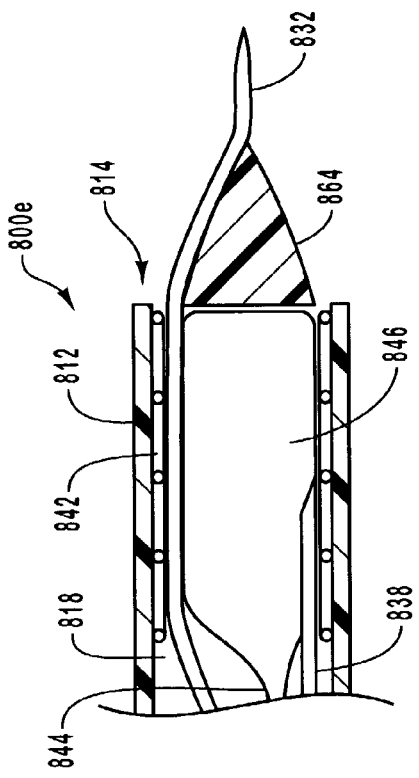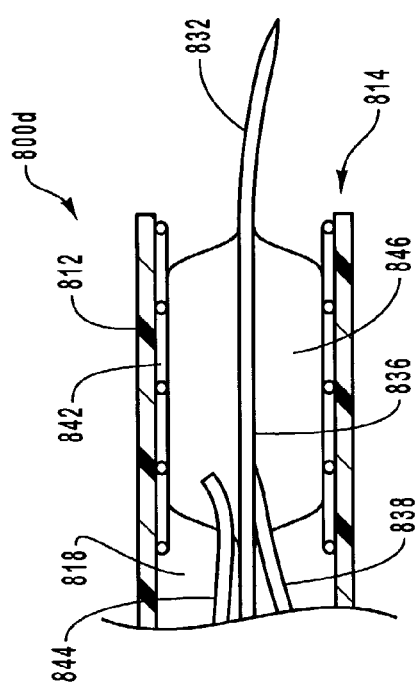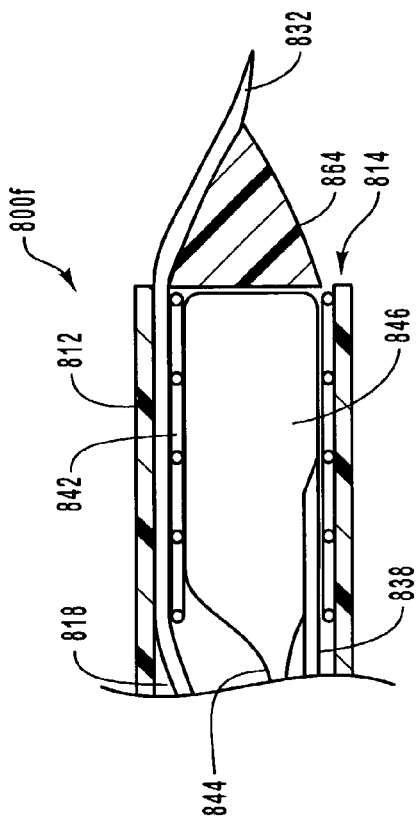
FIG. 33
FIG. 34
FIG. 35

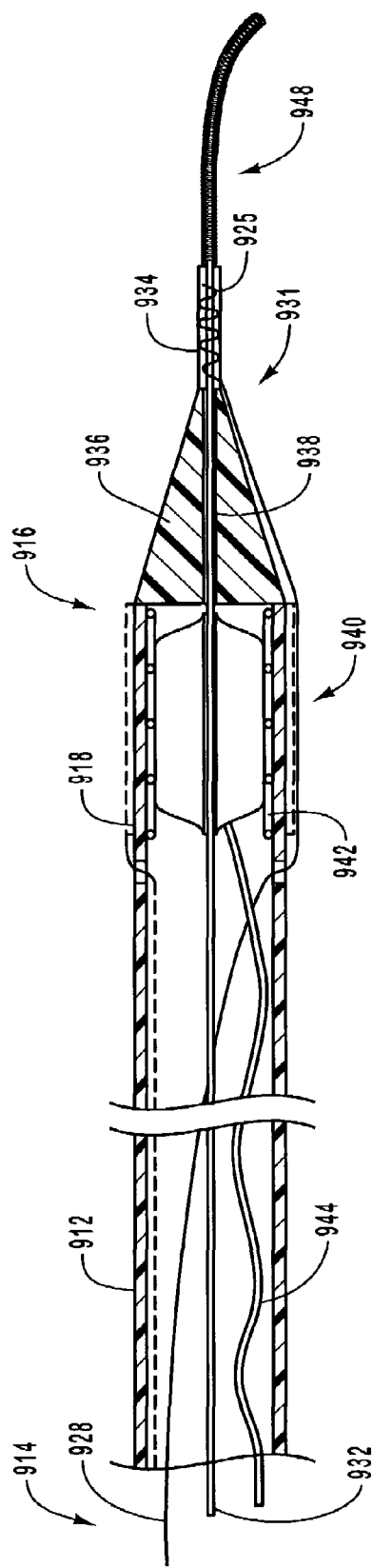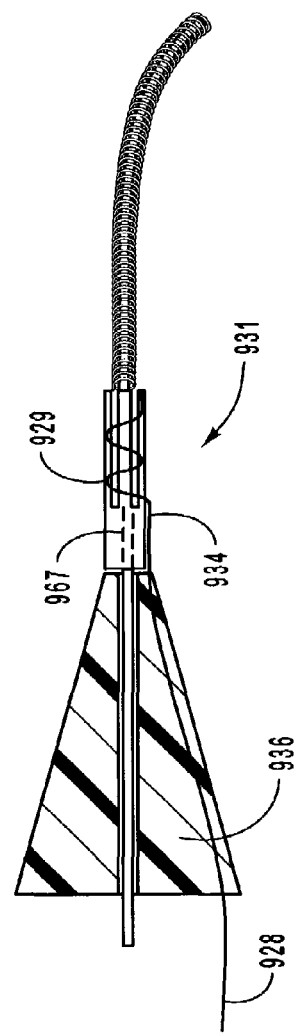
FIG. 37
FIG. 38

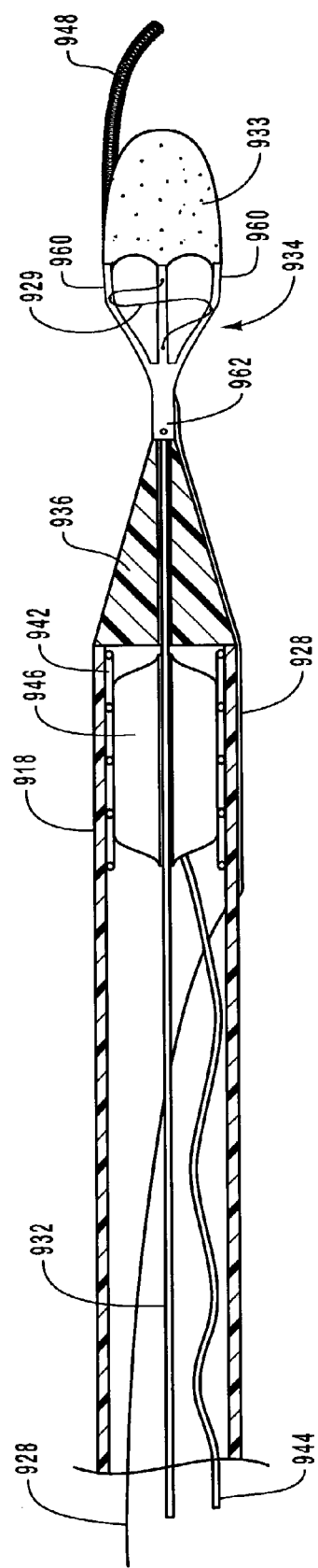
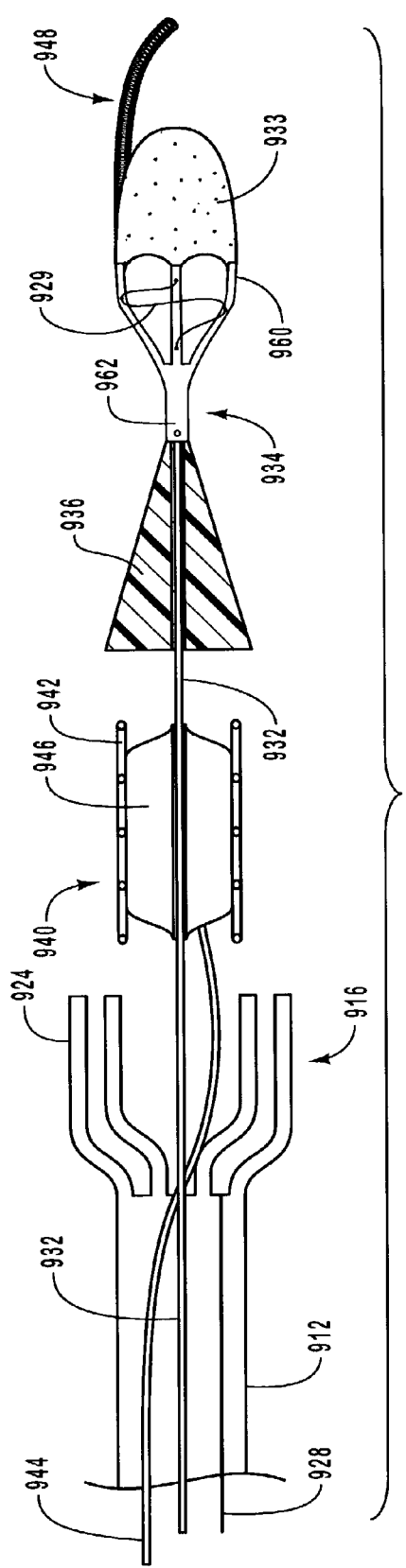
FIG. 39
FIG. 40

METHODS, SYSTEMS AND DEVICES FOR DELIVERING STENTS

CROSS-REFERENCE TO RELATED APPLICATIONS

This patent application claims priority to U.S. Provisional Patent Application Ser. No. 60/344,661, filed Nov. 9, 2001, U.S. Provisional Patent Application Ser. No. 60/345,333, filed Nov. 9, 2001, U.S. Provisional Patent Application Ser. No. 60/347,500, filed Jan. 11, 2002, and U.S. Provisional Patent Application Ser. No. 60/341,092, filed Dec. 12, 2001, the disclosures of which are herein incorporated by this reference.

BACKGROUND OF THE INVENTION

1. The Field of the Invention

The invention generally relates to the field of interventional cardiology. More specifically, the invention relates to interventional cardiology procedures that require the placing of a stent in a body lumen, such as a body lumen of a patient or animal. The present invention further relates to systems for providing embolic protection during placing of a stent in a body lumen.

2. The Relevant Technology

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessel. Angioplasty, for example, is a widely known procedure wherein an inflatable balloon is introduced into the occluded region. The balloon is inflated, dilating the occlusion, and thereby increasing the intra-luminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the top thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained with the interior lumen of the catheter. This process is repeated until a sufficient amount of fatty material is removed and substantially normal blood flow is resumed.

In another procedure, introducing a stent into the stenosed region to open the lumen of the vessel treats stenosis within the artery or other blood vessel. The stent typically includes a substantially cylindrical tube or mesh sleeve made from such material as stainless steel or Nitinol. The design of the material permits the diameter of the stent to be radially expanded, while still providing sufficient rigidity such that the stent maintains its shape once it has been enlarged to a desired size.

To place a stent, many medical devices are typically used. Once access to the inside of the arterial system is established, usually through the femoral artery, a guide catheter is inserted into the artery and the tip thereof is guided to a position just proximal to the stenosed region to be treated. This guide catheter serves the purpose of allowing other devices to rapidly be delivered to that position without each being carefully guided from the point of access, through the tortuous anatomy of the arterial system to the point of intervention.

Typically, a small diameter guidewire is then inserted through the guide catheter and guided to the point distal to the stenosed region. When guidewire access to the lesion is established, and if there is sufficient cross sectional area in the narrowed part of the lesion, a stent, mounted on a delivery device, is installed over the guidewire. When correctly placed within the stenosed region, the stent will then be deployed, propping open the vessel at that point.

Various types of stents are used in these cases, but a common one requires that the stent be deployed from, or expanded from, a compressed state by a balloon upon which it is mounted. The balloon is inflated from the proximal end of the delivery device to a high pressure, which both opens the stenosis and embeds the stent into the inner lumen of the vessel at that point.

Once the guidewire is placed, the guidewire is used as a guide for all of the other devices that are used in the procedure. These devices have an inner lumen through which the proximal end of the guidewire, which is outside of the body of the patient, is inserted. The device is then slid along the guidewire into the body, allowing the guidewire to guide the device to the required position in the vascular system. The process of sliding another device over the guidewire is commonly known as an exchange.

Two basic types of devices facilitate exchanging of stent systems and dilation balloons. The first type of device encloses a guidewire within an inner lumen of the device for the entire length of the device. The second type of device only encloses the guidewire for a small distal segment of the device, with the remainder of the guidewire exiting from the inner lumen of the device through a side hole to allow the device and the guidewire to be side by side. In both cases, control of the guidewire is paramount during the exchange as the correct positioning of the device is reliant upon maintaining the position of the guidewire; this being difficult as at least a section of the guidewire is inaccessible due to it being enclosed in the inner lumen of the device being exchanged.

Providing a stent delivery device that reduces the complexity of an interventional procedure would advance the art of stent delivery. Furthermore, reducing the number of devices used to perform a stent implanting procedure would advance the art of stent delivery.

In addition, when these interventional procedures are performed, embolic particles may break off, flow down-stream, and cause potential adverse events. Devices are emerging that are designed to catch or filter these particles to prevent their down-stream flow, to occlude the vessel during the intervention, and then allowing the particles to be aspirated out before they may flow downstream.

Current technology for embolic protection devices requires that they be delivered in a sheath distal to the point of intervention. This requires crossing the lesion with a large-diameter, relatively stiff device that is itself a potential embolic event that may occur before the embolic protection device is in place. The sheath must then be removed allowing the filter to be deployed in the vessel. After the device is deployed, balloons, stents, or other therapies of choice may be exchanged over the device to treat the area of interest. When the procedure is completed, the embolic protection device is captured by another catheter that is exchanged over the embolic protection device capturing any potential embolic material within it. This relatively complicated procedure adds complexity to providing stenting and other procedures.

The device and methods described herein are meant to overcome deficiencies of the current devices allowing quicker, safer and easier protection and stenting procedures to be undertaken.

BRIEF SUMMARY OF THE INVENTION

Embodiments of the present invention can provide systems, methods, and devices that combine the functionality of a guidewire, a stent delivery device, a dilation balloon, and an embolic protection device, or subset grouping thereof, into a single device insertable into a body lumen. In this manner, embodiments of the present invention reduce the number of devices needed to perform a procedure, decrease the time needed to perform the procedure, reduce the difficulty and complexity of the procedure, thereby creating the potential for safer procedures and increased effectiveness to the patient.

In one embodiment, a delivery device includes a guide member having a distal end and a proximal end. The guide member functions as a guide catheter, a guidewire, and a stent delivery device. A dilation assembly is disposed at the distal end of the guide member with a stent preloaded upon the dilation assembly. The distal end of the guide member is configured to apply a restraining force upon the dilation assembly to selectively maintain the dilation assembly and stent within a lumen of the delivery device. Associated with the distal end of the guide member is a restraining member or mechanism that can be operated to release the restraining force applied to the dilation assembly and stent, thereby allowing the dilation assembly and stent to be deployed from within the lumen. The restraining mechanism cooperates with an actuating assembly to deploy the dilation assembly and stent.

In one embodiment, the actuating assembly cooperates with a proximal end of the guide member and includes an actuating member that extends from the restraining mechanism or member at a distal end of the delivery device to an actuating element disposed at the proximal end of the guide member. Thus, operation of the actuating element translates movement to the actuating member to release the restraining mechanism or member and release the restraining force applied by the restraining mechanism or member, whether alone or in combination with the distal end of the guide member, upon the dilation assembly and/or the stent.

In operation, the delivery device is placed in position within a body lumen of a patient, with the dilation assembly and stent in a restrained position. Operation of the actuating assembly releases the dilation assembly and the stent from within the guide member. The guide member may be pulled proximally to allow the dilation assembly and stent to be entirely free of the guide member. Alternatively, a dilation tube and/or a positioning member connected to the dilation assembly may be advanced distally to deploy the dilation assembly and the stent. The stent may then be placed in the vasculature by inflating the dilation balloon associated with the dilation assembly, for example, through the dilation tube. After the stent is implanted, the dilation assembly is deflated and the delivery device can be removed from the patient.

According to another aspect of the present invention, the delivery device can include an embolic protection device that is adapted to collect embolic particles released during the procedure. As the stent is implanted, the embolic protection device can filter the blood flowing past the lesion and prevent embolic particles or matter flowing downstream. In one configuration, the embolic protection device is mounted to a distal end of a guidewire associated with the delivery device. The embolic protection device can be a filter assembly that includes a filter and a filter basket. The filter basket includes a plurality of struts that restrain the filter during insertion of the delivery device into the body lumen, while supporting and deploying the filter upon releasing a restraining force applied to the plurality of struts to maintain the filter assembly in a closed position during insertion of the delivery device. The structures used to apply the restraining force to the plurality of struts can be similar to the structures applying the restraining force to the dilation assembly and/or stent.

According to another aspect of one embodiment of the present invention, the delivery device may cooperate with a capture mechanism or device for retrieving the filter assembly without removing the delivery device from the body.

Thus, the delivery devices of the present invention allow protected interventions to be accomplished with a single device insertion, without requiring exchanges, while still allowing guidewire access distal to the treatment region throughout the entire procedure.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 7 illustrates a plan view of a distal end of another embodiment of the stent delivery device in accordance with another aspect of the present invention;

FIG. 8 illustrates a side view of the distal end of the stent delivery device of FIG. 7 in accordance with one aspect of the present invention;

FIG. 9 illustrates a perspective view of a distal end of another embodiment of a stent delivery device in accordance with one aspect of the present invention;

FIG. 10 illustrates a perspective view of the distal end of the stent delivery device of FIG. 9 with deployed dilation assembly in accordance with one aspect of the present invention;

FIG. 11 illustrates a perspective view of another embodiment of a stent delivery device of the present invention;

FIG. 12 illustrates another perspective view of the distal end of the delivery device of FIG. 11 before a restraining member is coupled to the delivery device;

FIG. 29 illustrates a sectional side view of another embodiment of a stent delivery device of the present invention in accordance with another aspect of the present invention;

FIG. 30 illustrates a sectional side view of the distal end of the stent delivery device of FIG. 30 in accordance with another aspect of the present invention;

FIG. 33 illustrates a sectional side view of another embodiment of a stent delivery device in accordance with another aspect of the present invention;

FIG. 34 illustrates a sectional side view of yet another embodiment of a stent delivery device in accordance with another aspect of the present invention;

FIG. 35 illustrates a sectional side view of still another embodiment of a stent delivery device in accordance with another aspect of the present invention;

FIG. 37 illustrates a sectional side view of an embodiment of a stent delivery device that includes an embolic protection device in accordance with another aspect of the present invention;

FIG. 38 illustrates a sectional side view of a distal end of the delivery device of FIG. 37;

FIG. 39 illustrates a sectional side view of a portion of the delivery device of FIG. 37 with a filter assembly deployed in accordance with another aspect of the present invention;

FIG. 40 illustrates a sectional side view of a portion of the delivery device of FIG. 37 with the filter assembly and the stent deployed in accordance with another aspect of the present invention;

DETAILED DESCRIPTION OF THE PREFERRED EMBODIMENTS

The present invention provides systems, methods, and devices that combine the functionality of a guide catheter, a guidewire, a stent delivery device, a dilation balloon, and/or an embolic protection device, or a subset group of such devices, into a single device that is insertable into a body lumen. In this manner, the present invention reduces the number of devices needed to deliver and position a stent, providing the possibility of decreasing the time needed to perform procedures and reducing the difficulty and complexity associated with performing a procedure. Further, embodiments of the present invention aid with decreasing the possibility of patient complications during and subsequent to the procedure.

Figure 1:
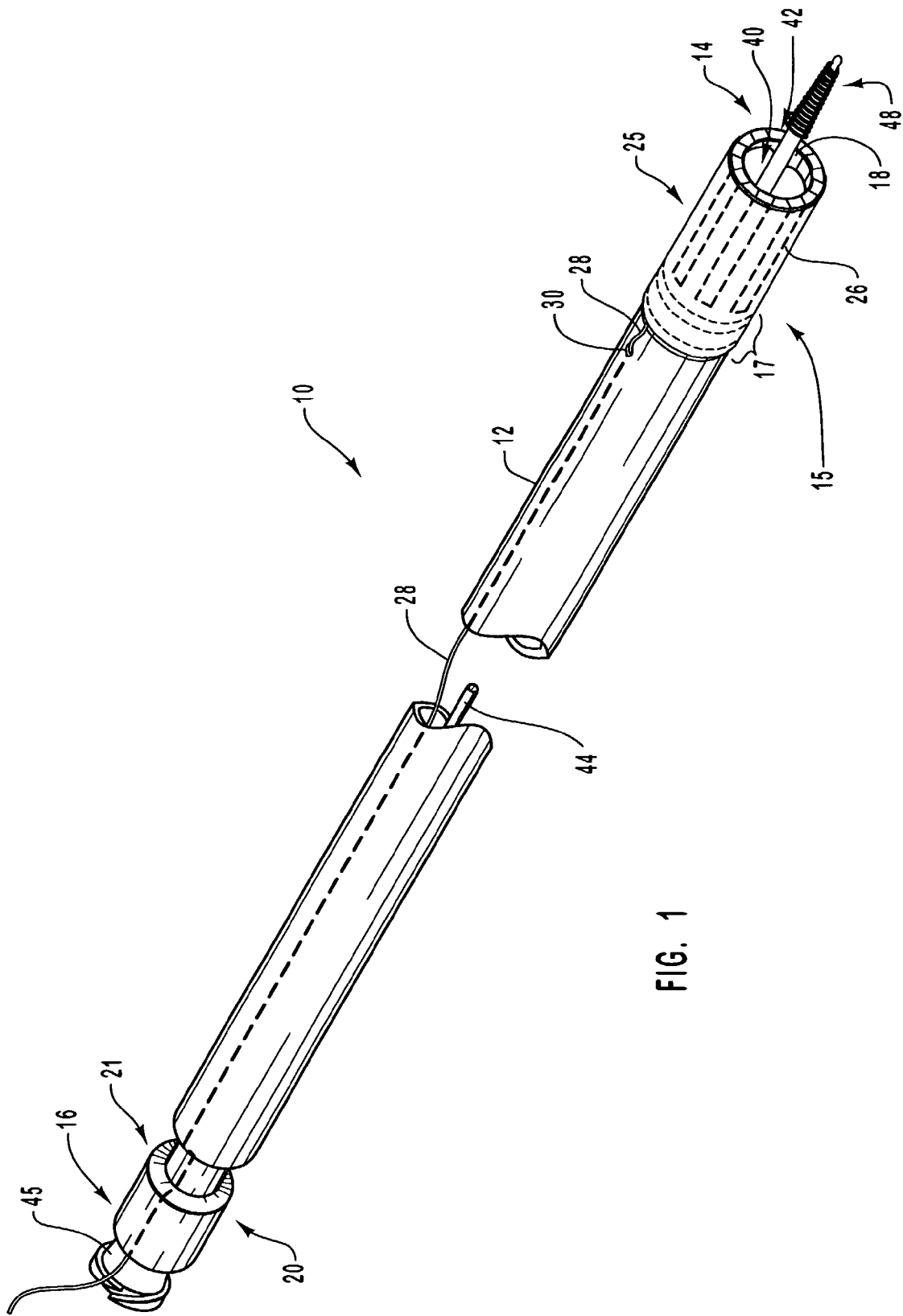
FIG. 1 illustrates a perspective view of an exemplary stent delivery device in accordance with one aspect of the present invention.

Referring now to FIG. 1, depicted is an exemplary embodiment of a delivery device of the present invention, designated by reference number 10. As illustrated, delivery device 10 includes a guide member 12 having a distal end 14 and a proximal end 16. The term "guide member" can refer to any structure that is capable of functioning as a guidewire that can be steered through the tortuous anatomy of a patient. It will be appreciated that guide member 12 can be hollow or partially hollow depending upon design considerations.

Figure 2:
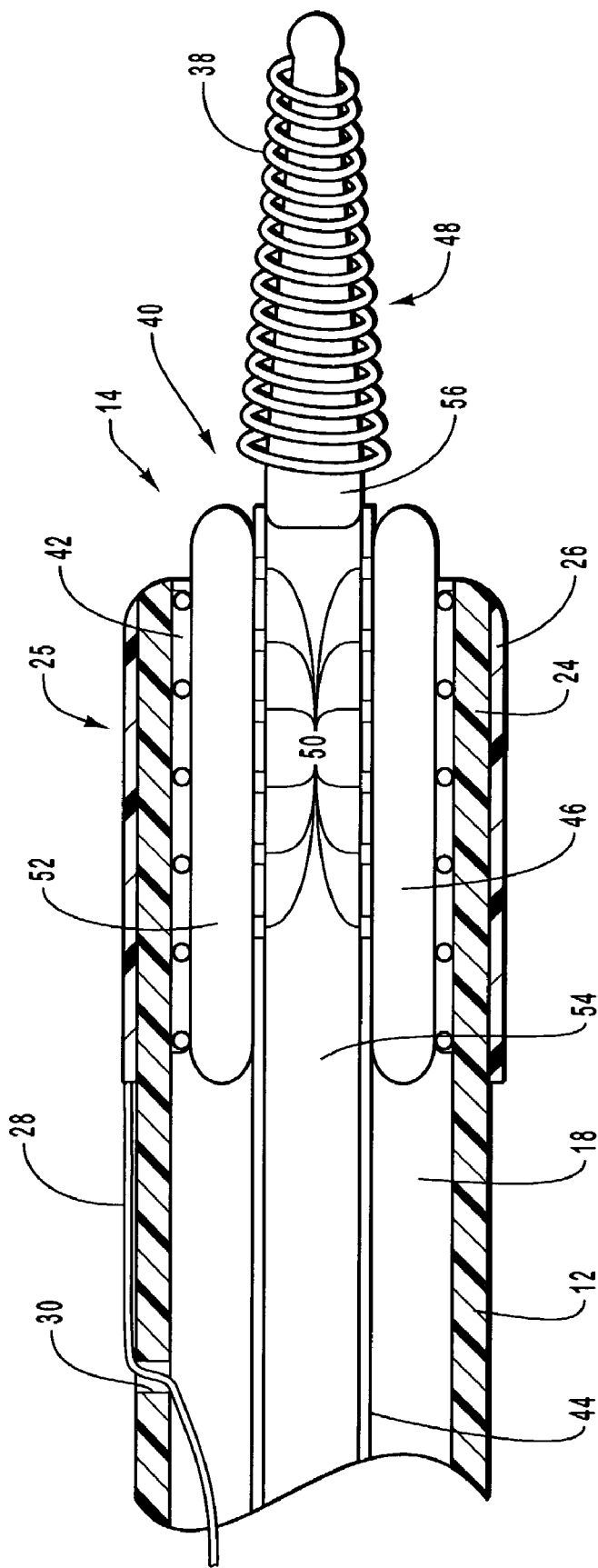
FIG. 2 illustrates a sectional side view of a distal end of the device of FIG. 1.

Extending between distal end 14 and proximal end 16 of guide member 12 is a lumen 18 within which is disposed a dilation assembly 40 and a stent 42 (see FIG. 2). Distal end 14 of guide member 12 includes a tip 15 that is configured for percutaneous insertion into a body lumen, while proximal end 16 either includes or is adapted to cooperate with an actuating assembly 20 that is adapted to deploy dilation assembly 40 and/or stent 42.

Illustratively, guide member 12 can have an outside diameter of between about 0.010 inches to about 0.650 inches and an inside diameter or diameter of lumen 18 from about 0.004 inches to about 0.55 inches. Additionally, guide member 12 can be fabricated from a variety of different materials. For example, guide member 12 can be fabricated from Nitinol, steel, metals, metal alloys, composites, plastic, polymers, synthetic materials, such as, but not limited to, PEEK, Rydel, or combinations thereof. Additionally, guide member 12 can have the configuration of a braid-reinforced polymer tube or a rigid polymer tube. Furthermore, guide member 12 can be covered with one or more coatings. For instance, and not by way of limitation, guide member 12 can include one or more coatings that improve lubricity, reduce platelet aggregation, or have anti-thrombogenic properties. In addition to the above, guide member 12 can include one or more hydrophilic coatings, heparinized coatings, Polytetrafluoroethylene (PTFE) coatings, silicone coatings, combinations thereof, or other coatings that may aid with positioning guide member 12 and/or preventing damage to the body lumen.

Optionally, guide member 12 may include one or more cuts, slits, grooves, or other structures, illustratively identified by numeral 17, that provide flexibility to all or a portion of guide member 12. Although reference is made to use of cuts, slits, or grooves to provide flexibility, it can be appreciated by one skilled in the art that guide member 12 or other portion of device 10 may have a lattice structure, i.e., portions of guide member 12 or device 10 removed therefrom, which provides flexibility to a portion of guide member 12 and/or other portion of device 10.

The cuts, slits, or grooves can be located at any location of guide member 12 and may have various pitches to allow or provide for different flexibilities. These one or more grooves, cuts or slits can partially or completely extend through portions of guide member 12. Additionally, these grooves, cuts, or slits can have a variety of different configurations, such as but not limited to, straight, helical, geometric, combinations thereof, or various other configurations known to those skilled in the art, so long as those same provide flexibility to guide member 12. Further, any number of grooves, cuts, or slits can be included in guide member 12 and optionally portions of dilation assembly 40. For example, the more grooves, cuts, or slits included in guide member 12 or a portion of dilation assembly 40, the greater the flexibility of guide member 12, and hence delivery device 10. Similarly, the depth of each groove, cut, or slit can vary depending upon the desired flexibility. For instance, the deeper the groove, cut, or slit, the greater the flexibility of guide member 12, and hence delivery device 10. Furthermore, differences in the configuration of each groove, cut, or slit can affect the flexibility of guide member 12 and therefore delivery device 10. For instance, the steeper the sides of a particular groove, cut, or slit, the less flexibility provided to guide member 12 and/or delivery device 10.

FIG. 1 depicts dilation assembly 40 and stent 42 (FIG. 2) disposed at tip 15 of guide member 12. Dilation assembly 40 terminates in an atraumatic tip 48. Dilation assembly 40 and stent 42 are retained at tip 15 of guide member 12 by a restraining mechanism or restraining member 25. In the embodiment of FIG. 1, an actuating member 28 operates restraining member 25 and extends to an actuating assembly 20 disposed at a proximal end of device 10. Actuating member 28 extends to the proximal end of device 10 and is exposed to allow the restraint applied by restraining member 25 to be released as a clinician moves actuating member 28 in a proximal direction. Alternatively, actuating member 28 can optionally extend outside guide member 12 to proximal end 16 of device 10.

Dilation assembly 40 is connected to a dilation tube 44 that extends along the length of guide member 12. Dilation tube 44 is used to fill a dilation balloon 46 with a fluid. The fluid may be introduced through a luer lock fitting 45 located at proximal end 16 of guide member 12. Dilation tube 44 may also be used, in some embodiments, as a positioning member for deploying dilation assembly 40 and stent 42. Additionally, dilation assembly 40 of device 10 is coupled by dilation tube 44 to actuating element 21. By sliding actuating element 21 with respect to proximal end 16 of guide member 12, dilation assembly 40 is moved with respect to guide member 12 and can be deployed from tip 15 of guide member 12. These and other features of the present invention will now be described in further detail.

With reference now to FIG. 2, distal end 14 of guide member 12 includes one or more struts 24 that are adapted to retain dilation assembly 40 and stent 42 within lumen 18 until the same are to be deployed. Each strut 24 can be biased to extend outwardly to release dilation assembly 40 and stent 42. Although reference is made to each strut 24 being biased to extend outwardly, it can be understood by one skilled in the art that each strut 24 need not be biased to extend outwardly.

The one or more struts 24 can be formed using a variety of different processes. For instance, the processes can include, but not limited to, machining processes performed using a laser or conventional machining process, including, but not limited to, hydro-machining, grinding, end milling, slitting saws, abrasive saws, electrical discharge machines, combinations thereof, or other machining processes capable of creating slots or slits sufficient to form one or more struts 24. In the embodiment of FIG. 2, each strut 24 can be formed integrally with guide member 12. In other embodiments, one or more of struts 24 are formed as part of a discrete strut assembly that is attached to guide member 12.

Surrounding struts 24 is restraining member 25. In the embodiment of FIG. 2, restraining member 25 is a sleeve 26. Sleeve 26 is adapted to retain or maintain struts 24 in a restrained or closed configuration so that the combination of sleeve 26 and struts 24 maintain dilation assembly 40 and stent 42 within lumen 18. Sleeve 26 is adapted to cooperate with the exterior of guide member 12 so that sleeve 26 can be displaced in a proximal direction to release struts 24. Since struts 24, in this exemplary configuration, are biased to extend outwardly, upon moving sleeve 26 in a proximal direction, struts 24 extend outwardly to release dilation assembly 40 and stent 42.

Sleeve 26 can be fabricated from various types of materials so long as sleeve 26 is capable of securely retaining struts 24. For instance, sleeve 26 can be fabricated from heat shrink synthetic material, including but not limited to, low-density polyethylene (LDPE), polyethylene terphthalate (PET), Polytetrafluoroethylene (PTFE), fluorinated ethylene propylene (FEP), polyethylene (PE), polyurethane (PU), silicone tubing, and other suitable polymers or synthetic materials.

Actuating member 28 extends from sleeve 26, travels along an exterior of guide member 12, and passes through an aperture 30 in guide member 12. Actuating member 28 continues to travel within lumen 18 of guide member 12 until it reaches proximal end 16 of guide member 12. It will be appreciated that in other embodiments, actuating member 28 may remain external to lumen 18 of guide member 12.

Actuating member 28 can be fabricated from various materials and have various configurations so long as it is capable of performing the function of displacing sleeve 26. For example, actuating member 28 can be fabricated from plastics, polymers, metals, composites, alloys, synthetic materials, and combinations thereof.

As shown in FIG. 2, dilation assembly 40 includes a dilation balloon 46 mounted to a dilation tube 44. Dilation tube 44 extends from distal end 14 of guide member 12 toward proximal end 16 of guide member 12. Dilation tube 44 can include a plurality of holes 50. Each hole 50 and/or plurality of holes 50 in combination provide a fluid path to an interior 52 of dilation balloon 46. In this way, fluid may pass along a lumen 54 of dilation tube 44 to flow into dilation balloon 46. To restrict the flow of such fluid, atraumatic tip 48 seals the distal end of dilation tube 44. In addition to providing a fluid path to inflate dilation balloon 46, holes 50 provide a fluid path to deflate dilation balloon 46 or remove the fluid to deflate dilation balloon 46. Each hole 50 can have various configurations so long as each hole 50 is capable of allowing fluid to pass therethrough.

Dilation tube 44, in one configuration, is an internal support for dilation balloon 46 and stent 42. Dilation tube 44 can be fabricated from Nitinol, steel, metals, metal alloys, composites, plastic, and combinations thereof. Further, dilation tube 44 can be covered with a variety of different coatings, such as, but not limited to, one or more coatings to improve lubricity, anti-thrombogenic properties, and reduce platelet aggregation. Other coatings can include, but not limited to, hydrophilic coatings, heparinized coatings, Polytetrafluoroethylene (PTFE) coating, silicone coating, or combinations of the coatings described herein.

Dilation tube 44 may have a variety of different configurations and embodiments. In another embodiment, dilation tube 44 includes a proximal end where provision is made for connecting dilation tube 44 to an inflation device with an annular clamping device, such as a touhy-borst adaptor. Alternatively, as shown in FIG. 1, a proximal end of dilation tube 44 has the form of a luer fitting, whether the male or female part of the luer fitting.

Mounted to a distal end of dilation tube 44 is an atraumatic tip 48. Atraumatic tip 48 is disposed within lumen 54 of dilation tube 44 and seals dilation tube 44, prevents fluid from escaping therefrom during inflation and deflation of dilation balloon 46, and provides a flexible tip that aids in positioning and steering of delivery device 10 through the tortuous anatomy of the patient. In the illustrative embodiment, dilation tube 44 extends to a distal end of dilation balloon 46 and atraumatic tip 48 is disposed therein. Alternatively, dilation tube 44 can extend to a position proximal to the distal end of dilation balloon 46 and a portion of atraumatic tip 48 then extends from a distal end of dilation tube 44 to a position distal to the distal end of dilation balloon 46. Furthermore, in another alternate embodiment, dilation tube 44 terminates within a lumen formed in atraumatic tip 48.

Atraumatic tip 48 includes a core 56 that is surrounded by a flexible coil 58. As shown, flexible coil 58 terminates at a distal end of tip 48 with an atraumatic portion, such as a solder ball or other mechanism for forming an atraumatic distal end of tip 48. More generally, atraumatic tip 48 can have a variety of other configurations so long as atraumatic tip is flexible and optionally shapeable. Furthermore, atraumatic tip 48 may be radiopaque to allow steerable positioning of delivery device 10 while allowing a physician or clinician to observe the location of tip 48 using appropriate devices, such as a fluoroscopic device or X-ray device. Materials that facilitate or provide radiopacity may include, but not limited to, platinum, alloys of platinum, gold, or combinations thereof, metals, alloys, plastic, polymer, synthetic material, combinations thereof, or other materials that provide an appropriate radiopaque signature, while capable of being shaped by a physician or clinician. Alternatively, tip 48 can be a polymer that is dipped or coated with an appropriate radiopaque material, such as, but not limited to, barium sulphate, bismuth subcarbonate, titanium dioxide, or combinations thereof.

Figure 3:
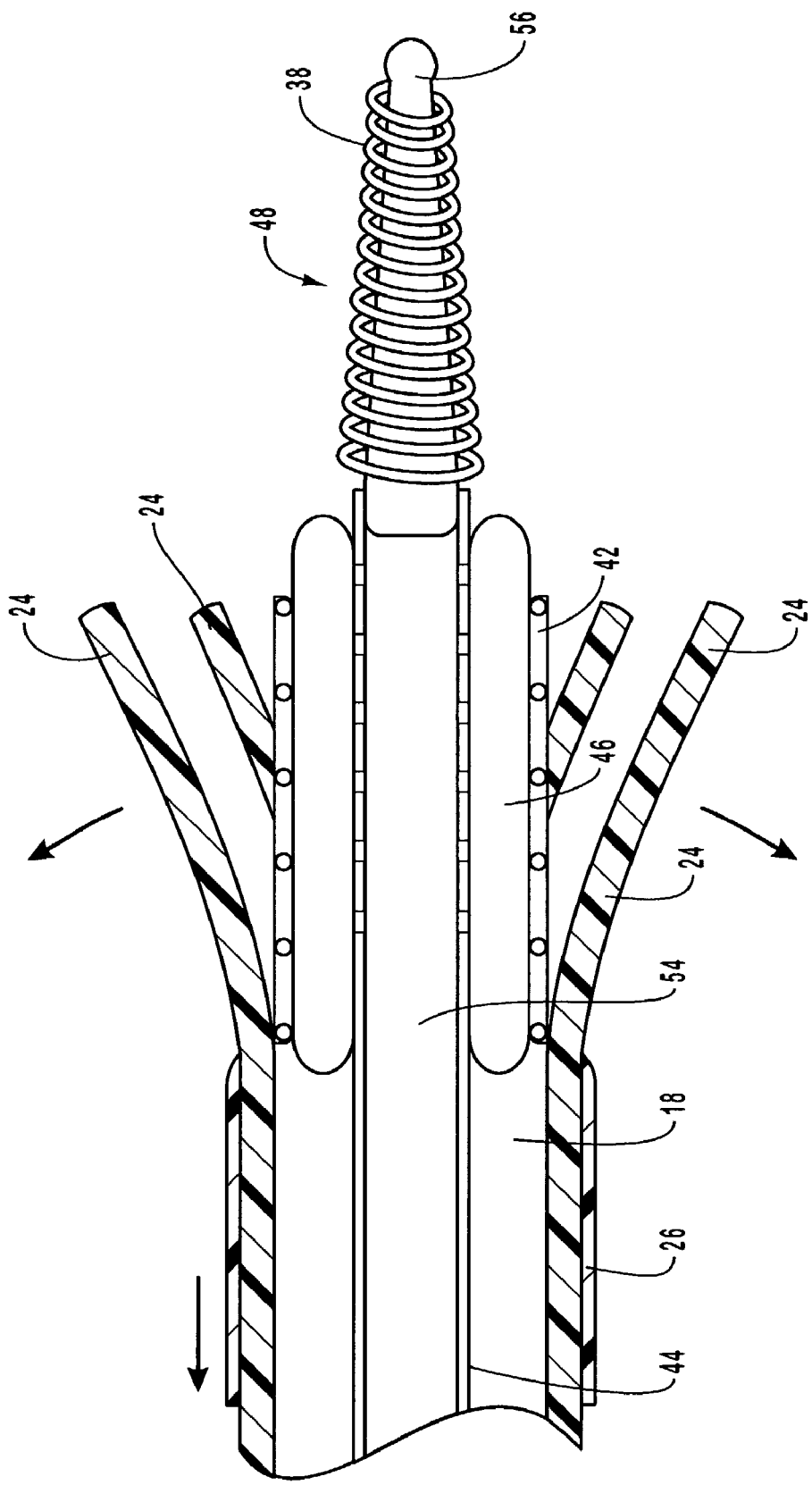
FIG. 3 illustrates a sectional side view of the distal end of the device of FIG. 1 with a distal end in an unrestrained configuration.

Referring now to FIG. 3, depicted is distal end 14 of delivery device 10 upon disposition of sleeve 26 in a proximal direction. In this illustrative configuration, because struts 24 are biased to extend outwardly, dilation assembly 40 and stent 42 can be deployed from within lumen 18. Deploying of dilation assembly 40 and stent 42 can occur as guide member 12 is displaced in a proximal direction, dilation tube 44 is displaced in a distal direction, or a combination of proximal and distal movements of guide member 12 and dilation tube 44 respectively.

Figure 4A:
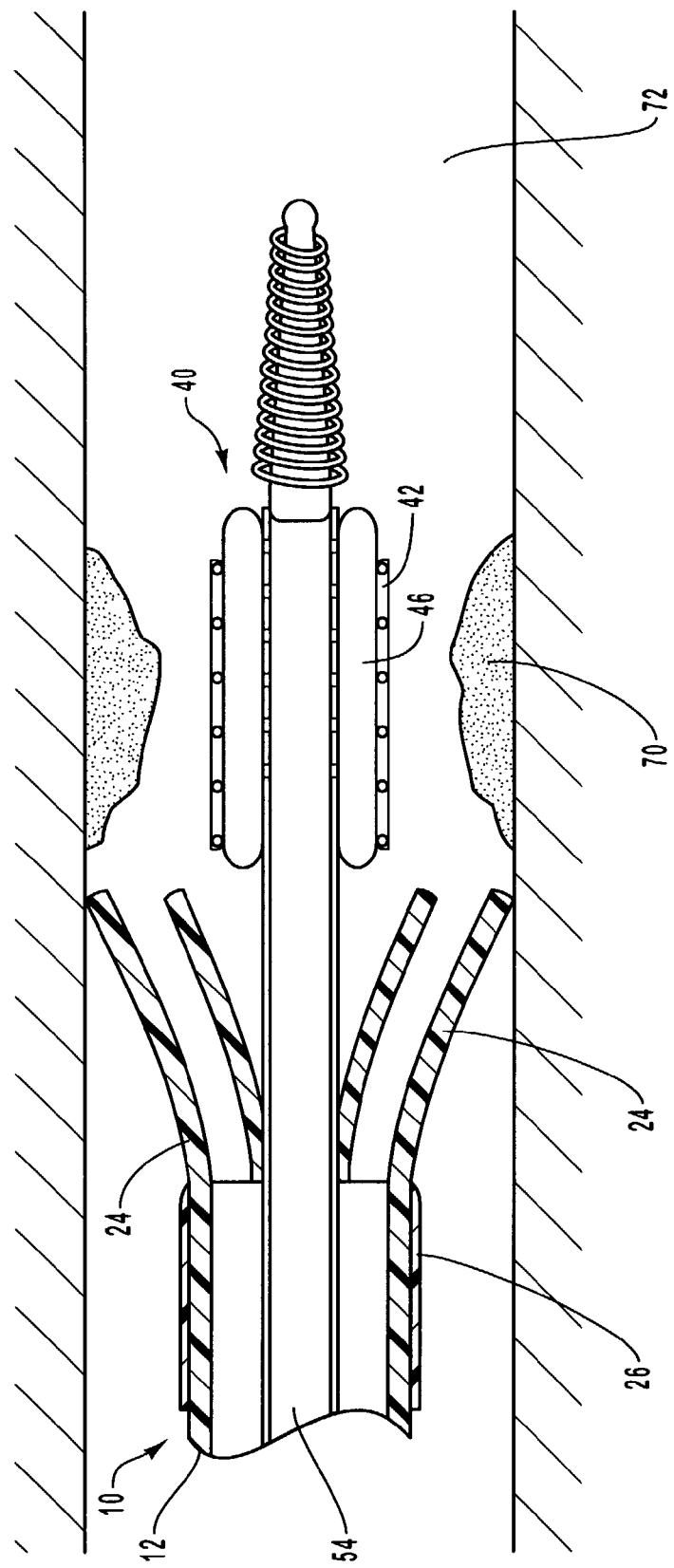
FIGS. 4a and 4b illustrate a sectional side view of the distal end of the device of FIG. 1 with a deployed dilation assembly.
Figure 5:
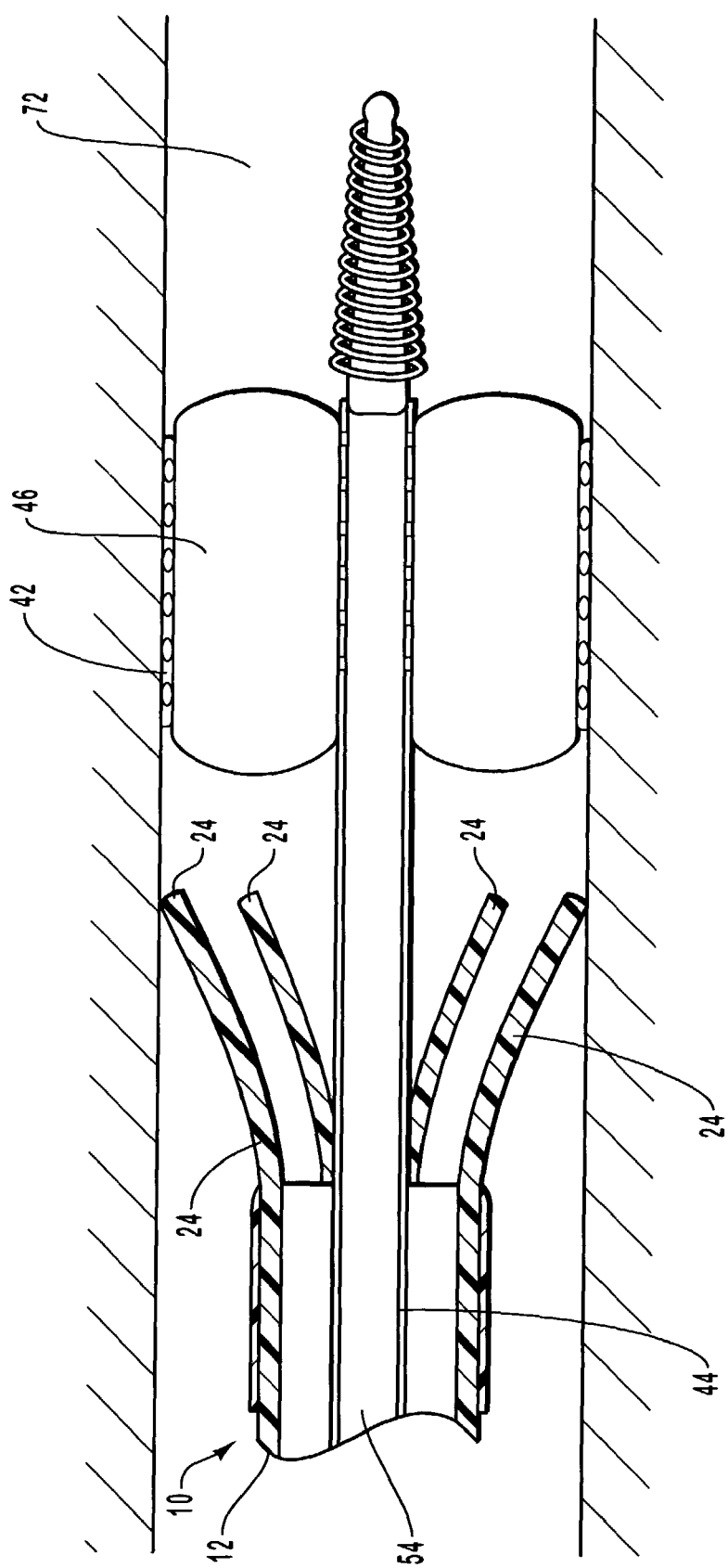
FIG. 5 illustrates a sectional side view of the distal end of the device of FIG. 1 with associated inflated dilation balloon and implanted stent.

Referring now to FIG. 4a, schematically depicted is delivery device 10 in a deployed configuration where dilation assembly 40 and stent 42 have been deployed at a lesion 70 of a body lumen 72. Deployment of dilation assembly 40 and stent 42 can be achieved through manipulating actuating assembly 20 (FIGS. 1 and 2). Upon positioning dilation balloon 46 and stent 42 to the desired position, such as adjacent to lesion 70, fluid can be introduced through lumen 54 of dilation tube 44 to expand dilation balloon 46 and therefore deploy or force stent 42 into body lumen 72 and surrounding lesion 70, as is illustrated in FIG. 5.

Figure 4B:
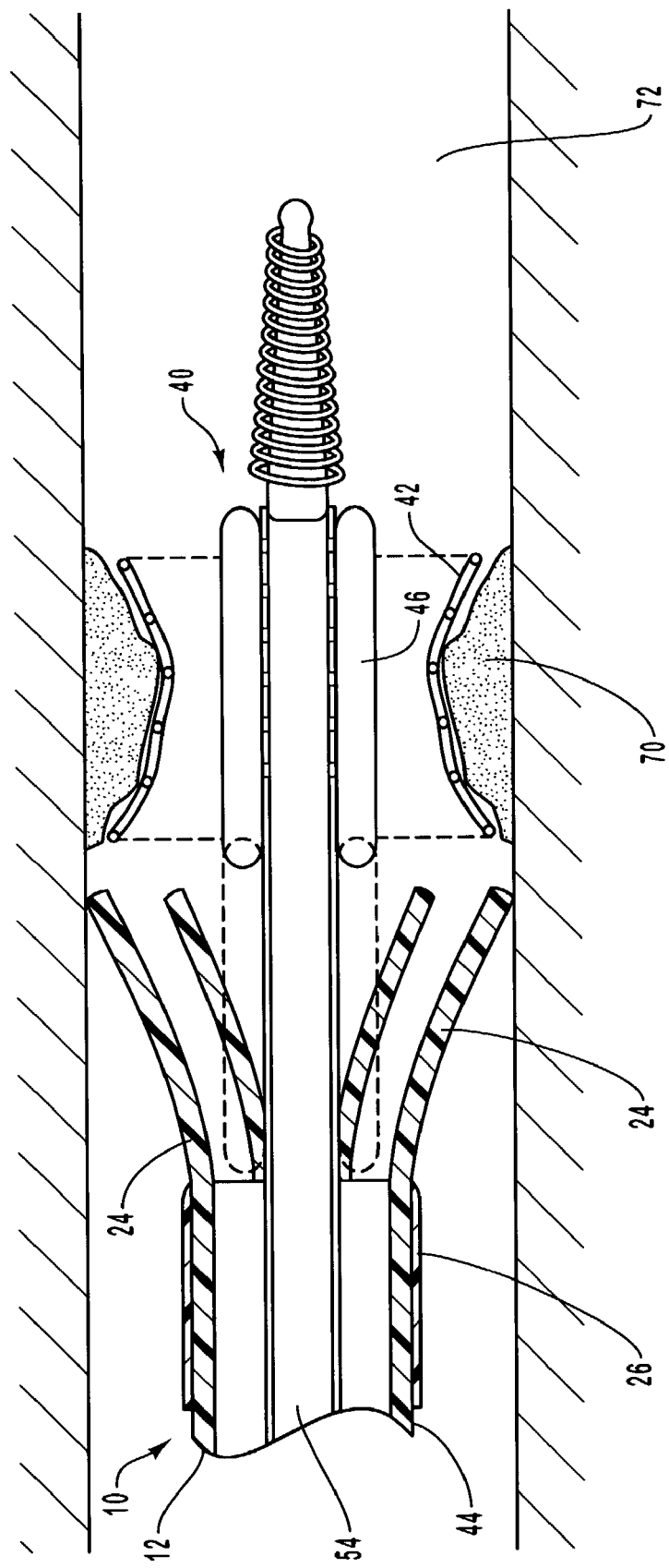

Various configurations of stent 42 are known to those skilled in the art. For example, an expandable stent may be used that automatically opens under the pressure of dilation balloon 46. In another configuration, a self-expanding stent can be used, as illustrated in FIG. 4b with dotted lines. The self-expanding stent automatically opens as the restraining force applied by struts 24 and/or restraining member 25 is removed and guide member 12 is moved proximal to the stent. In this case, the self-expanding stent surrounds dilation balloon 46, as illustrated in FIG. 4b, or alternatively, the stent can surround dilation tube 44 with dilation balloon 46 being located proximal to the stent and still mounted to dilation tube 44, as illustrated by dotted lines referenced by numeral 46b. Various stents may be used with the present invention, so long as the stent can be reduced in size to surround the dilation balloon and be disposed within guide member 12 of delivery device 10.

Figure 6:
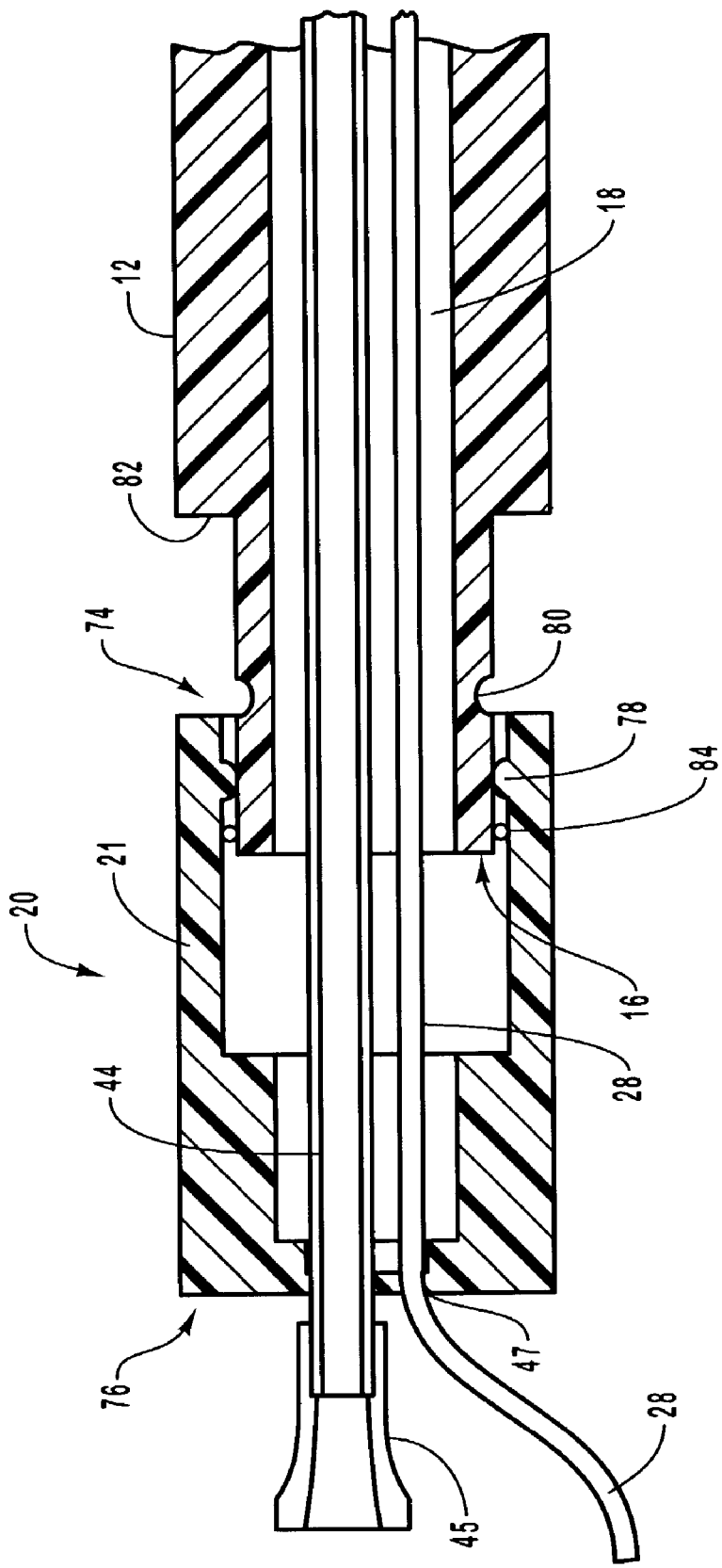
FIG. 6 illustrates a sectional side view of an exemplary proximal end of the device of FIG. 1 in accordance with another aspect of the present invention.

Referring now to FIG. 6, depicted is an exemplary embodiment of actuating assembly 20 that can be used to deploy dilation balloon 46 and stent 42. Operating actuating assembly 20 releases dilation assembly 40 and stent 42 from a restrained configuration at distal end 14 of guide member 12. More specifically, dilation balloon 46 forming part of dilation assembly 40 can be deployed with stent 42 being disposed substantially around dilation balloon 46.

As illustrated, actuating assembly 20 includes an actuating element 21 coupled to a proximal end of dilation tube 44. Actuating element 21 includes a distal end 74 configured to be mounted to and cooperate with proximal end 16 of guide member 12. A proximal end 76 of actuating element 21 is attached to a proximal end of dilation tube 44, while a proximal end of actuating member 28 passes through a sealed aperture 47 of actuating element 21. In this exemplary embodiment, the proximal end of dilation tube 44 includes a luer fitting 45 that allows various complementary luer fittings to be attached thereto. For instance, a syringe (not shown) can be attached to luer fitting 45 for introducing fluid to and removing fluid from dilation balloon 46 (FIG. 5) during inflation and deflation of dilation balloon 46. Although reference is made to use of luer fitting 45, it can be understood by one skilled in the art that various other configurations of fitting can be attached to or formed at the proximal end of dilation tube 44.

Actuating element 21 is adapted to be displaced in a distal direction to deploy dilation assembly 40 and stent 42. To aid with positioning actuating element 21, distal end 74 can have a step configuration and include protrusions 78 that mate with complementary indentations 80 formed in proximal end 16 of guide member 12. The protrusions 78 and indentations 80 provide an indication of the relative position of dilation assembly 40 and stent 42 relative to distal end 14 of guide member 12. Therefore, actuating element 21 and/or guide member 12 can include one or more protrusions and indentations. As actuating element 21 is displaced in a distal direction, protrusions 78 mate with indentations 80. To seal lumen 18 of guide member 12, one or more seals 84 surround protrusions 78. Additionally, one or more seals (not shown) can surround dilation tube 44 and/or actuating member 28. Illustratively, each seal can be one or more O-rings in one or more grooves, one or more O-rings, a gasket, or a viscous fluid seal.

When actuating element 21 is displaced in the distal direction, distal end 74 contacts a wall or stop 82 formed in guide member 12 that prevents further displacement of actuating element 21 in the distal direction. Through this configuration, actuating element 21 is prevented from excessive longitudinal displacement in the distal direction. This stopping of the longitudinal displacement of actuating element 21 indicates that dilation balloon 46 and stent 42 are deployed from within lumen 18 of guide member 12 to the desired position for expanding or implanting stent 42.

Although reference is made to one manner of indicating the particular location of stent 42, one skilled in the art can identify a variety of different embodiments. For instance, a plurality of indentations and/or protrusions can be included within actuating element 21 and guide member 12 to control the distance which actuating element 21 and, consequently, stent 42 is displaced. In another configuration, a wall or stop formed in actuating element 21 can mate with the distal end of guide member 12 to prevent excessive longitudinal displacement in the distal direction. In still another configuration, a combination of one or more walls or stops in actuating element 21 and guide member 12 can be used. In still another configuration, distal end 74 of actuating element 21 can be tapered and cooperate with a taper formed in proximal end 16 of guide member 12. The complementary tapers control the longitudinal displacement of actuating element 21 relative to proximal end 16 of guide member 12. In still other configurations, a combination of indentations, protrusions, walls, stops, threads, or tapers can be used. Various other manners are known to control the distance traveled by actuating element 21 while indicating the position of stent 42.

In addition to the above, it can be appreciated that actuating element 21 can include one or more elements, such that wall or stop 82 and indentations 80 are formed in separate elements or members that are attached or coupled to proximal end 16 of guide member 12. By so doing, actuating element 21 can be fabricated separately from guide member 12, thereby reducing costs and expenses associated with fabricating proximal end 16 of guide member 12 in the desired configuration.

FIGS. 7 through 24 illustrate alternative embodiments for restraining mechanism 25. It will be appreciated that many features of the delivery devices depicted in FIGS. 7 through 24 are substantially similar in structure and function as for delivery device 10. Consequently, features and functions of one embodiment of the present invention are applicable to other embodiments of the present invention.

Referring now to FIGS. 7 and 8, another illustrative embodiment of a delivery device 100 of the present invention is depicted. As shown, a guide member 112, which can be similar to the other guide members described herein, has a distal end 114, a proximal end (not shown), and a lumen 118 extending from distal end 114 to the proximal end. A tip 115 of guide member 112 includes a plurality of struts 124, such as two or more struts. Each strut 124 can be optionally biased so that a distal end of each strut 124 moves outwardly from a longitudinal axis of guide member 112 when each strut 124 is released by a restraining member 125. Although reference is made to each strut 124 being biased, one skilled in the art can appreciate that one or more of struts 124 can be biased.

As shown in FIG. 8, at least one strut, designated by reference numeral 124a, is biased toward the longitudinal axis of guide member 112. Disposed upon strut 124a, as more clearly seen in FIG. 7, is an atraumatic tip 148. This atraumatic tip 148, either alone or in combination with strut 124a, may be shapeable by a physician or clinician before insertion into a body lumen. In this manner, the physician or clinician is able to configure tip 148 with an appropriate shape, such as, but not limited to a "J" shape, which enables guide member 112 to be guided through the tortuous anatomy of a patient. All or a portion of atraumatic tip 148 can be fabricated from platinum, platinum alloys, radiopaque materials, materials doped or coated with a radiopaque material, metals, alloys, plastic, polymer, synthetic material, combinations thereof, or other materials that provide an appropriate radiopaque signature, while are capable of being shaped, whether alone or in combination with strut 124a, by a physician or clinician. In this configuration, a guidewire with an associated dilation assembly can be disposed within lumen 118, with a distal end of the guidewire optionally including a flexible atraumatic tip, since atraumatic tip 148 can function as the atraumatic tip for delivery device 100.

To maintain struts 124 in a restrained position, i.e., not extending outwardly from guide member 112, restraining member 125 surrounds struts 124. The restraining member 125 and other restraining members or mechanisms described herein are examples of means for applying a restraining force upon one or more struts or means for applying a restraining force upon a distal end of a guide member. In this embodiment, restraining member 125 can extend completely or partially from the distal end to the proximal end of guide member 112. For example, restraining member 125 can surround substantially only struts 124 or can have a configuration similar to those depicted in FIGS. 9-24.

In the configuration depicted in FIGS. 7 and 8, restraining member 125 or means for applying a restraining force is a catheter 127 that applies a force against struts 124 to prevent struts 124 from extending outwardly or applies a force against struts 124 to maintain a dilation assembly 140 and a stent 142 in lumen 118. Through displacing guide member 112 with respect to catheter 127, or vice versa, the force applied to struts 124 is released and, in one configuration, the distal ends of struts 124 are allowed to move outwardly to allow dilation assembly 140 and stent 142 to be deployed.

As mentioned above, catheter 127 can extend completely or partially the length of the guide member. In another configuration, catheter 127 can be replaced with a sleeve or other structure that completely or partially extends toward the proximal end of guide member 112 from the distal end. These alternate configurations are also means for applying a restraining force, as described herein. These restraining members or mechanisms can be radiopaque or include one or more radiopaque markers that aid with positioning the device. Furthermore, these restraining members or mechanisms can be slidable relative to the guide member using an actuating member and/or an actuating assembly disposed on an exterior of the guide member, within a lumen of the guide member, or partially within the lumen and partially on the exterior of the guide member. The actuating assembly may be similar in structure and function to actuating assembly 20 described in FIG. 6 or any other actuating assembly described herein. Therefore, systems, methods, and devices of the present invention can optionally use catheters, sleeves, bands, or other structures described herein interchangeably to perform the desired function of restraining one or more struts or a distal end of the guide member.

FIGS. 9 and 10 depict another embodiment of a delivery device 200 of the present invention. As illustrated, delivery device 200 includes a guide member 212 with a plurality of struts 224 disposed at a distal end 214 thereof. Struts 224 are maintained in a restrained position using a restraining member 225. In this embodiment, restraining member 225 is a sleeve 226 surrounding struts 224. Sleeve 226 acts as a restraining member or mechanism that applies a force against the struts to prevent the struts from extending outwardly or to maintain the dilation balloon and/or stent within the lumen.

Struts 224, when in a restrained position, maintain dilation assembly 240 and stent 242 within lumen 218 of guide member 212. Disposed within sleeve 226 or between sleeve 226 and guide member 212 are one or more actuating members 228. Actuating members 228, optionally forming part of the restraining mechanism or member, are attached to guide member 212 at a location proximal to the proximal end of each strut 224, identified by letter A. Actuating members 228 extend distally to the distal end of sleeve 226 and subsequently extend proximally on the outside of sleeve 226 to terminate at the proximal end (not shown) of device 200. Since one end of each actuating member 228 is located at the proximal end of sleeve 226, whether forming part of sleeve 226, attached to sleeve 226, attached to guide member 212, or combinations thereof, displacing actuating member 228 in the proximal direction causes actuating member 228 to preferentially separate sleeve 226 into one or more portions 232, illustrated in dotted lines. By so doing, struts 224 are released, as illustrated in FIG. 10.

To operate actuating members 228, a proximal end (not shown) of actuating member 228 extends to a proximal end (not shown) of guide member 212, either within or without lumen 218 of guide member 212. Actuating members 228 can extend to an actuating element (not shown) of an actuating assembly, such as, but not limited to, the actuating assembly of FIG. 6 and other actuating assemblies described herein and understood by one skilled in the art in light of the teachings contained herein. The actuating member 228 can be displaced in the proximal direction relative to guide member 212. By so doing, the restraining force applied by sleeve 226 is released, struts 224 extend outwardly, and dilation assembly 240 and/or stent 242 are deployed.

Sleeve 226 can be formed from a variety of different materials, so long as the material is sufficiently strong to secure struts 224, while being configured to preferentially separate under the action of actuating members 228. For example, sleeve 226 can be fabricated from heat shrink synthetic material, including but not limited to, low-density polyethylene (LDPE), polyethylene terphthalate (PET), Polytetrafluoroethylene (PTFE), fluorinated ethylene propylene (FEP), polyethylene (PE), polyurethane (PU), or silicone tubing.

The one or more actuating members 228 can be formed from a variety of different materials, so long as the material used is sufficiently strong to allow an actuating assembly, such as, but not limited to, those actuating assemblies disclosed herein, to displace actuating member 228 proximally without breaking the same. For example, actuating members 228 can be fabricated from plastics, polymers, metals, composites, alloys, synthetic materials, and combinations thereof.

Instead of using actuating members 228, embodiments of the present invention can employ various other means to preferentially separate sleeve 226. For example, sleeve 226 can have dissolvable chemical bonds which dissolve due to a chemical reaction with the fluid in the body lumen within which the delivery device is disposed, bonds that are broken through applying resistive heating, ultrasonic, or radio frequency energy to actuating members 228 and/or region of the body lumen containing device 200, preferential tear or cut regions or zones where the material has a weaker strength than other regions or zones of the sleeve, or combinations thereof.

Referring now to FIGS. 11 through 14, depicted is an embodiment of a delivery device 300 having another embodiment of a restraining member or mechanism 325. In this embodiment, restraining member 325 is in the form of a sleeve 326 which is adapted to surround one or more struts 324 of a guide member 312 and apply a restraining force against struts 324 to maintain struts 324 in a restrained configuration. Sleeve 326 includes a first side 364 and a second side 366 with first and second sides 364, 366 being separated by an intermediate portion 368. Intermediate portion 368 surrounds guide member 312 in such a manner that portions of intermediate portion 368 contact, are juxtaposed to, are contiguous with, or are adjacent to one another. An actuating member 328 passes through such portions of intermediate portion 368 to secure sleeve 326 upon guide member 312. To further aid with applying a restraining force against struts 324, first side 364 and second side 366 are folded to attach to respective portions of outside surface of sleeve 326.

Figure 13:
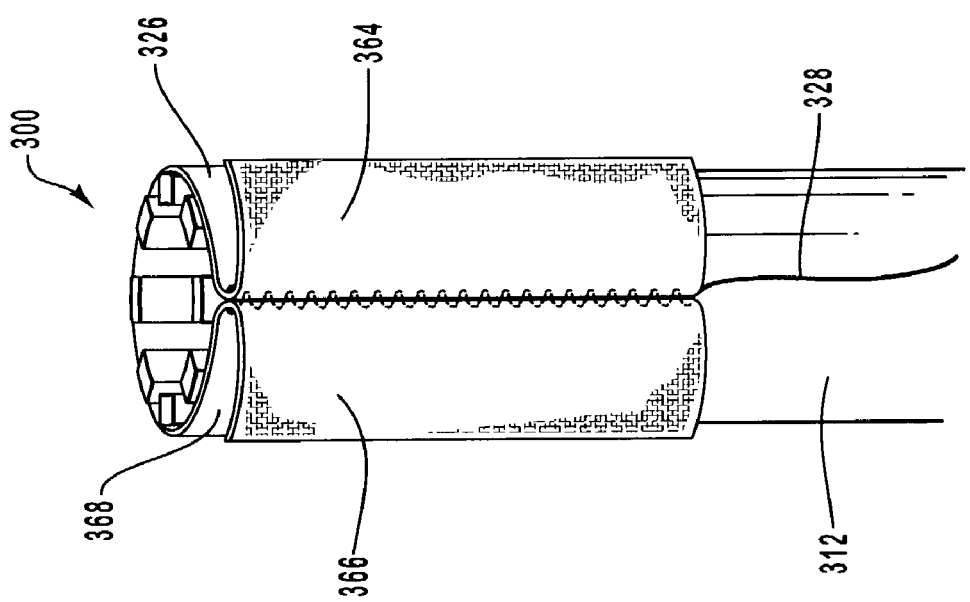
FIG. 13 illustrates a perspective view of the distal end of the delivery device of FIG. 11, illustrating the restraining member partially coupled to the delivery device.

The process of forming the restraining member or mechanism of FIG. 11 is illustrated in FIGS. 12 and 13. With reference first to FIG. 12, which depicts sleeve 326 in an open position before actuating member 328 is coupled thereto, sleeve 326 can be directly formed on guide member 312 or can be formed on a separate tubular member and subsequently attached or coupled to guide member 312. Sleeve 326 is illustrated as having a generally polygonal configuration, however, one skilled in the art can appreciate that sleeve 326 can have various other configurations so long as it is capable of performing the functions described herein. In this exemplary configuration, sleeve 326 is coupled directly to guide member 312. First side 364 and second side 366 of sleeve 326 are wrapped around at least a portion of guide member 326, until a portion of intermediate portion 368 is in close proximity with another portion of intermediate portion 368, as illustrated in FIG. 13. Alternatively, a first side 364 can contact second side 366 or be juxtaposed, contiguous, or adjacent to second side 366.

When the portions of intermediate portion 368 are in close proximity, actuating member 328, or alternatively some other actuating member, is stitched through both portions of sleeve 326 to couple the portions of intermediate portion 368, as shown in FIG. 13. Once actuating member 328 is drawn substantially straight or otherwise positioned through sleeve 326, first end 364 and second end 366 are respectively folded to attach to respective outside surfaces of sleeve 326, as shown in FIG. 11.

Figure 14:
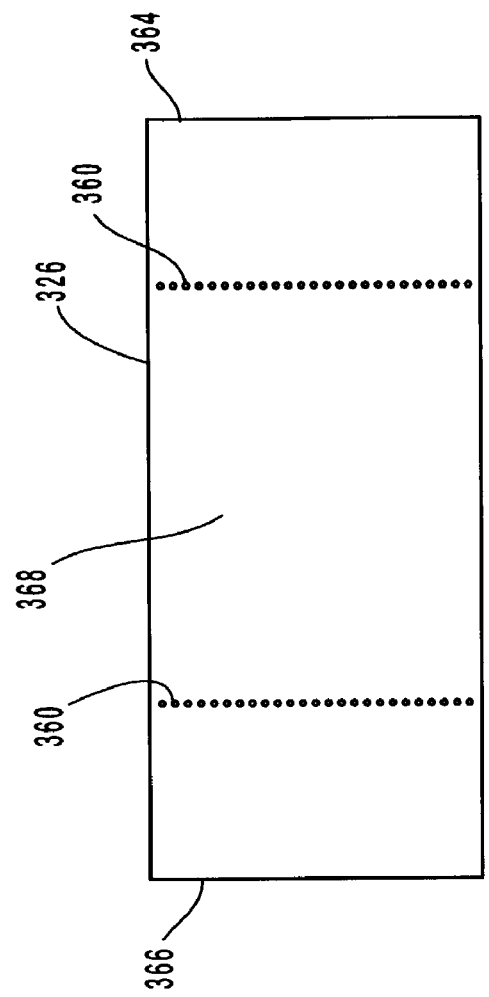
FIG. 14 illustrates a side view of another restraining mechanism usable with the delivery device of FIG. 11 in accordance with one aspect of the present invention.

As illustrated in FIG. 14, in an alternate configuration, sleeve 326 can include a plurality of apertures 360 on portions of intermediate portion 368 that receive actuating member 328. In this manner, actuating member 328 can pass through apertures 360 rather being stitched through sleeve 326. In another embodiment, first end 364 of sleeve 326 can be coupled to second end 364 of sleeve 326 without attaching first end 364 or second end 366 to the outside surface of sleeve 326. In still another configuration, a portion of first end 364 can overlap a portion of second end 366, or vice versa. Alternatively, first end 364 and second end 366 contact each other but do not overlap. Similarly, first end 364 and second end 366 can be adjacent to one another, adjoining one another, contiguous to one another, or juxtaposed to one another.

To operate the restraining member or mechanism described in reference to FIGS. 11-14, a proximal end of actuating member 328 extends to a proximal end of guide member 312, either within or without a lumen of the guide member 312. Upon displacing actuating member 328 in a proximal direction relative to guide member 312, vice versa, or combination thereof, actuating member 328 is released from being disposed through at least a portion of sleeve 326. By so doing, the restraining force applied by sleeve 326 is released, struts 324 extend outwardly, and the dilation assembly and/or stent are deployed. A clinician or physician can initiate the longitudinal motion of actuating member 328, either directly or through using of an actuating mechanism or device.

Sleeve 326 can be formed from a variety of different materials, so long as the material is sufficiently strong to restrain one or more struts 324. For example, sleeve 326 can be fabricated from various types of polymer or silicone films, such as but not limited to, heat shrink plastic, polymer, low-density polyethylene (LDPE), polyethylene terphthalate (PET), Polytetrafluoroethylene (PTFE), fluorinated ethylene propylene (FEP), polyethylene (PE), polyurethane (PU), or silicone tubing.

Actuating member 328 can be formed from a variety of different materials, so long as the material used is sufficiently strong to allow the actuating assemblies disclosed herein to displace actuating member 328 proximally without breaking actuating member 328. For example, actuating member 328 can be fabricated from plastics, polymers, metals, composites, alloys, synthetic materials, combinations thereof, or other material that is capable of performing the function of being disposed through sleeve 326 and capable of being withdrawn therefrom.

Referring now to FIGS. 15-19, illustrated is another embodiment of a delivery device 400 having an alternate configuration of a restraining member or mechanism. This particular embodiment utilizes a restraining member or mechanism 425 having a hinged configuration with an actuating member 438, optionally forming part of restraining member or mechanism 425, acting as the pin to maintain the hinged portions of the restraining member in a configuration that retains or restrains a portion of the guide member.

Figure 15:
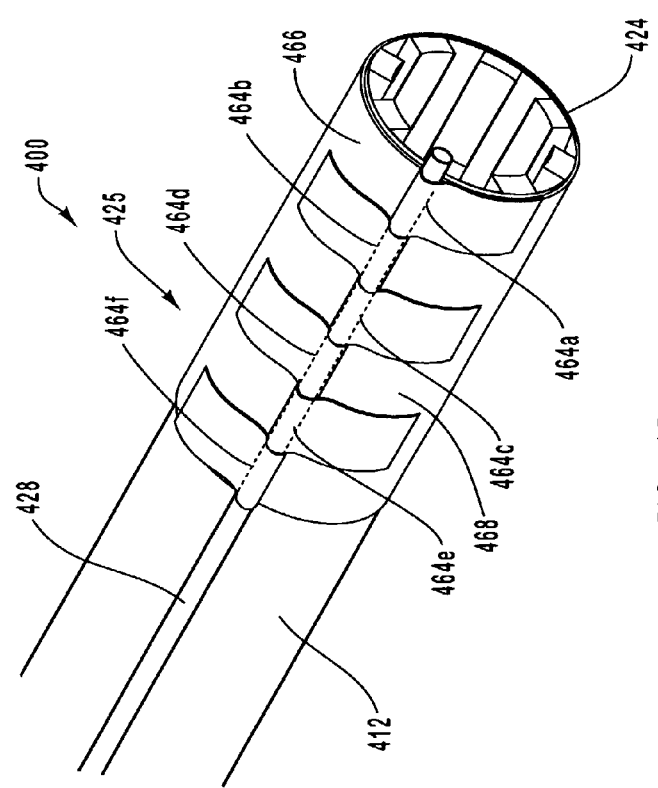
FIG. 15 illustrates a perspective view of another embodiment of the stent delivery device in accordance with one aspect of the present invention.

As shown in FIG. 15, restraining member 425 is a sleeve 426 having a plurality of channels 464a-464f that are adapted to receive actuating member 428. Both a first side 466 and a second side 468 of sleeve 426 are formed with some of channels 464a-464f, i.e., channels 464a, 464c, and 464e on first side 466 and channels 464b, 464d, and 464f on second side 468. By passing actuating member 428 through channels 464a-464f in sequential order, so that actuating member 428 passes through a channel on first side 466 and subsequently a channel on second side 468, first side 466 is coupled to second side 468 and sleeve 426 applies a restraining force against struts 424 of guide member 412.

Figure 16:
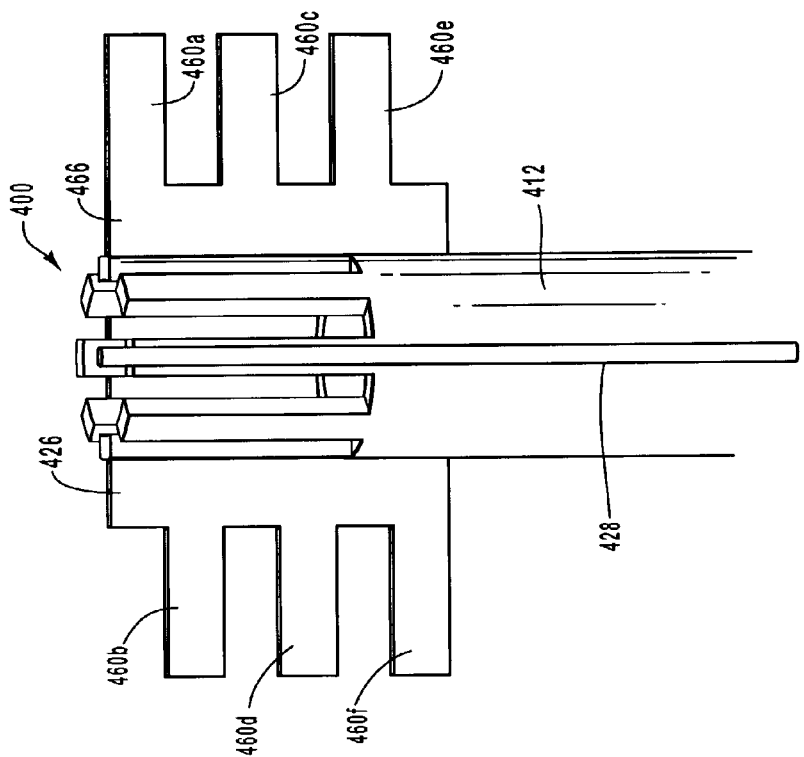
FIG. 16 illustrates a perspective view of the distal end of the delivery device of FIG. 15 before a restraining mechanism is coupled to the delivery device.

An exemplary process of forming the restraining member or mechanism of FIG. 15 is illustrated in FIGS. 16-19. With reference first to FIG. 16, which depicts sleeve 426 in an open position before actuating member 428 is coupled thereto, sleeve 426 includes a number of extensions or tongues 460a-460f. These extensions 460a-460f are configured to form channels 464a-464f and surround a tubular member or tube, such as, but not limited to, a guide member 412 within which actuating member 428 is located.

Figure 17:
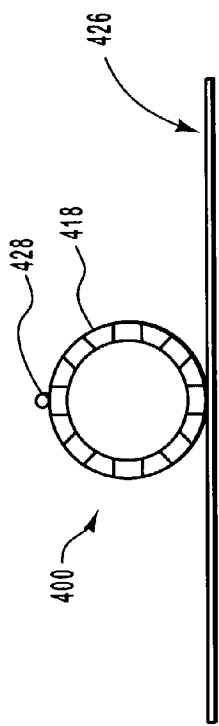
FIG. 17 illustrates a side view of the delivery device of FIG. 15 illustrating the restraining member partially coupled to the delivery device.
Figure 19:
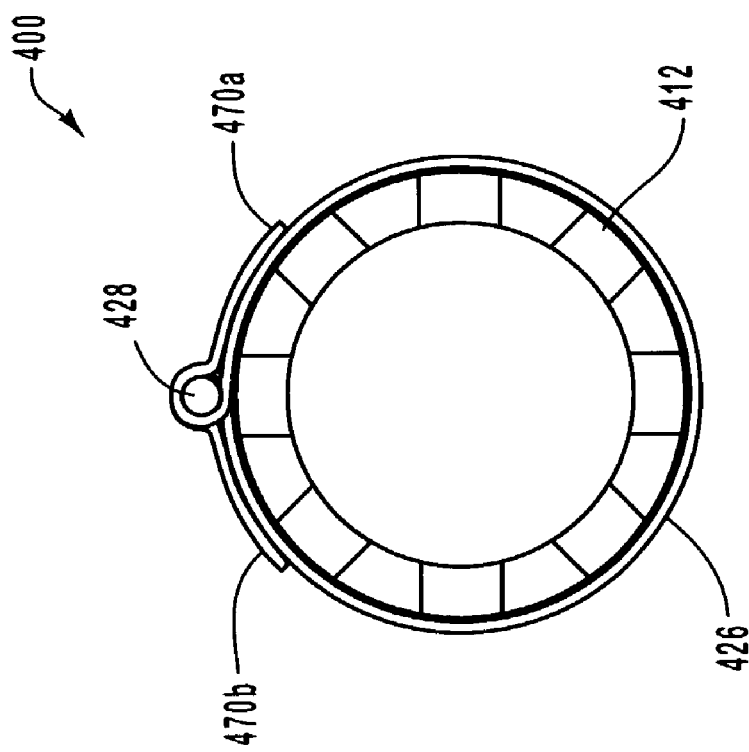
FIG. 19 illustrates a side view of the delivery device of FIG. 15 illustrating the restraining member partially coupled to the delivery device.
Figure 18:
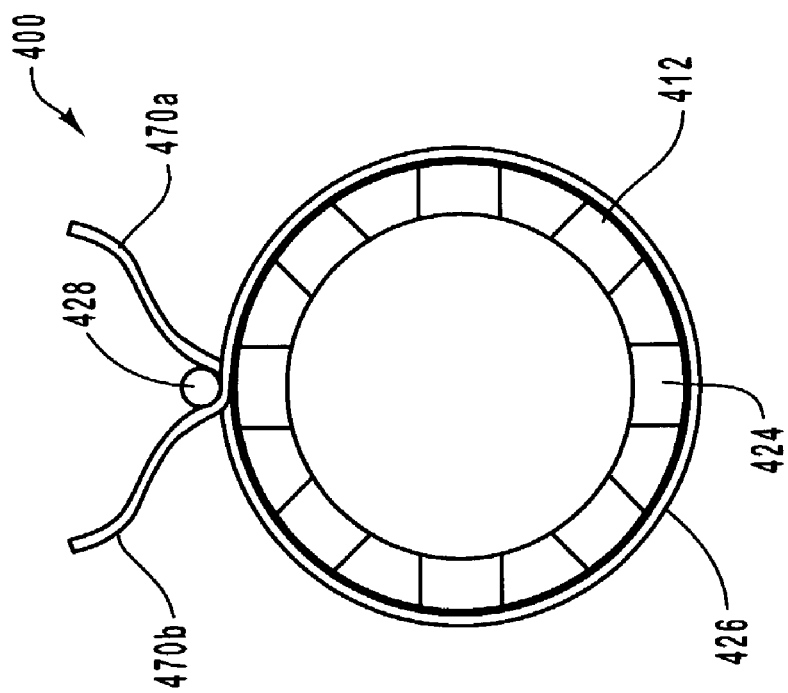
FIG. 18 illustrates a side view of the delivery device of FIG. 15 illustrating the restraining member partially coupled to the delivery device.
Figure 21:
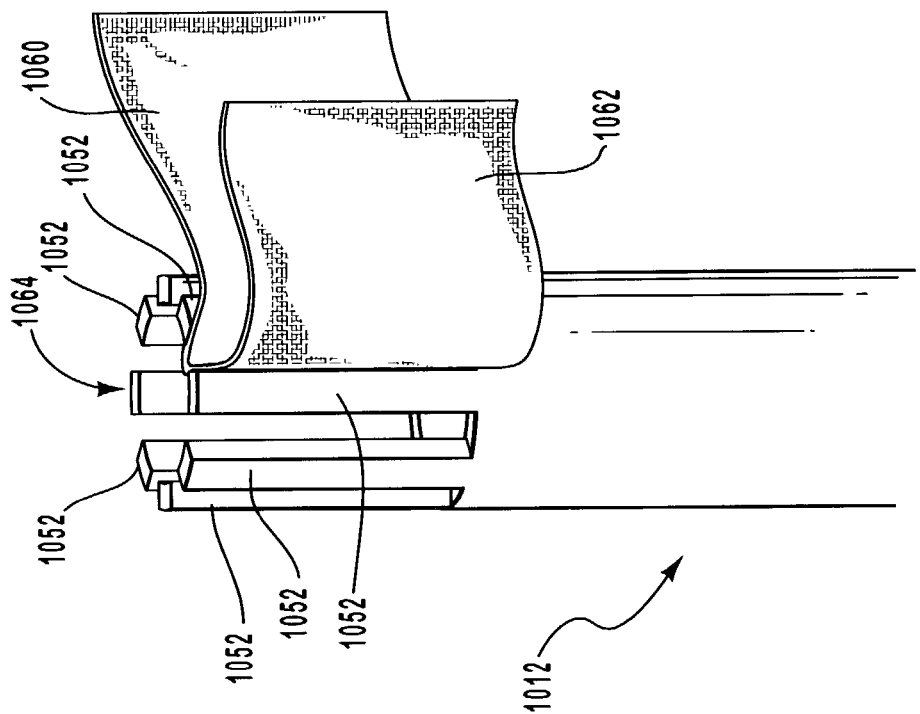
FIG. 21 illustrates a perspective view of another embodiment of a stent delivery device in accordance with another aspect of the present invention.

To attach sleeve 426 to guide member 412, sleeve 426 is positioned over the desired portion of guide member 426. Actuating member 428 is placed in close proximity to guide member 412, as shown in FIGS. 17-19. The ends of the extensions 460a-460f are inserted between guide member 412 and actuating member 428, as shown in FIG. 18. Alternatively, extensions 460a-460f can be partially wrapped around guide member 412 and actuating member 428 placed into contact with these partially wrapped extensions 460a-460f.

After the extensions 460a-460f are pulled tightly around guide member 412 and actuating member 428, an end of each extension 460a-460f is folded over actuating member 428 to attach to the outer surface of sleeve 426, as shown in FIGS. 15 and 19. In this manner, channels 464a-464f are formed and sleeve 426 is configured with actuating member 428 to releasably restrain struts 424 of guide member 412.

Releasing the restraining force applied by sleeve 426, alone or in combination with actuating member 428, is achieved through displacing actuating member 428 longitudinally with respect to guide member 412, vice versa, or combination thereof. Actuating member 428 is released from channels 464a-464f to allow the biasing force of struts 424 to extend the struts outwardly to deploy dilation assembly and/or stent. A clinician or physician can initiate the longitudinal motion of actuating member 428, either directly or through using of an actuating mechanism or device.

Figure 20:
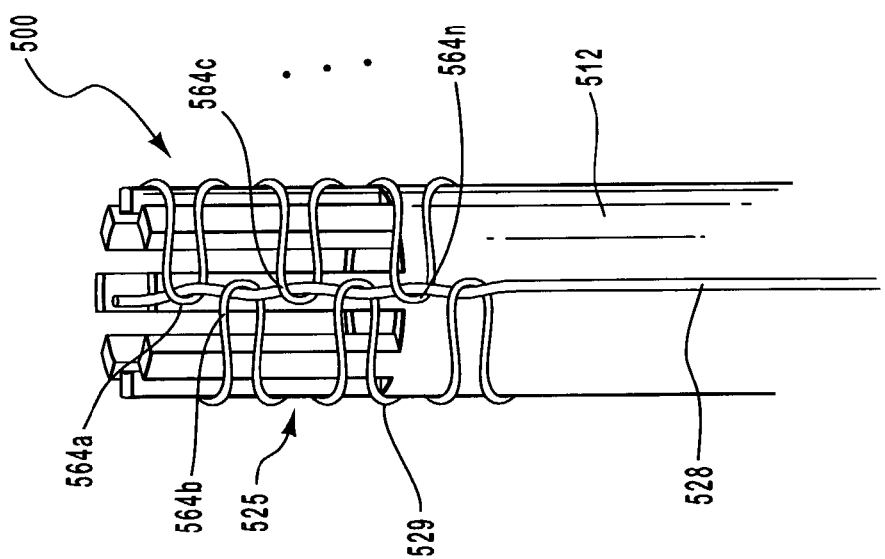
FIG. 20 illustrates a perspective view of another embodiment of a stent delivery device in accordance with another aspect of the present invention.

Referring now to FIG. 20, depicted is another delivery device 500 having another embodiment of a restraining member or mechanism 525 of the present invention. The restraining member 525 includes a cord 529 forming a number of hoops 564a-564n. One or more of hoops 564a-564n are adapted to receive an actuating member 528, which is optionally part of restraining member or mechanism 525. The actuating member 528 is disposed within hoops 564a-564n so that cord 529 applies a restraining force against struts 524 of guide member 512. Actuating member 528 can be removed from hoops 564a-564n to thereby allow struts 524 to extend outwardly to deploy the dilation assembly and/or stent. Cord 529 may be made from metallic wires, polymer actuating members, or other materials that can be manipulated to form hoops through which an actuating or securing member. Optionally, cord 529 is adapted to expand outwardly either under the influence of one or more struts or due to a biasing force applied or incorporated within cord 520 by the configuration and/or material of the cord, the hoops, and/or the restraining member.

Cord 529 can be attached to guide member 512 and/or one or more of the struts associated therewith through various attachment mechanisms. For instance, cord 529 can be attached to guide member and/or one or more of the struts through adhesives, mechanical fasteners, securing loops, or other manner that securely attaches cord 529 to guide member 512 and/or one or more of struts 524. Alternatively, cord 529 may be attached to actuating member 528 and be removed when actuating member 528 is moved in a proximal direction. A clinician or physician can initiate the longitudinal motion of actuating member 528, either directly or through using of an actuating mechanism or device.

Figure 23:
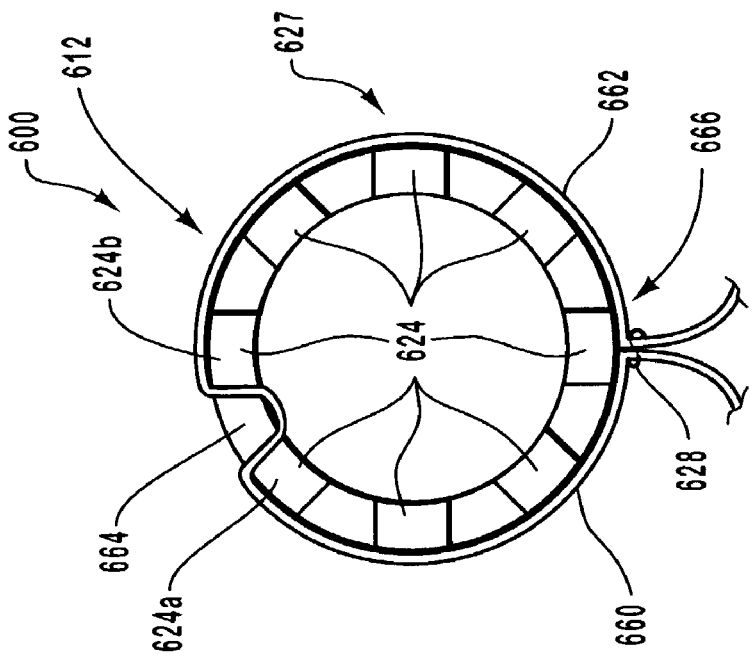
FIG. 23 illustrates a side view of the delivery device of FIG. 21 illustrating the restraining member partially coupled to the delivery device.
Figure 22:
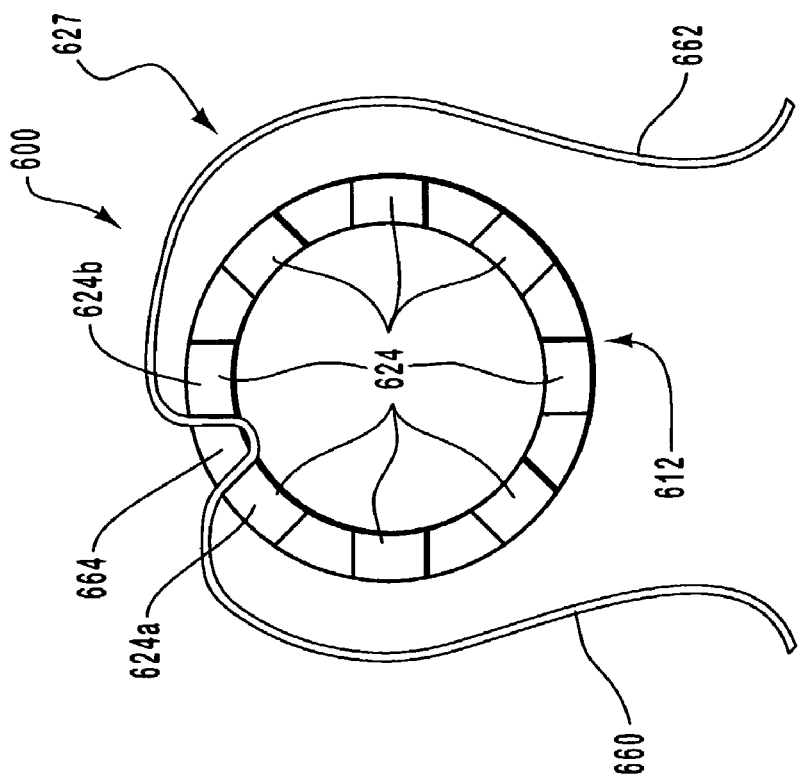
FIG. 22 illustrates a side view of the delivery device of FIG. 21 before the restraining mechanism is coupled to the delivery device.

Referring now to FIGS. 21-24, depicted is another delivery device 600 having another embodiment of a restraining member or mechanism 625 of the present invention. As illustrated, a guide member 612 includes a plurality of struts 624 that are adapted to extend outwardly to enable deployment of the stent and dilation balloon disposed within a lumen 618 of guide member 612. A restraining member 625 restrains struts 624. This restraining member 625, in one configuration, is a flexible member 627 configured with flaps 660 and 662. The flaps 660 and 662 extend between a gap 664 between the two adjacent struts 624a and 624b and are adapted to be pulled around struts 624 to compress stent (not shown) and dilation balloon (not shown) within lumen 618, as illustrated in FIG. 23. These flaps 660 and 662 can be two separate members that are bonded or otherwise connected to struts 624a and 624b or a single member that is coupled to struts 624a and 624b while forming flaps 660 and 662.

When flaps 660 and 662 have been positioned to securely retain struts 624, they are then stitched together at a location 666, identified in FIG. 23, with an actuating member 628. This actuating member 628, optionally forming part of the restraining member or mechanism, extends the length of delivery device 600 toward an actuating assembly, such as, but not limited to, the actuating assembly described in FIG. 6 and other actuating assemblies known to those skilled in the art in light of the teachings contained herein. A clinician or physician can initiate longitudinal motion of actuating member 628 to release restraining member or mechanism 625, either directly or through using of an actuating mechanism or device as known to those skilled in the art.

Figure 24:
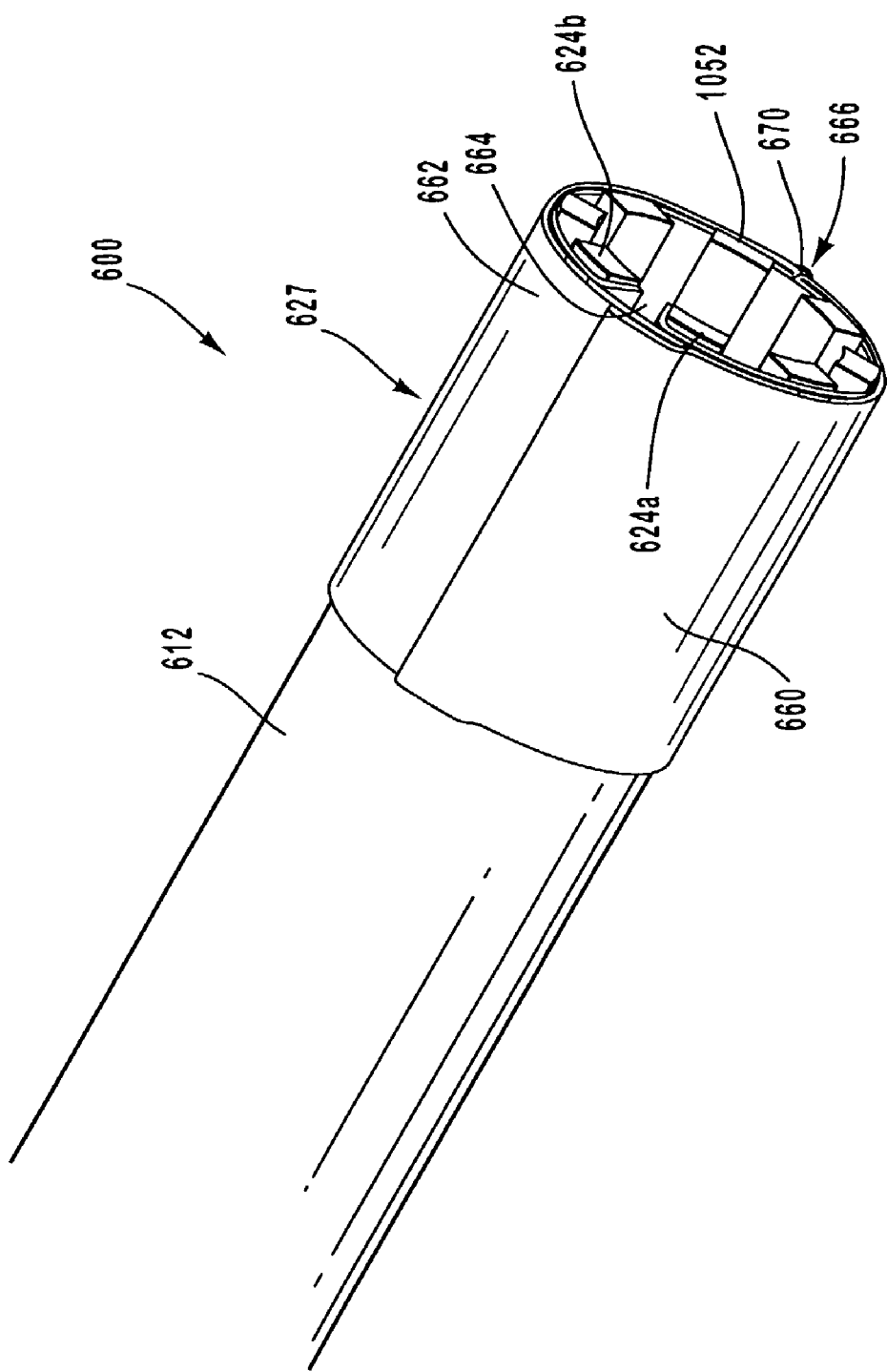
FIG. 24 illustrates a perspective view of the delivery device of FIG. 21 having the restraining mechanism coupled to a distal end thereof.

Following coupling of flaps 660 and 662 using actuating member 628, flaps 660 and 662 are folded back around struts 624 and the remainder of flaps 660 and 662, and then attached to struts 624, or other portion of guide member 612, as illustrated in FIG. 24. When actuating member 628 is displaced in a proximal direction, flaps 660 and 662 are released and stent (not shown) and dilation balloon (not shown) are deployed as struts 624 extend outwardly.

Figure 25:
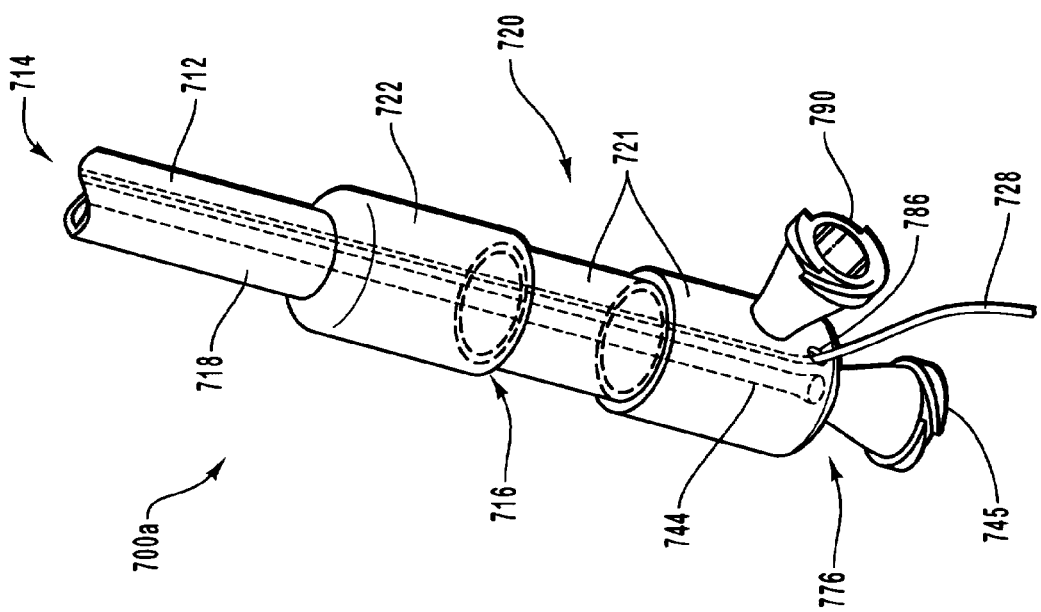
FIG. 25 illustrates a perspective view of a proximal end of another embodiment of a stent delivery device in accordance with another aspect of the present invention.

Referring now to FIG. 25, depicted is an illustrative embodiment of a proximal end of a delivery device 700a. The features and structures discussed with other embodiments of the delivery device of the present invention apply to delivery device 700a.

As shown, a proximal end 716 of a guide member 712 terminates in a guide member housing 722. This guide member housing 722 can be integrally formed with guide member 712 or alternatively be a separate member coupled, connected, or attached to a proximal end of guide member 712. Proximal end 716 of guide member 712 is coupled to an actuating element 721 of an actuating assembly 720. This actuating element 721 slidably engages with guide member housing 722. Manipulation of actuating element 721 effects the movement of dilation tube 744 upon which is mounted the dilation balloon (not shown). Actuating member 728 extends through an aperture 786 in actuating element 721 that is adapted with a seal (not shown) through which actuating member 728 can slide. In this manner, aperture 786 and the seal (not shown) allow access for the operator to release or displace the restraining member (not shown) that restrains the one or more struts (not shown) disposed at distal end 714 of delivery device 700a. The seal can include a polymer gasket, such as, but not limited to, polyurethane, silicone rubber, or other materials that are capable of making a seal around actuating member 728 and allow the actuating member 728 to slide therethrough while a fluid seal is maintained.

A dilation tube 744, optionally having a similar configuration to dilation tube 44 of FIG. 1, extends from a distal end 714 of guide member 712 through guide member housing 722 to terminate and be attached to proximal end 776 of actuating element 721. As depicted, proximal end 776 of actuating element 721 includes a luer fitting 745, which is adapted to cooperate with a complementary luer fitting for inflating and deflating a dilation balloon (not shown) disposed at distal end 714 of guide member 712.

In this illustrative embodiment, an additional luer fitting 790 is formed in or coupled to actuating element 721. Luer fitting 790 is provided to infuse fluid through a lumen 718 of guide member 712, thereby allowing introduction of a contrast media in the blood flow around the vicinity of the device as it is advance in the vasculature.

Figure 26:
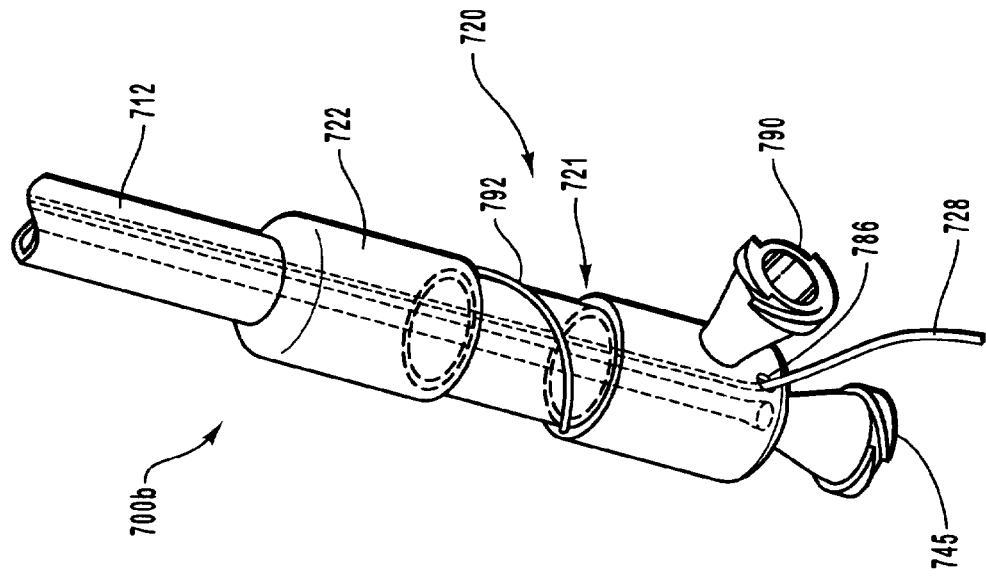
FIG. 26 illustrates a perspective view of a proximal end of yet another embodiment of a stent delivery device in accordance with another aspect of the present invention.

Referring now to FIG. 26, an alternate configuration of delivery device 700a is depicted as illustrated delivery device 700b. In this configuration, the engagement between actuating element 721 and guide member housing 722 can be achieved through complementary threads 792 formed in actuating element 721 and guide member housing 722. These complementary threads 792 can be configured to allow longitudinal movement of actuating element 721 relative to guide member housing 722 through rotational motion of actuating element 721 or motion parallel to the longitudinal axis of guide member 712. By using threads 792, very precise control of the longitudinal movement of the dilation balloon (not shown) and stent (not shown) disposed at distal end 714 of guide member 712 can occur.

Although reference is made to using complementary threads, it can be understood by one skilled in the art in light of the teaching contained herein that various other structures can be used to provide controllable longitudinal movement of actuating element 721 relative to guide member housing 722. For instance, actuating element 721 can include a key that mates with a key way formed in guide member housing 722, or vice versa. Further, although reference is made to rotational motion and motion parallel to the longitudinal movement of the dilation balloon and stent, one skilled in the art can identify various other directions of motion that can enable or facilitate deployment of the dilation balloon and/or stent. For instance, the motion of actuating element can be at any angular orientation relative to the longitudinal axis of the guide member, whether or not such motion includes one or more revolutions of the actuating element relative to the guide member.

Figure 27:
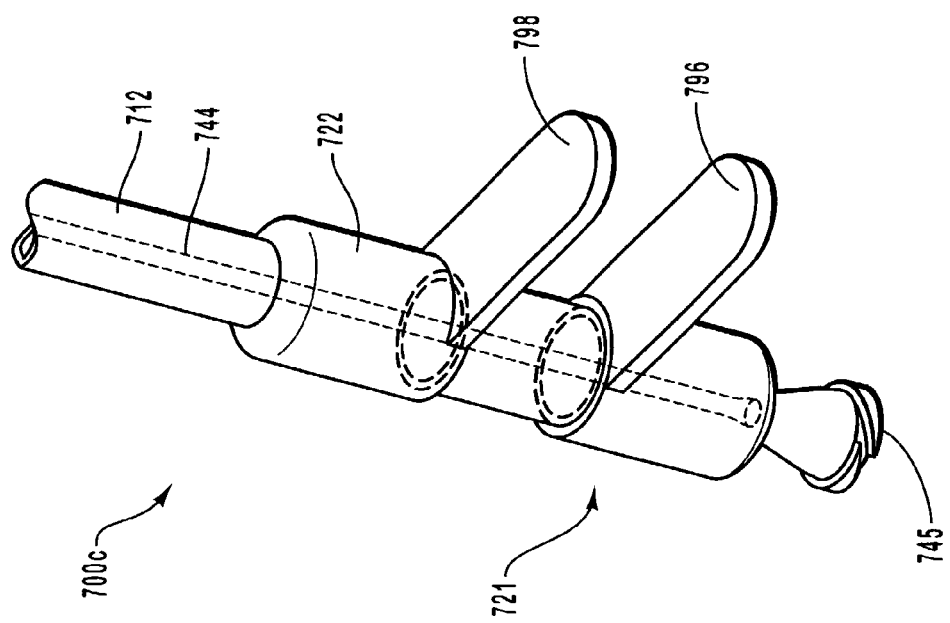
FIG. 27 illustrates a perspective view of a proximal end of yet another embodiment of a stent delivery device in accordance with another aspect of the present invention.

As depicted in FIG. 27, another embodiment of delivery device 700c is illustrated. To aid with moving actuating element 721 relative to guide member housing 722, actuating element 721 and guide member housing 722 and/or guide member 712 can include optional handles 796 and 798 respectively. These handles 796 and 798 can optionally include gripping regions that are adapted to cooperate with one or more appendages of a user of the device. In another configuration, each handle 796 and 798 can have a substantially constant cross-section along their lengths. In still other configurations, each handle 796 and 798 can have variable cross-sections along their lengths. Additionally, although a single luer fitting 745 is depicted in FIG. 27, it can be understood by one skilled in the art that delivery device 700c can include one or more fittings to facilitate introduction of one or more fluids to an interior of delivery device or to a dilation balloon.

Figure 28:
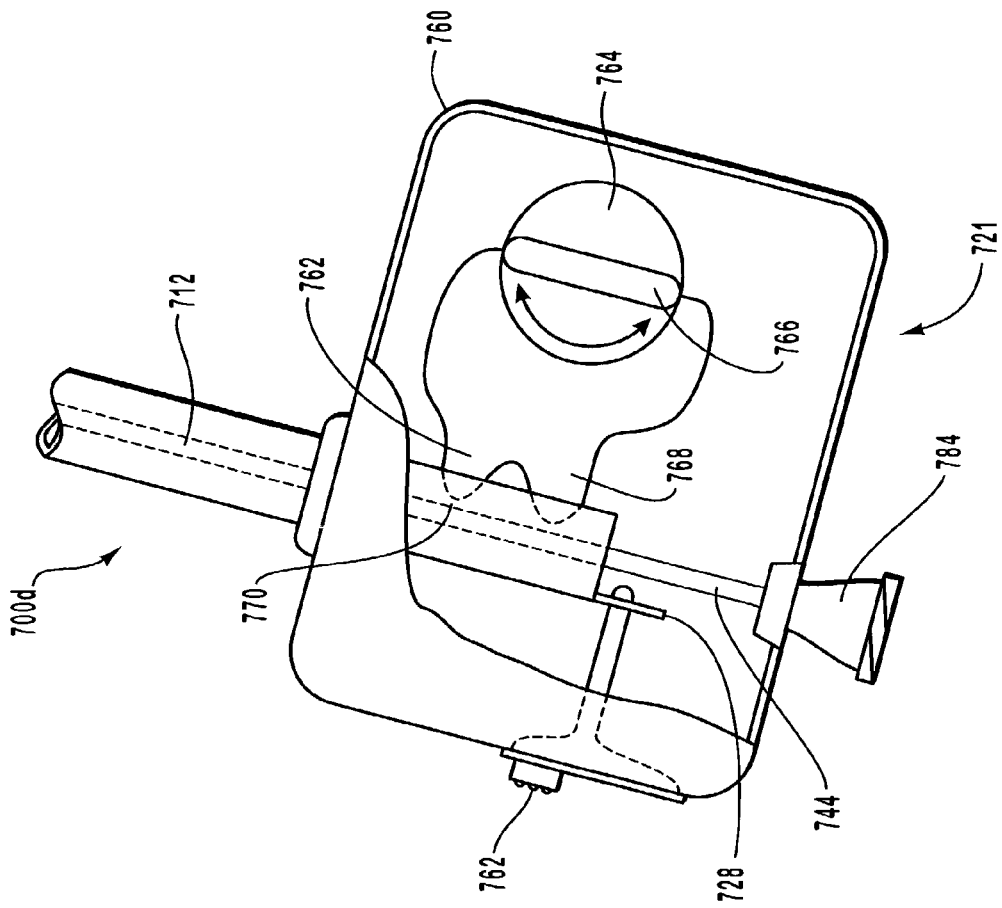
FIG. 28 illustrates another embodiment of the proximal end of another embodiment of a stent delivery device in accordance with another aspect of the present invention.

FIG. 28 shows yet another embodiment of delivery device 700d in which actuating element 721 includes a housing 760 that contains a rotatable gear 762 adapted to cooperate with complementary features or structures 770 formed in a proximal end of guide member 712. The gear 762, with associated one or more teeth, features or structures 768, can be manipulated or rotated by an actuator 764 as a clinician or other individual selects an actuator member 766 and rotates actuator 764 to rotate gear 762. Optionally, actuator 764 has one or more teeth, features or structures that can cooperate with gear 762, such that rotational motion of actuator 764 is translated to movement of gear 762.

As actuator 764 and hence gear 762 are rotated, the complementary features 770 of guide member 712 mate with the teeth, features or structures 768 of gear 762 to move guide member 712 in a proximal and/or distal direction, dependent upon the rotational direction of actuator 764. By so doing, the dilation assembly and the stent can be deployed from a distal end (not shown) of device 700d.

In addition to moving or positioning guide member 712, actuating member 728 may also be operated through using a sliding switch 762 associated with housing 760 and actuating element 721. The actuating member 728 is coupled to a leg 762 that is attached to switch 762, while sliding switch 762 is slidably coupled to housing 760. The sliding translation of switch 762 moves actuating member 728 in the respective direction to release a restraining force applied by the restraining member or mechanism (not shown) of device 700c. One skilled in the art can identify various other configurations of actuating element 721 in light of the teaching contained herein.

Referring now to FIGS. 29-37, depicted are various configurations of alternative embodiments of a delivery device in accordance with the present invention. The features and functions of other described delivery devices apply to the discussion of delivery devices 800a through 800g. Furthermore, it will be appreciated that the majority of features and functions described with respect to delivery device 800a also apply to delivery devices 800b through 800g described further below. The delivery devices of FIGS. 29-37 illustrate various embodiments wherein a delivery device is adapted to be used with a guidewire. For ease of explanation, the embodiments of FIGS. 29-37 do not include a restraining member or mechanism that restrains the dilation assembly and stent inside the guide member. However, it will be appreciated that any restraining member or mechanism with any actuating assembly, as disclosed herein or understood by those of skill in the art, may be employed with devices 800a-800g.

As shown in FIG. 29, delivery device 800a includes a guide member 812 having a proximal end 816 and a distal end 814, with a lumen 818 extending from distal end 814 toward proximal end 816. The distal end 814 can have a similar configuration to the other guide member distal ends described herein. For instance, a restraining member (not shown) may be disposed at distal end 814 to cooperate with structures adapted to restrain a dilation assembly 840 and/or a stent 842. Disposed at proximal end 816 is a guide member housing 822 that cooperates with an actuating element 821 of an actuating assembly 820, in a similar manner to that described with respect to FIG. 6.

Extending from an aperture 834 in a proximal end of actuating element 821 toward distal end 814 of guide member 812 is a guidewire 832. As shown best in FIG. 30, guidewire 832 cooperates with a dilation assembly 840 disposed at a distal end of guide member 812. In this illustrative configuration, dilation assembly 840 includes a tubular member 836 that cooperates with a dilation balloon 846 coupled or attached thereto. The tubular member 836 can function as a positioning member that facilitates deployment of dilation assembly 840 and stent 842. The guidewire 832 extends through tubular member 836 that allows dilation balloon 846, and a stent 842 coupled to dilation balloon 846, to be moved along guidewire 832 when necessary. The internal diameter of a lumen of tubular member 836 is complementary to the exterior diameter of guidewire 832.

Guidewire 832 terminates at a distal end with an atraumatic tip 848 that can include a core wire 856 wrapped with a coiled spring 858. The core wire 856 may be an extension of the remainder of guidewire 832 or alternatively may be a separate member coupled or attached to the distal end of guidewire 832. In either case, core wire 856 can be made from the same or a different material than guidewire 832 and may optionally be a solid member or a tubular member.

The dilation balloon 846 of dilation assembly 840 is inflated through a dilation tube 844 that extends from dilation balloon 846 to terminate at the proximal end of actuating element 821 with a luer fitting 845. An additional luer fitting 890 may be provided attached to actuating element 821. It will be appreciated that luer fitting 890 can perform substantially the same function as luer fitting 790.

The distal end of dilation tube 844 cooperates with an interior of dilation balloon 846. The distal end of dilation tube 84 can be connected to tubular member 836, dilation balloon 846, or to both tubular member 836 and dilation balloon 846. The dilation tube 844 can be used to position dilation balloon 846 and/or stent 842 during a procedure. Consequently, dilation tube 844 can have sufficient strength to enable distal movement of dilation tube 844 to translate to distal movement of the remainder of dilation assembly 840. Similarly, dilation tube 844 can have sufficient strength to enable proximal movement of dilation tube 844 to translate to proximal movement of the remainder of dilation assembly 840.

Delivery device 800a is configured so that guidewire 832 can be positioned in a body lumen, and delivery device 800a can be removed from within the body lumen while retaining guidewire 832 at the desired position. As such, other conventional, interventional devices may then be used to complete the procedure. A device may be connected to the distal end of the guidewire such as, for example, a filter assembly for collecting embolic particles that are dislodged in the body vessel during a stenting operation, as will be discussed in greater detail hereinafter. Other devices may be exchanged over guidewire 832 as will be understood by those of skill in the art.

Figure 31:
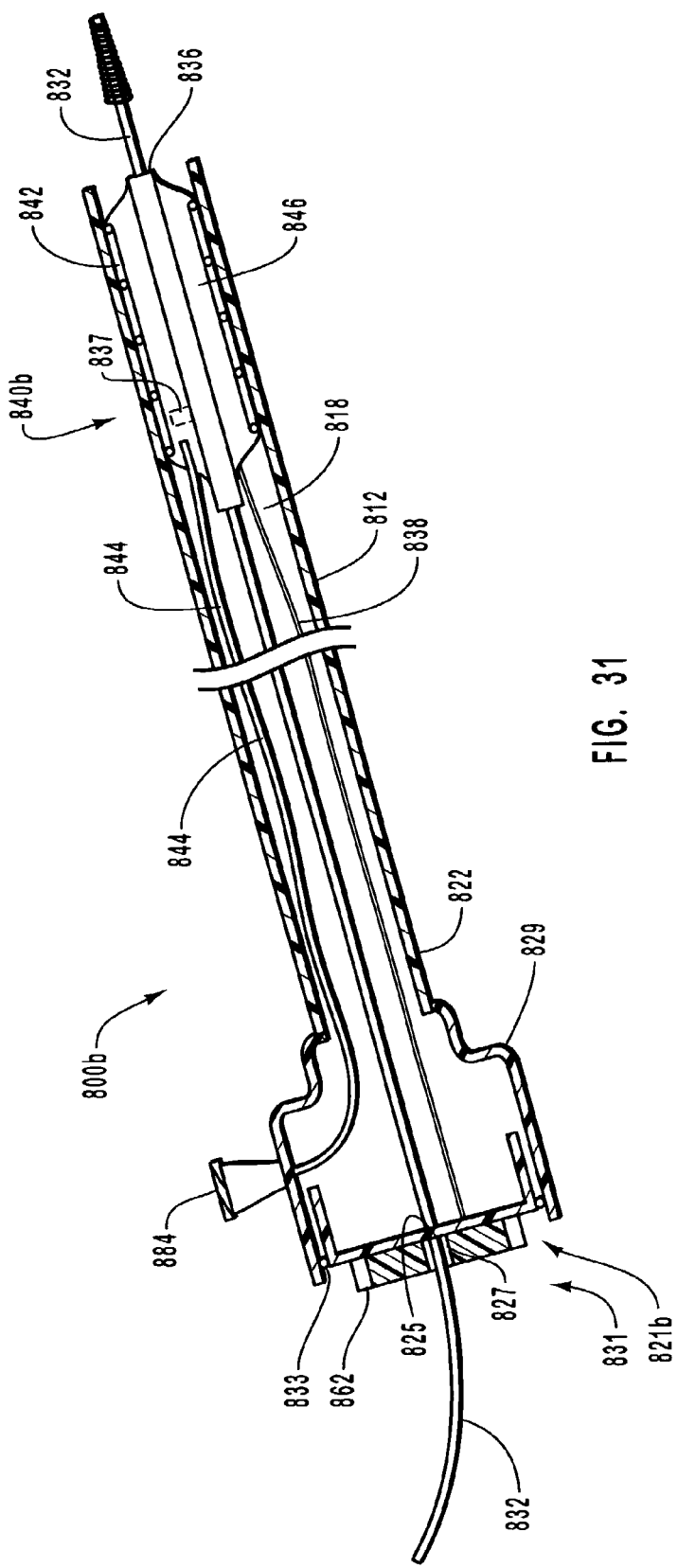
FIG. 31 illustrate sectional side views of another embodiment of a stent delivery device in accordance with another aspect of the present invention.

Depicted in FIG. 31 is another embodiment of a device 800b. The device 800b includes a dilation assembly 840b that is adapted to cooperate with a guidewire 832. As shown, dilation assembly 840b includes a tubular member 836 that cooperates with an expandable dilation balloon 846. Disposed at a proximal end of tubular member 836 is a positioning member 838. The positioning member 838 is coupled to a proximal end of tubular member 836 to facilitate transfer of forces applied to positioning member 838 to tubular member 836 to position dilation assembly 840. The positioning member 838 can be coupled or attached to tubular member 836, dilation balloon 846, or both tubular member 836 and dilation balloon 846, whether such coupling or attachment occurs at a proximal end, distal end, or other portion of tubular member 836 and/or dilation balloon 846 between the respective proximal ends and distal ends thereof. Similarly, the coupling or attaching of positioning member 838 to one or both of tubular member 836 and dilation balloon 846 can be to or upon internal and/or external surfaces of tubular member 836 and dilation balloon 846. By so doing, positioning member 838 can be manipulated by a physician or clinician to position dilation assembly 840b in the desired location to dilate a stent (not shown) and/or lesion. For instance, positioning member 838 can be used to slide dilation balloon 846 along guidewire 832.

As shown, positioning member 838 is separate from dilation tube 844. Although reference is made to positioning member 838 being separate from dilation tube 844, it can be appreciated that positioning member 838 can be removably disposed within dilation tube 844, while being capable of positioning dilation balloon 846 in the desired location within the body lumen or vessel. For instance, as illustrated in dotted lines in FIG. 31, extending from tubular member 836 or formed in tubular member 836 is a stop 837 that can cooperate with a distal end of a positioning member 838 disposed within a lumen of dilation tube 844. By moving the positioning member in the distal direction, the distal end of the positioning member cooperates with stop 837 to move dilation assembly 840b in the distal direction. To move tubular member 836 in the proximal direction, a clinician or physician can move dilation tube 844 in a proximal direction. In another configuration, stop 837 can include a recess (not shown) that friction fits or otherwise cooperates with the distal end of the positioning member, such that the positioning member is retained in the recess with sufficient force that the positioning member can move the tubular member 836 in both proximal and distal directions.

The proximal end of guide member housing 822 as illustrated in FIG. 31, cooperates with an actuating assembly 821b, while a distal end 814 of guide member 812 cooperates with a restraining member or mechanism (not shown) and is adapted to aid in applying a restraining force to dilation assembly 840b and/or stent 842. Actuating element 821b is adapted to enable a clinician to operate delivery device 800b to deliver stent 842, such as in a similar manner to the device described in FIG. 29. For instance, positioning member 838 can be coupled to actuating element 821b such that distal movement of actuating element 821b moves dilation assembly 840b.

In addition, the proximal end of actuating element 821b includes an annular clamping mechanism 862, such as, but not limited to, touhy-borst adaptor, compressible polymer or silicone rubber gasket, or other clamping mechanisms 862 known to those skilled in the art in light of the teaching contained herein. The annular clamping mechanism 862 receives guidewire 832 and creates a mechanical connection and a fluid seal between actuating element 821b and guidewire 832. This seal prevents fluid escaping from within lumen 818, while providing a mechanism for releasing delivery device 800b from guidewire 832 in the event that other conventional, interventional devices are to be used without loosing the vascular access that is gained by the device as a whole. For example, by rotating annular clamping mechanism 862, the seal is broken and delivery device 800b can be removed from guidewire 832. A similar clamp or other seal can cooperate with positioning member 838 to prevent fluid escaping from within device 800b.

Figure 32:
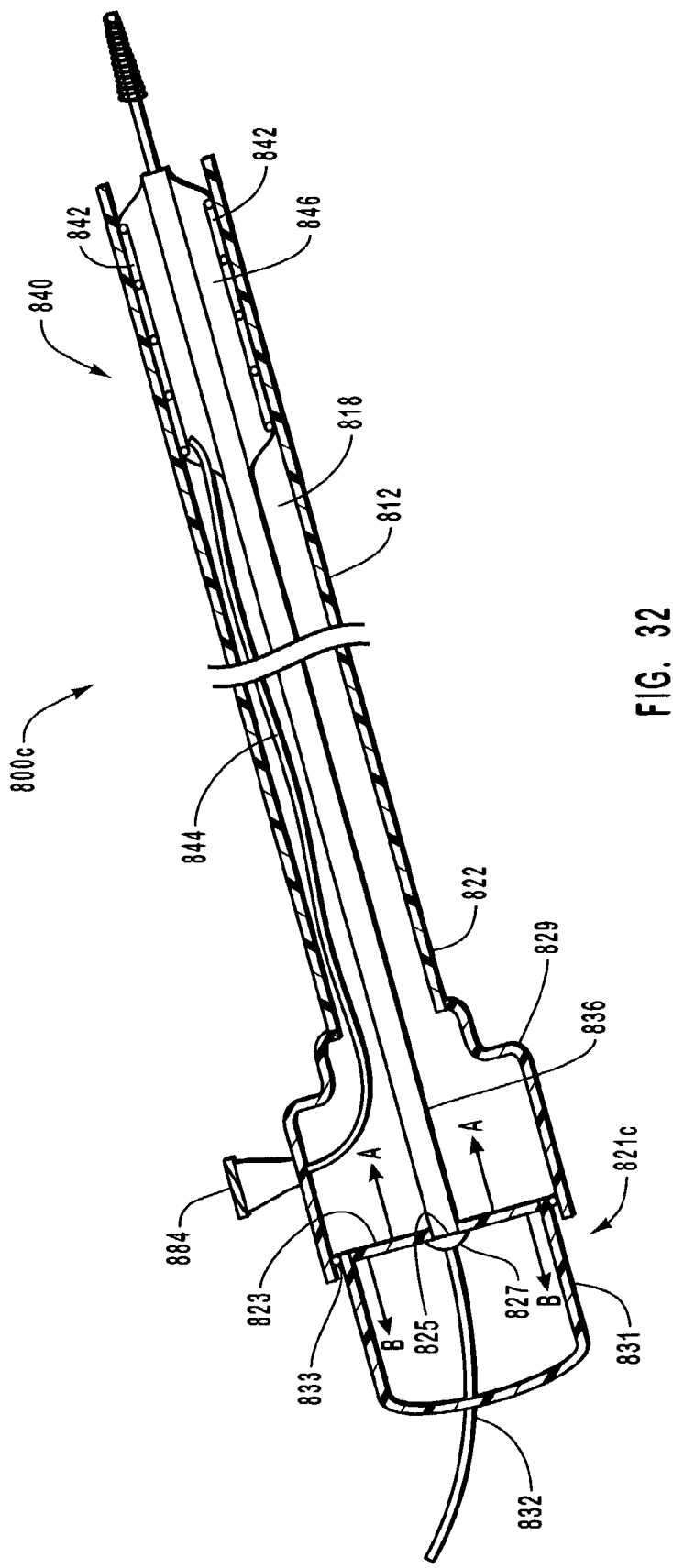
FIG. 32 illustrates a sectional side view of another embodiment of a stent delivery device in accordance with another aspect of the present invention.

FIG. 32 depicts another embodiment of delivery device 800c. In this embodiment, tubular member 836 extends substantially between distal end 814 and proximal end 816 of guide member 812. Tubular member 836 is adapted to receive guidewire 832 therethrough. Thus, tubular member 836 extends from a distal end of dilation balloon 846 to a proximal end of guide member 812, such that the proximal end of tubular member 836 terminates at a point proximal to a proximal end of dilation tube 844. Additionally, the proximal end of tubular member 836 cooperates with a proximal end of guide member 812 and/or an actuating element 821c disposed at the proximal end of guide member 812.

Actuating element 821c includes a fixed portion 829 and a movable portion 831 slidably disposed with portion 829. The portion 829 can be integrally formed with a proximal end of guide member 812 or a separate member that is coupled or attached to the proximal end of guide member 812, where such coupling or attaching can be achieved by complementary threads, key and keyway configuration, chemical bonding, thermal bonding, or adhesives.

The portion 831 cooperates with portion 829 in sealing manner so that a fluid entering an interior space defined by the interiors of portion 829 and a portion of portion 831 is prevented from exiting therefrom. This seal can be created by one or more sealing members 833 and/or between the tolerances associated with portion 829 and portion 831. Illustratively, sealing member 833 can be one or more O-rings in one or more grooves, one or more O-rings, gasket, or viscous fluid seal.

The portion 831 contains a support structure 823 extending across a distal end thereof. The proximal end of tubular member 836 is fixedly attached to support structure 823. Support structure 823 also includes an aperture 825 through which extends guidewire 832. Preferably, a seal 827 is disposed between and/or within aperture 825 and guidewire 832 to retain fluid inside guide member 812. Consequently, upon depressing portion 831 in the direction of arrows A, dilation balloon 846 is deployed from within lumen 818 of guide member 812. Similarly, upon moving portion 831 of actuating element 821c in the direction of arrows B, dilation balloon 846 is retracted into lumen 818 of guide member 812.

As depicted in FIG. 33, another embodiment of delivery device 800d is illustrated. In this embodiment, dilation balloon 846 is coupled or attached directly to guidewire 832. Consequently, positioning member 838 is connected to guidewire 832 and/or optionally dilation balloon 846 instead of tubular member 836. Positioning member 838 is manipulatable by a physician, clinician, or the like to position dilation assembly 840 in the desired location to dilate the stent and lesion. Consequently, by moving positioning member 838, dilation balloon 846 can be placed in the position to optionally pre-dilate the lesion and/or dilate the lesion during implanting of stent 842.

FIG. 34 illustrates another embodiment of delivery device 800e. In this embodiment, positioning member 838 is connected to dilation balloon 846. Positioning member 838 is manipulatable by a physician, clinician, or other individual to position dilation assembly 840 in the desired location to dilate the stent and lesion. Consequently, by moving positioning member 838, dilation balloon 846 can be placed in the position to optionally pre-dilate the lesion and/or dilate the lesion during implanting of a stent (not shown).

Guidewire 832 passes between dilation balloon 846 and stent 842. Although not depicted for ease of explanation, guidewire 832 may have an atraumatic tip attached or formed at a distal end thereof. The dilation balloon 846 includes an integrally formed dilation tube 844 that extends from a distal end of dilation balloon 846. The dilation balloon 846, as with other dilation balloons described herein, can have various configurations, such that dilation balloon 846 can having substantially constant cross-section along its length or alternatively have a variable cross-section along its length. Furthermore, the dilation balloons of the present invention can be formed from one or more separate dilation balloons, with associated one or more dilation tubes, which collectively provide the functionality of a single dilation balloon.

In addition, FIG. 34 depicts a tip 864 disposed at distal end of guidewire 832. Tip 864 provides a transition between guidewire 832 and guide member 812 to limit the potential of damaging the body lumen or vessel of the patient during insertion and removal of delivery device 800e during a procedure. Various types of tips are known to those skilled in the art, such as, but not limited to, those discussed herein and others known to one skilled in the art in light of the teaching contained herein. For instance, tip 864 can have various configurations so long as the configuration provides a transition between guidewire 832 and guide member 812 to aid in preventing damage to the body lumen or vessel during insertion and removal of delivery device 800e. Further, tip 864 can be coupled or attached to guidewire 832 through various manners, such as, but not limited to, adhesives, mechanical bonds, thermally created bonds, being integrally formed therewith, or combinations thereof.

As depicted in FIG. 35, illustrated is another embodiment of delivery device 800f. In this embodiment, guidewire 832 passes between guide member 812 and dilation assembly 840 to terminate distally of a distal end of guide member 812. Although not depicted for ease of explanation, guidewire 832 may have an atraumatic tip attached or formed at a distal end thereof. Connected to dilation balloon 846 is a positioning member 838, similar to those described herein. Positioning member 838 is manipulatable by a physician, clinician, or other individual to position delivery device 800f in the desired location to dilate the stent and lesion. Consequently, by moving positioning member 838, dilation balloon 846 can be placed in the position to optionally pre-dilate the lesion and/or dilate the lesion during implanting of stent 842. Delivery device 800f also includes a tip 864, similar in structure and function to the tip 864 shown and discussed with respect to FIG. 34.

Figure 36:
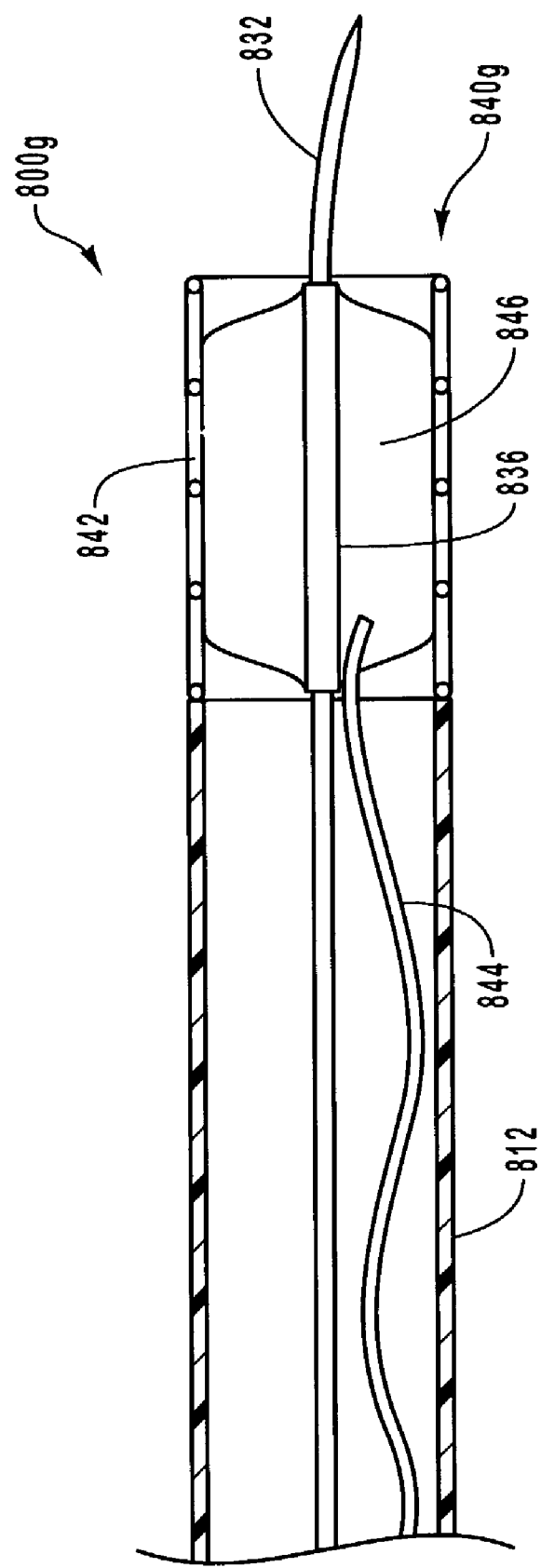
FIG. 36 illustrates a sectional side view of another embodiment of a stent delivery device in accordance with another aspect of the present invention.

FIG. 36 illustrates yet another embodiment of a delivery device of the present invention. As shown, a delivery device 800g includes a dilation assembly 840g, which may be similar to other dilation assemblies described herein, which is disposed past a distal end 814 of guide member 812. Guide member 812 acts as a positioning member to position dilation assembly 840g in the desired location to dilate the stent and lesion. Consequently, by moving guide member 812, dilation balloon 846 can be placed in the position to pre-dilate the lesion and/or dilate the lesion during implanting of a stent. Although not depicted for ease of explanation, guidewire 832 may have an atraumatic tip attached or formed at a distal end thereof.

FIGS. 37 through 44 depict another aspect of the present invention. During a procedure to dilate a lesion and/or implant a stent at a lesion, often emboli becomes dislodged and is carried downstream in the body vessel. To prevent the emboli from blocking even smaller body vessels further downstream, one or more embodiments of the present invention can include means for providing embolic protection. The means for providing embolic protection can be included in a delivery device having a unitary configuration where the delivery device and the means for provide embolic protection, such as a filter device, can be inserted into a body lumen substantially simultaneously.

Referring to FIG. 37, an exemplary delivery device 900 is depicted having many of the same features and functionality of the delivery devices heretofore described. Consequently, the descriptions of the various other delivery devices described herein apply to delivery device 900. As illustrated, delivery device 900 includes a guide member 912 having a dilation assembly 940 and stent 942 disposed therein. It will be appreciated that in the embodiment of FIG. 37 and subsequent embodiments hereafter, a restraining member or mechanism, illustrated in dotted lines, may be disposed at distal end 914 of guide member 912 to restrain dilation assembly 940 and stent 942 adjacent or near distal end 914 of guide member 912 until deployment of same is desired. It will be appreciated that any restraining member or mechanism may be employed as disclosed herein or understood by those of skill in the art. Furthermore, appropriate structures may be employed for deploying dilation assembly 940 and stent 942 as described herein or understood by those skilled in the art.

With continued reference to FIG. 37, delivery device 900 has a filter assembly 931 disposed distally of guide member 912. Consistent with teachings of the present invention, delivery device 900 has a guidewire 932 disposed through dilation assembly 940 and optionally through filter assembly 931. In the illustrated configuration, guidewire 932 terminates at filter assembly 931, with the filter assembly 931 being coupled to a distal end of guidewire 932 and includes an atraumatic tip, as will be described in more detail below.

Filter assembly 931 is adapted to provide embolic protection during use of device 900. As depicted in FIGS. 37 and 38, filter assembly 931 has a low profile to facilitate insertion of the same with a body lumen. A transition member 936 is disposed between filter assembly 931 and dilation assembly 940. The transition member 936 is adapted to provide a transition between guide member 912 and filter assembly 931. This transition prevents damage to the body lumen within which device 900 is disposed and prevents catching upon a wall or junction of one or more body lumens as device 900 is steered through the tortuous anatomy of a patient. As illustrated, transition member 936 includes a passageway 938 disposed therethrough for receiving guidewire 932. Passageway 938 can be adapted to securely retain guidewire 932 therein or optionally removably receive guidewire 932. Alternatively, transition member 936 can include a hole through which guidewire 932 passes or is received. In still another configuration, transition member 936 includes a hole adapted to receive a distal end of guidewire 932, while a distal end of transition member 936 is formed or cooperates with filter assembly 931.

Figure 41:
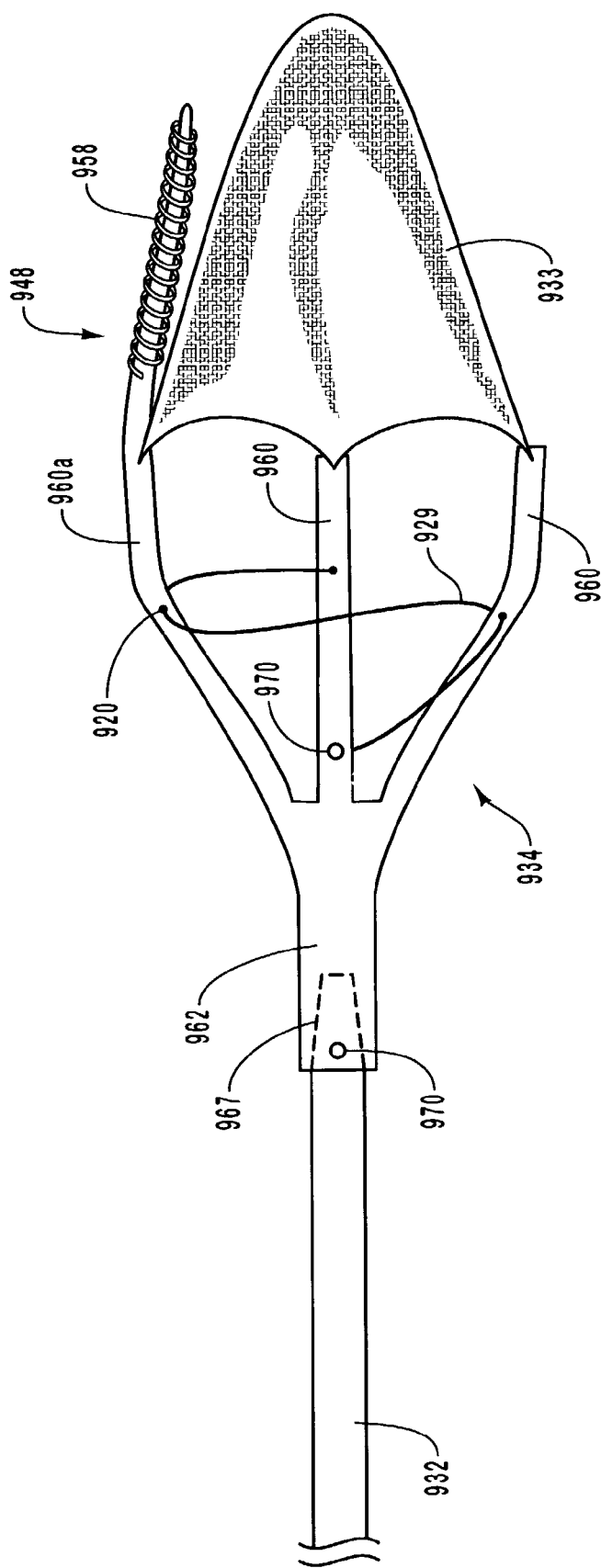
FIG. 41 illustrates a perspective view of a restraining mechanism for a filter assembly usable with the delivery device of FIG. 37 in accordance with another aspect of the present invention.

FIGS. 37 and 38 illustrate filter assembly 931 being restrained in preparation for deploying filter assembly 931, while FIGS. 39-41 depict filter assembly 931 being deployed or activated. As shown in FIG. 41, filter assembly 931 includes a filter basket 934 and a filter 933. Before deployment, filter 933 can be disposed inside filter basket 934, surround filter basket 934, or a combination thereof. The filter 933 is adapted to capture embolic particles or material that may become dislodged during a procedure associated with delivery device 900 or optionally other procedures when delivery device 900 is optionally slidably removed from guidewire 932 and associated filter assembly 931. Consequently, filter 933 can optionally float within a body lumen upon being deployed, with a distal end of filter 933 floating in the body lumen and the proximal end of filter 933 being coupled to filter basket 934. In another configuration, a distal end of filter 933 can be coupled to a portion of filter basket 934.

The filter 933 can be fabricated from a variety of different materials, such as, but not limited to, a woven or braided plastic or metallic mesh, a perforated polymer film, a Nitinol mesh, combinations thereof, or other material that is capable of capturing material within flowing blood, while allowing the blood to flow through the pores or apertures thereof. Generally, filter 933 can be fabricated from a variety of materials so long as filter 932 is capable of being packed within filter basket 934, and optionally float in the blood flow or stream passing through the body lumen within which it is inserted, and is bio-compatible.

Filter 933 can have a variety of differently sized pores ranging from about 50 microns to about 200 microns, from about 60 microns to about 180 microns, or from about 75 microns to about 150 microns. For instance, the pores can have a variety of different configurations, such as but not limited to circular, oval, polygonal, combinations thereof or other configurations known to one skilled in the art in light of the teaching contained herein. In one configuration, therefore, filter 933 can include pores that are differently sized and configured. Consequently, a major or minor axis of each pore can have a variety of different sizes ranging from about 50 microns to about 200 microns, from about 60 microns to about 180 microns, or from about 75 microns to about 150 microns. Generally, the pore size can vary as needed, so long as the pores are sized so that the pores do not compromise blood flow through the filter, i.e., prevent blood flowing through the filter, and collect material that could potentially occlude smaller downstream vessels, potentially blocking blood flow to tissue or result in stroke or infarction.

In addition to the above, filter 933 can be coated with a hydrophilic coating, a heparinized coating, a Polytetrafluoroethylene (PTFE) coating, a silicone coating, combinations thereof, or various other coatings as know or desired by one skilled in the art in light of the teaching contained herein.

The filter basket 934 supports filter 933 following deployment of filter 933. The filter basket 934 includes a plurality of struts 960 that extend from a body 962. Struts 960 of filter basket 934 are adapted to extend outwardly to position filter 933 within the body lumen. A strut 960a of struts 960 can include an atraumatic tip 948, with struts 960a forming at least a portion of the core wire of atraumatic tip 948. This strut may also be covered with a flexible coil 958. The body 962 of filter basket 934 includes a hole 967 that is adapted to receive guidewire 932. Alternatively, body 962 can include a passageway that is adapted to receive a distal end of guidewire 932.

The filter 933 can be attached to struts 960 of filter basket 934 in a variety of ways. For instance, filter 933 can be attached through adhesives, solvent bonding, thermal bonding, mechanical connections, or combinations thereof. Further, the distal end of two or more struts 960 can include a hole through which strands of filter media 932 can be passed and attached to struts 960. Alternatively, the strands can be tied in a knot, folded back upon filter 933, and affixed to filter 933. Various other manners exist of coupling or connecting filter 933 to filter basket 934.

Optionally, filter assembly 931 includes a number of radiopaque bands and/or markers affixed to a variety of positions on filter assembly 931. For instance, bands, markers or other means for radiopacity can be included upon filter 933, filter basket 934 and/or struts 960. In other configurations, the delivery device generally includes means for radiopacity at one or more locations or positions thereof to aid with viewing the position of the delivery device and the various elements and components thereof.

As illustrated, a restraining member or mechanism 925 restrains struts 960, while another retraining member, shown in dotted lines, restrains a distal end of guide member 912. Optionally, restraining member or mechanism 925 restrains both the distal end of guide member 912 and struts 960. FIGS. 37 and 38 depict restraining member or mechanism 925 restraining struts 960, while FIGS. 39-41 depict struts 960 being released from restraining member or mechanism 925. In the exemplary configuration of FIG. 41, restraining member or mechanism 925 has a similar configuration to restraining member or mechanism 525. Therefore, restraining member or mechanism 925 includes a cord 929 forming a number of hoops, with one or more of the hoops being adapted to receive an actuating member 928, which is optionally part of restraining member or mechanism 925. The actuating member 928 is disposed within the hoops so that cord 929 applies a restraining force against struts 960. Actuating member 928 can be removed from the hoops to thereby allow struts 960 to extend outwardly to deploy filter 933. Cord 929 may be made from metallic wires, polymer actuating members, or other materials that can be manipulated to form hoops through which an actuating or securing member. Optionally, cord 929 is adapted to expand outwardly either under the influence of one or more struts or due to a biasing force applied or incorporated within cord 929 by the configuration and/or material of the cord, the hoops, and/or the restraining member.

Cord 929 can be attached to one or more struts 960 of filter assembly 931 through various attachment mechanisms. For instance, cord 929 can be attached to guide member and/or one or more of the struts through adhesives, mechanical fasteners, securing loops, or other manner that securely attaches cord 929 to one or more of struts 960. Alternatively, cord 929 may be attached to actuating member 928 and be removed when actuating member 928 is moved in a proximal direction. A clinician or physician can initiate the longitudinal motion of actuating member 928, either directly or through using of an actuating mechanism or device. Although reference is made to one particular embodiment of restraining member or mechanism 925, one skilled in the art can appreciate that other restraining members or mechanism described herein can be used to restrain struts 960.

As shown, filter basket 934 includes one or more holes 970 that are adapted to receive at least a portion of restraining member or mechanism 925. The holes 970 can be disposed at various locations of filter assembly 931. For instance, and not by way of limitation, body 962 and each strut 960 can include one or more holes 970. The restraining member or mechanism 925 can be at least partially disposed through one or more of holes 970, with cord 929 or other portion of restraining member or mechanism 925 being optionally releasably coupled to one of struts 960 or body 962 of filter basket 934. Moving actuating member 928 of restraining member or mechanism 925 in a proximal direction causes struts 960 to move outwardly to release filter 933.

A proximal end (not shown) of restraining member or mechanism 925 or actuating member 928 can be accessible by a clinician or physician to allow the same to operate restraining member or mechanism 925 to release the restraining force applied to struts 960. Optionally, the proximal end of restraining member or mechanism 925 can cooperate with an actuating assembly that can be operated to move restraining member or mechanism 925 as needed to release the restraining force applied by restraining member or mechanism 925.

In the illustrative configuration of FIGS. 37-41, actuating member 928 of restraining member or mechanism 925 can be moved in a proximal direction with sufficient movement and force to be removed from engagement with the hoops of cord 929. By breaking the coupling or engagement between actuating member 928 and cord 929, struts 960 are allowed to expand or move outwardly to deploy filter 933. Following deploying filter 933, an actuating assembly (not shown) can be manipulated to deploy dilation assembly 940 and stent 942 from guide member 912, in a similar manner to that described herein, and as illustrated in FIG. 40. Therefore, two actuating assemblies can be used, one to release restraining member or mechanism 925 and one to release dilation assembly 940 and stent 942.

It will be appreciated that restraining member or mechanism 925 is but one means for restraining struts 960 of filter basket 934. Other configurations may be employed, such as, but not limited to, the restraining configurations or means for restraining described in FIGS. 2-24. For instance, struts 960 of filter basket 934 can be restrained in the same manner as the strut associated with the guide member of the present invention.

Turning to FIG. 40, depicted is delivery device 900 with filter assembly 931 deployed and dilation assembly 940 and stent 942 deployed from guide member 912. Deploying of dilation assembly 940 and stent 942 can be achieved in a similar manner to that described with respect to other dilation assemblies and stents discussed herein. Similarly, manipulating restraining member or mechanism 925 to release struts 960 and deploy filter 933 can deploy filter assembly 931. Through moving guide member 912 relative to guidewire 932, vice versa, or combinations thereof, dilation assembly 940 and stent 942 can be released from within guide member 912.

Figure 42:
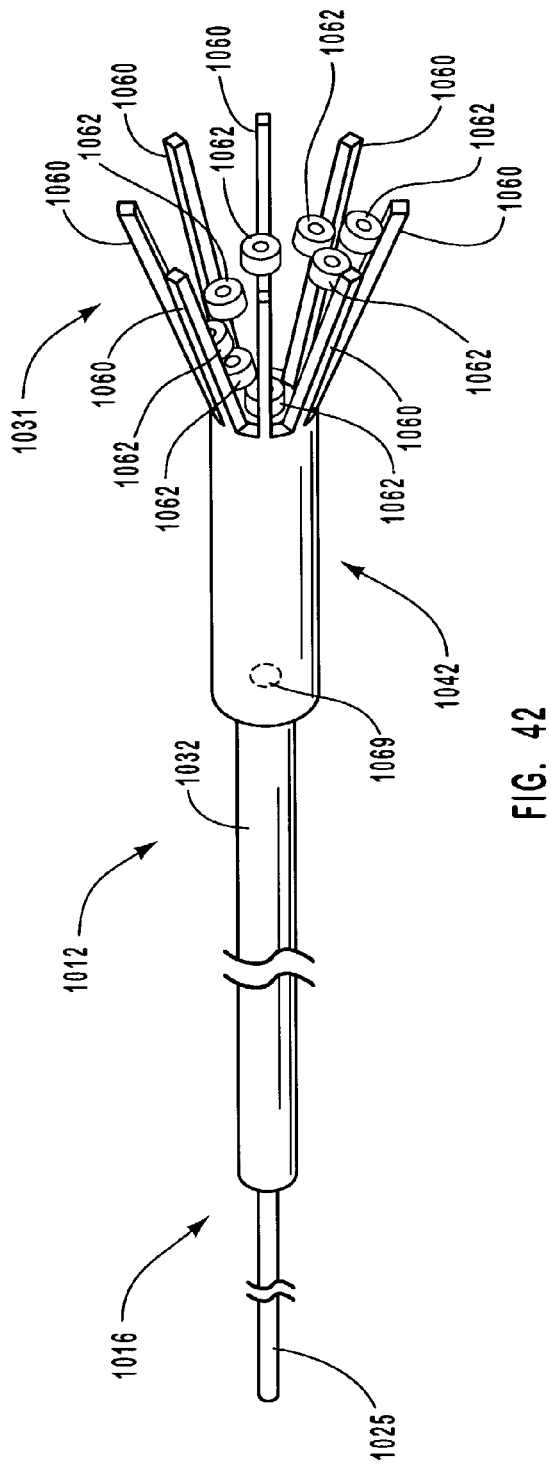
FIG. 42 illustrates a perspective view of a filter assembly usable with the delivery device of FIG. 37 in accordance with another aspect of the present invention.
Figure 43:
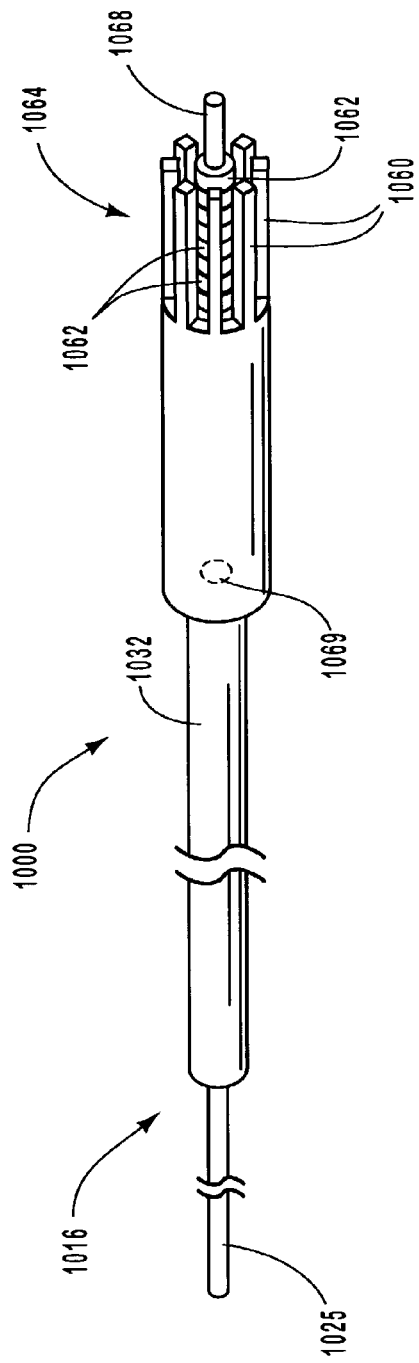
FIG. 43 illustrates a perspective view of the embodiment of the filter assembly of FIG. 42 in accordance with another aspect of the present invention.

FIGS. 42 and 43 illustrate another embodiment of a filter assembly 1031. Filter assembly 1031 has another embodiment of a mechanism for restraining struts 1060. This particular configuration of struts 1060 illustrates that struts 1060 can be coupled to or attached to a distal end of a guidewire 932 or transition member 936 (FIG. 37). The length of struts 1060 can vary based upon the particular configuration of guide member 1012.

A restraining mechanism 1064 maintains struts 1060 in a restrained position as shown in FIG. 43. In this embodiment, restraining mechanism 1064 includes a tubular member 1062 attached to each strut 1060 and a restraining or actuating member 1025 disposed therein. Although reference is made to tubular member 1062 being attached to each strut 1060, it can be understood that one or more tubular members 1062 can be attached to each strut 1060 and/or fewer than each strut 1060 includes tubular member 1062.

Each tubular member 1062 is adapted to receive restraining or actuating member 1025. As shown in FIG. 43, when struts 1060 are restrained, tubular members 1062 are aligned to receive restraining or actuating member 1025. That is, each tubular member 1062 is staggered on adjacent struts 1060 with respect to other tubular members 1062, such that tubular members 1062 line up from the proximal end to the distal end of filter assembly 1031. Restraining or actuating member 1025 is then disposed through the series of tubular members 1062 to restrain struts 1060 and prevents them from extending outwardly, as illustrated in FIG. 43.

Restraining or actuating member 1025 extends from filter assembly 1031 into a lumen of guidewire 1032 to terminate at a proximal end of guide member 1012 and optionally extend beyond the proximal end of guide member 1012. Alternatively, restraining or actuating member 1025 can extend proximally from filter assembly 1031 to exit through an aperture 1069, depicted in dotted lines, before terminating at the proximal end of guide member 1012 and optionally extend beyond the proximal end of guide member 1012. In this latter configuration, restraining or actuating member 1025 can be disposed externally to guide member 1012 or partially externally to guide member 1012 as it extends to the proximal end of guide member 1012 and optionally extend beyond the proximal end of guide member 1012. It will be appreciated that a clinician or physician can manipulate restraining member or mechanism 1064 to release the restraining force applied by restraining member or mechanism 1064. Alternatively, restraining member or mechanism 1064 can be optionally operated by an actuating assembly similar to that described herein, such as, but not limited to, the actuating assembly described with respect to FIG. 6, or any other actuating assembly known by those of skill in the art.

Each tubular member 1062 coupled to struts 1060 can be fabricated from a metal, a plastic, polymer, a polymer, a synthetic materials, whether or not the material is the same as that forming guide member 1012. In one embodiment, each tubular member 1062 is a polymer tube, such as a polyimide or polyurethane tube that is fixed to respective struts 1060 with adhesive. In another configuration, each tubular member 1062 is a metallic cut tube that may be attached to respective struts 1060 with and adhesive or solder. In still another configuration, each strut 1060 includes an aperture through which actuating member 1025 passes to restrain struts 1060 and prevents the same from extending outwardly.

Figure 44:
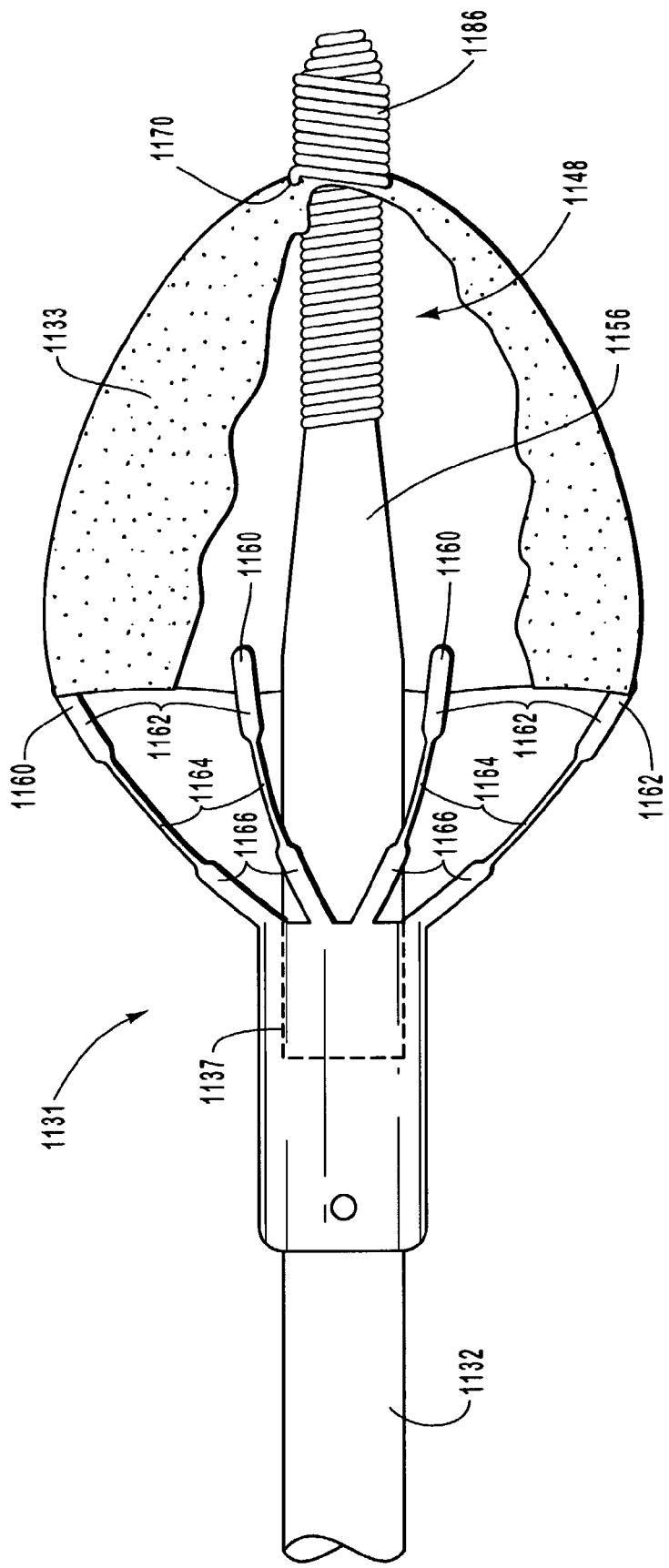
FIG. 44 illustrates a perspective partial sectional view of a distal end of another embodiment of a delivery device in accordance with another aspect of the present invention.

Referring now to FIG. 44 is an exemplary configuration of another filter assembly according to another aspect of the present invention. The features of functions of filter assembly 1131 are applicable to other filter assemblies of the present invention, and vice versa. Furthermore, the discussion related to the one or more other struts of filter assembly 1131 is applicable also to the struts associated with the guide members of the delivery devices of the present invention.

As depicted in FIG. 44, filter assembly 1131 includes a body 1162 and one or more struts 1160. Coupled to one or more struts 1160 is a filter 1133. Extending from body 1162 through filter 1133 is an atraumatic tip 1148, with associated coil 1158. For ease of explanation, the restraining member or mechanism associated with filter assembly 1131 is not shown, however, it will be understood that any of the restraining members or mechanisms described herein can be used to apply a restraining force to one or more struts of filter assembly 1131.

Struts 1160 extend from a body 1162 of filter assembly 1131. Although reference is made herein to struts 1160 being integrally formed with body 1162, it can be appreciated that struts 1160 can be separate members coupled to body 1162. Further, struts 1160 can be integrally formed with guidewire 1132 or separate members coupled to guidewire 1132.

Each strut 1160 includes a distal portion 1162, a proximal portion 1166, and an intermediate portion 1164 disposed between distal portion 1162 and proximal portion 1166. Struts 1160 may attach to filter 1133 on the exterior of filter 1133, on the interior of filter 1133, along the edge of filter 1133, through filter 1133, or combinations of one or more of the proceeding. To provide additional surface area to connect each strut 1160 to filter 1133, each strut 1160 can be configured so that distal portion 1162 has a cross-sectional dimension larger than intermediate portion 1164. Stated another way, distal portion 1162 can have a larger surface area than intermediate portion 1164. The large cross-sectional area provided by the cross-sectional dimension of distal portion 1162 provides large area for bonding each strut 1160 to filter 1133. In this configuration, a strong bond is created between each strut 1160 and filter 1133.

Similarly, each strut 1160 can be configured so that proximal portion 1166 has a cross-sectional dimension larger than intermediate portion 1164, while optionally having a similar, larger, or smaller cross-sectional dimension than distal portion 1162. By having a large cross-sectional dimension and hence large surface area, each strut 1160 can apply a greater biasing force to extend strut 1160 outwardly to deploy filter 1133.

By varying the cross-sectional dimensions of distal portion 1162, intermediate portion 1164, and/or proximal portion 1166, the degree of bias exerted by each strut 1160 to move distal portion 1162 toward the wall of a blood vessel can be varied. The biasing force can also be changed through optionally varying the length of each strut 1160 and/or changing the curvature of each strut 1160.

Although reference is made herein to each strut 1160 having the above-referenced configurations, one skilled in the art can appreciate that one or more of struts 1160 can be configured as described above. Further, each strut 1160 can optionally be configured differently so that each strut 1160 can have similar or dissimilar biasing forces compared to others struts 1160 of the same delivery device. Through varying the biasing forces, the delivery device can be used for a variety of different procedures or blood vessel configurations.

Struts 1160 can be formed from Nitinol, stainless steel, metals, alloys, composites, plastics, polymers, synthetic materials, or combinations thereof. Each strut 1160 can have a generally straight distal portion 1162, proximal portion 1166, and/or intermediate portion 1164. Alternatively, each strut 1160 can have a generally curved distal portion 1162, proximal portion 1166, and/or intermediate portion 1164. In still another configuration, each strut 1160 can have a combination of one or more straight and/or one or more curved portions.

Coupled to body 1162, such as within a lumen or hole 1137, is an atraumatic tip 1148. The atraumatic tip 1148 can include a core wire 1156 and a flexible coil 1158 disposed thereon. Core wire 156 passes through an aperture 1170 in a distal end of filter 1133. Alternatively, core wire 1156 passes through one or more pores formed in filter 1133. To secure filter 1133 to atraumatic tip 1148, a securing coil 1186 surrounds a portion of coil 1158 and the distal end of filter 1133. Although this is one manner to connect filter 1133 to atraumatic tip 1148, one skilled in the art can identify various other manners to connect filter 1133 to atraumatic tip 1148. For instance, the distal end of filter 1133 can be bonded to atraumatic tip 1148 using adhesives, mechanical fasteners, crimping, seals, friction fit, press fit, or other manners to connect filter 1133 to atraumatic tip 1148. In another configuration, filter 1133 is not connected to atraumatic tip 1148 but can slide along a portion of atraumatic tip 1148.

Figure 45:
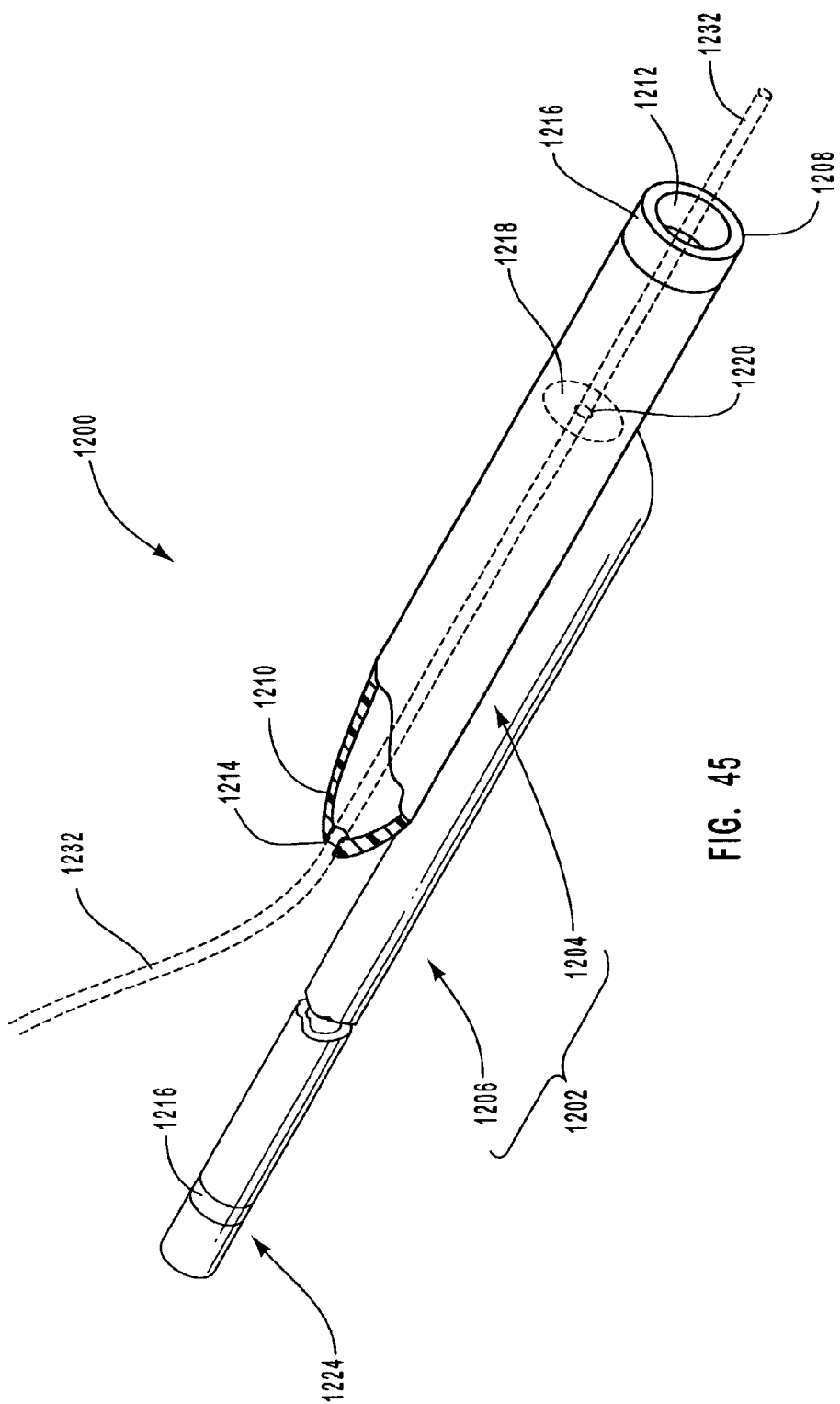
FIG. 45 illustrates a perspective view of an embodiment of a capture mechanism according to one aspect of the present invention.
Figure 46:
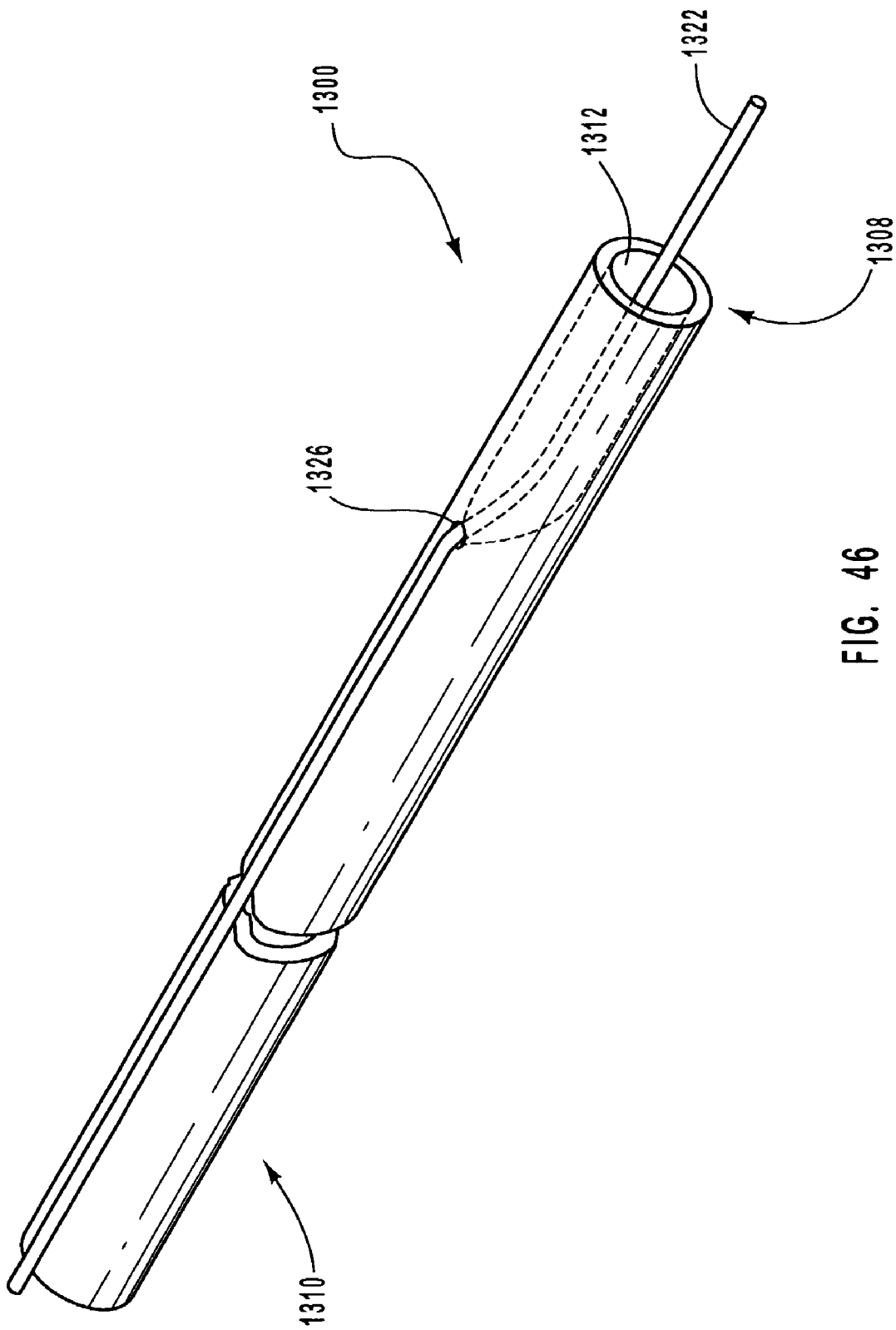
FIG. 46 illustrates a perspective view of another embodiment of a capture mechanism according to one aspect of the present invention.

Turning now to FIGS. 45 and 46, two exemplary embodiments of capturing device or mechanism capable of being used to capture the filter of the filter assembly are depicted. After the filter is deployed, it is desirable to capture the filter after the stenting operation has taken place. More specifically, it is desirable to capture the embolic particles that may have been captured by the filter and remove the same.

FIG. 45 illustrates a capture device 1200 according to one aspect of the present invention. Capture device 1200 includes a capture catheter 1202. As shown, capture catheter 1202 includes a capturing portion 1204 and a positioning member 1206 connected or attached to capturing portion 1204. Capturing portion 1204 has a distal end 1208 and a proximal end 1210. Capturing portion 1204 includes a lumen 1212 extending from distal end 1208 to terminate at an aperture 1214 at proximal end 1210 thereof. The distal end 1208 optionally includes one or more radiopaque markers or bands 1216, only one being shown. Similarly, a proximal end of positioning member 1206 can include one or more radiopaque marker or bands 1216. More generally, capture device and any of the delivery devices and guidewires of the present invention can include one or more radiopaque indicators, whether such indicators are marker, bands, studs, or other radiopaque display elements.

Lumen 1212 is configured to receive a guidewire with attached filter assembly (not shown) of a delivery device. In one embodiment, lumen 1212 can include a stop member 1218, depicted in dotted lines, with a hole 1220 there through. A guidewire, as represented by dotted lines identified by reference numeral 1232, passes through hole 1220 of stop member 1218. The guidewire 1232 can have various configurations, such as, but not limited to those described herein and others known to those skilled in the art.

Stop member 1218 prevents a filter assembly disposed at a distal end of guidewire 1232 to pass through hole 1220 once capture catheter 1202 has received within lumen 1212 the filter assembly associated with guidewire 1232 sufficiently that the filter of the filter assembly is at least closed to prevent escape of embolic material. In one configuration, the filter assembly and associated filter are completely enclosed by capture portion 1204 of capture device 1200. In other configurations, the filter assembly and/or filter are partially enclosed by capture portion 1204 of capture device 1200. One skilled in the art can identify various other configurations of stop member 1218, so long as stop facilitates completely or partially capturing the filter assembly and/or the filter associated with guidewire 1232.

Positioning member 1206 is attached to capture catheter 1202 and can be used to move capture catheter 1202 along guidewire 1232, whether such movement is caused by moving catheter 1202 relative to guidewire 1232, guidewire 1232 relative to catheter 1202, or combination thereof. Positioning member 1206 has sufficient stiffness that application of a force at a proximal end 1224 can be transferred to longitudinal motion of capturing portion 1204 of capture catheter 1202. In one configuration, positioning member 1206 is a solid member, while in another configuration positioning member 1206 is partially or completely hollow. Positioning member 1206 can be fabricated from a polymer, a plastic, polymer, a synthetic material, a metal, an alloy, combinations thereof, or other material that can be used for medical devices and has the needed stiffness.

As illustrated in FIG. 46, an alternate embodiment of a capture device 1300 is illustrated. As shown, capture device 1300 has a form of a tubular member, whether such tubular member is completely hollow or partially hollow along its length. The capture device 1300 includes a capturing portion 1304 disposed at a distal end 1308. A lumen 1312 extends between distal end 1308 and a location proximal of distal end 1308 to terminate at an aperture 1326. In one embodiment, the location of aperture 1326 and the proximal end of lumen 1312 coincide; such that lumen 1312 extends from proximal end 1310 to distal end 1308 of capture device 1300. Aperture 1326 is adapted to receive a guidewire 1332, in a similar manner to aperture 1214 of FIG. 45. Lumen 1312 is configured to receive a filter assembly of a delivery device (not shown). More generally, lumen 1312 completely or partially receives a filter assembly and/or filter associated with guidewire 1322.

Capturing portion 1304 is configured to prevent passage of filter assembly of the delivery device. In this exemplary configuration, the length of lumen 1312 is optionally configured to prevent capturing portion 1304 from being advanced further over the filter assembly and/or the filter thereof than is required. In other configurations, lumen 1312 can be advanced over the filter assembly and/or the filter more than is required to capture the same. In another configuration, lumen 1312 can include a stop member similar to stop member 1218 discussed herein. Furthermore, capturing portion 1304 can optionally include one or more radiopaque markers similar to markers 1216 disposed at and/or between a distal end and a proximal end thereof.

Generally, therefore, embodiments of the present invention can provide systems, methods, and devices that combine the functionality of a guidewire, a stent delivery device, a dilation balloon, an embolic protection device, or subset grouping thereof, into a single device insertable into a body lumen. In this manner, embodiments of the present invention reduce the number of devices needed to perform a procedure, decrease the time needed to perform the procedure, reduce the difficulty and complexity of the procedure, thereby creating the potential for safer procedures and increased effectiveness to the patient.

Portions of the various delivery devices and associated dilation assemblies, stents, guide members, actuator assemblies, guidewires, filter assemblies, and other elements of the present invention can be used interchangeably one with another. Therefore, descriptions of one delivery device and associated components and/or elements is also applicable to other delivery devices described herein and such other devices as known by one skilled in the art in light of the disclosure herein.

The present invention may be embodied in other specific forms without departing all from its spirit or essential characteristics. The described embodiments are to be considered in respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device configured to deliver a stent within a body lumen, the delivery device comprising:
    a stent;
    a dilation assembly configured to assist with placing said stern within a body lumen, said dilation assembly being adapted to cooperate with a guidewire;
    a guide member comprising a distal end portion at least partially surrounding said dilation assembly and said stent, said guide member defining a lumen extending from a distal end of said guide member toward a proximal end of said guide member, said lumen being adapted to receive a guidewire;
    a restraining member adapted to apply a restraining force to said distal end portion of said guide member, said distal end portion of said guide member being arranged to apply a restraining force to said dilation assembly and said stent when said restraining member applies a restraining force to said distal end portion of said guide member; and
    a filter assembly disposed distally of said dilation assembly upon said guidewire, wherein said filter assembly, said guide member, said dilation assembly, and said stent are substantially simultaneously disposed within the body lumen to deliver said stent to the body lumen.

2. The device as recited in claim 1, wherein said dilation assembly comprises:
    a dilation tube adapted to cooperate with said guidewire;
    a dilation balloon mounted to said dilation tube, said dilation tube comprising and interior portion; and
    an inflation tube in fluid communication with said interior portion.

3. The device as recited in claim 2, wherein said guidewire is at least partially disposed in said dilation tube.

4. The device as recited in claim 1, wherein said filter assembly comprises:
    a filter basket; and
    a filter attached to said filter basket.

5. The device as recited in claim 4 wherein said filter basket comprises one or more struts, wherein at least one of said one or more struts is configured to bias outwardly.

6. The device as recited in claim 5, further comprising a second restraining member configured in restrain said filter basket between a restrained position and a released position.

7. The device as recited in claim 6, wherein said second restraining member is a sleeve secured around said one or more struts.

8. The device as recited in claim 7, wherein at least a portion of said second restraining member acts as a stitching to secure said sleeve around said one or more struts.

9. The device as recited in claim 6, wherein said second restraining member comprises a plurality of hinged portions, said plurality of hinged portions being secured by at least a portion of at least one actuating member.

10. The device as recited in claim 6, wherein at least a portion of said second restraining member passes through a gap between at least two of said one or more struts, wherein said second restraining member is secured around said one or more struts.

11. The device as recited in claim 6, wherein said second restraining member comprises one or more separable portions coupled to one or more of said one or more struts.

12. The device as recited in claim 11, wherein at least one actuating member cooperates with said second restraining member, wherein said at least one actuating member is adapted to separate one or more of said one or more separable portions to release the one or more struts.

13. The device as recited in claim 6, wherein said second restraining member comprises a cord secured to one or more of said one or more struts.

14. The device as recited in claim 13, wherein said cord is configured with a plurality of hoops, said plurality of hoops being secured by at least a portion of at least one actuating member 15. The device as recited in claim 6, wherein said second restraining member is a cord threaded through one or more of said one or more struts.

16. The device as recited in claim 6, wherein said restraining member is one or more tubular members individually attached to one or more of said one or more struts, said one or more tubular members being aligned to receive at least a portion of at least one actuating member.

* * * * *

UNITED STATES PATENT AND TRADEMARK OFFICE
CERTIFICATE OF CORRECTION

| | |
|---|---|
| PATENT NO. | : 7,594,926 B2 |
| APPLICATION NO. | : 10/290099 |
| DATED | : September 29, 2009 |
| INVENTOR(S) | : Linder et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1971 days.

Signed and Sealed this

Twenty-eighth Day of September, 2010

David J. Kappos
*Director of the United States Patent and Trademark Office*